US012747299B2

(12) United States Patent
Khalil et al.

(10) Patent No.: US 12,747,299 B2
(45) Date of Patent: Sep. 29, 2026

(54) CD40 BINDING MOLECULES AND USES THEREOF

(71) Applicants: Memorial Sloan Kettering Cancer Center, New York, NY (US); Tri-Institutional Therapeutics Discovery Institute, Inc., New York, NY (US)

(72) Inventors: Danny Nejad Khalil, New York, NY (US); Taha Merghoub, Jersey City, NJ (US); Jedd D. Wolchok, New York, NY (US); Isabell Schulze, New York, NY (US); Ivo C. Lorenz, New York, NY (US)

(73) Assignees: Memorial Sloan Kettering Cancer Center, New York, NY (US); Tri-Institutional Therapeutics Discovery Institute, Inc., New York, NY (US)

( * ) Notice: Subject to any disclaimer, the term of this patent is extended or adjusted under 35 U.S.C. 154(b) by 597 days.

(21) Appl. No.: 18/267,992

(22) PCT Filed: Dec. 16, 2021

(86) PCT No.: PCT/US2021/063870
§ 371 (c)(1),
(2) Date: Jun. 16, 2023

(87) PCT Pub. No.: WO2022/133123
PCT Pub. Date: Jun. 23, 2022

(65) Prior Publication Data

US 2024/0109973 A1 Apr. 4, 2024

Related U.S. Application Data

(60) Provisional application No. 63/126,282, filed on Dec. 16, 2020.

(51) Int. Cl.

| | |
|---|---|
| ***C07K 16/28*** | (2006.01) |
| ***A61P 35/00*** | (2006.01) |
| ***G01N 33/68*** | (2006.01) |

(52) U.S. Cl.
CPC .......... *C07K 16/2878* (2013.01); *A61P 35/00* (2018.01); *G01N 33/68* (2013.01); *C07K 2317/21* (2013.01); *C07K 2317/24* (2013.01); *C07K 2317/31* (2013.01); *G01N 2333/70578* (2013.01)

(58) Field of Classification Search
None
See application file for complete search history.

(56) References Cited

U.S. PATENT DOCUMENTS

| | | | |
|---|---|---|---|
| 2013/0302346 | A1 | 11/2013 | Brommage, Jr. et al. |
| 2017/0088624 | A1 | 3/2017 | Fransson et al. |
| 2019/0022242 | A1 | 1/2019 | Roy et al. |

FOREIGN PATENT DOCUMENTS

| | | | |
|---|---|---|---|
| WO | 2017/184619 | A2 | 10/2017 |
| WO | 2019057792 | A1 | 3/2019 |

OTHER PUBLICATIONS

Robert H. Vonderheide, "CD40 Agonist Antibodies in Cancer Immunotherapy", Annual Review of Medicine, 2020, pp. 47-58, vol. 71.
Xiaojie Yu, et al., "Isotype Switching Converts Anti-CD40 Antagonism to Agonism to Elicit Potent Antitumor Activity", Cancer Cell, 2020, pp. 850-866.e7, vol. 37, No. 6.
Lee P. Richman & Robert H. Vonderheide, "Role of crosslinking for agonistic CD40 monoclonal antibodies as immune therapy of cancer", Cancer Immunology Research, 2014, pp. 19-26, vol. 2, No. 1.

*Primary Examiner* — Maher M Haddad
(74) *Attorney, Agent, or Firm* — Grimes & Yvon LLP

(57) ABSTRACT

The present invention provides various CD40 binding molecules (including, but not limited to, antibodies), compositions comprising such CD40 binding molecules, and methods of using such CD40 binding molecules and compositions, for example for CD40-mediated activation of cells, such as antigen presenting cells.

19 Claims, 34 Drawing Sheets

Specification includes a Sequence Listing.

Donor E

Donor F

C

D

Donor G

Donor H

A

B

CD40 BINDING MOLECULES AND USES THEREOF

CROSS-REFERENCE TO RELATED APPLICATIONS

This application is a National Stage of International Application No. PCT/US2021/063870, filed Dec. 16, 2021, which claims benefit of U.S. Provisional Application No. 63/126,282, filed Dec. 16, 2020, the entireties of both of which are herein incorporated by reference.

STATEMENT REGARDING FEDERALLY SPONSORED RESEARCH OR DEVELOPMENT

This invention was made with government support under grant number CA008748 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 8, 2021, is named MSKCC_048_WO1_SL.txt and is 17,823 bytes in size.

INCORPORATION BY REFERENCE

All references cited in this disclosure are hereby incorporated by reference in their entireties (numbers in parentheses or in superscript following text in this patent disclosure refer to the numbered references provided in the "Reference List" section of this patent specification). In addition, any manufacturers' instructions or catalogues for any products cited or mentioned herein are incorporated by reference. Documents incorporated by reference into this text, or any teachings therein, can be used in the practice of the present invention.

BACKGROUND

Immunotherapy with immune checkpoint blockade (anti-CTLA4, anti-PD-1/PD-L1) has had a major impact on cancer treatment.[1] Despite this success, the majority of cancer patients (over 80%) still do not benefit from it. A major hurdle to overcome resistance to immune checkpoint blockade is proper activation of antigen presenting cells (APCs), particularly dendritic cells (DCs), which are responsible for priming T cells. Many cancers (including breast[2] colorectal[3] lung[4] and prostate[5] cancer) demonstrate defective APC activation. Since APCs are responsible for priming T cells, this may at least partly explain the absence of a productive anti-tumor T cell response in immunotherapy-refractory cancers.

Stimulation of CD40 on APCs has been recognized as a highly effective way to activate APCs.[6,7] Indeed, CD40 agonists have demonstrated antitumor activity as monotherapy in human cancers.[8-10] Currently there is great interest in the use of CD40 stimulation in the treatment of pancreatic cancer, in part because of compelling early-phase data incorporating the CD40 agonist mAb APX005M (developed by Apexigen) in the first-line treatment of metastatic pancreatic cancer.[11] And in studies performed in mice, it has been shown that a CD40 agonist antibody can be used to overcome resistance to PD-1 blockade and that combining CD40 activation with TLR4 stimulation using monophosphoryl lipid A (MPL) can restore sensitivity to PD-1 blockade, confer persistent antitumor immunity, and overcome the challenge of T-cell exhaustion in tumors.[12]

It has been demonstrated that CD40 agonist antibodies with a modified Fc portion that increases binding to a specific Fc receptor—FcγRIIB, present on intratumoral myeloid cells—can more potently stimulate APCs.[13] This has led to the production of a series of CD40 agonist antibodies designed to have increased FcγRIIB binding, including the antibodies referred to as APX005M[14] and 2141-V11[15]. However, the utility of such antibodies is dependent on specific defined populations of tumor-infiltrating immune cells that vary widely between patients.[16] Thus, there remains a need in the art for agents that stimulate CD40 and enhance APC activation-independent of the presence of patient-specific populations of tumor-infiltrating immune cells. The present invention addresses this need.

SUMMARY OF THE INVENTION

The present invention provides novel CD40 binding molecules that were designed specifically to compete with CD40's ligand (CD40L) for binding to CD40 and to have intrinsic CD40 agonist activity on antigen-presenting cells without a requirement for Fc receptor engagement. The process by which these CD40 binding molecules were developed is described in the Examples section of this patent disclosure, and the amino acid sequences of several of these CD40 binding molecules (and their key binding determinants, including their CDRs) are provided in the Detailed Description section of this patent disclosure. As described further in the Examples section of this patent disclosure, these novel CD40 binding molecules exhibit robust antitumor activity in vivo in a clinically relevant model of melanoma-without dependence on Fc receptor engagement or intratumoral immune cell populations that vary greatly between patients.

Accordingly, in some embodiments the present invention provides isolated CD40 binding molecules comprising: the complementarity-determining region (CDR) H1, CDR H2 and CDR H3 regions of SEQ ID NO. 1, and the CDR L1, CDR L2, and CDR L3 regions of SEQ ID NO. 2.

Similarly, in some embodiments the present invention provides isolated CD40 binding molecules comprising: (i) the CDR H1 and CDR H2 regions of SEQ ID NO. 1, (ii) the CDR H3 region of SEQ ID NO. 1, 3, 5, 7, or 17, and (iii) the CDR L1, CDR L2, and CDR L3 regions of SEQ ID NO. 2.

And, in other embodiments the present invention provides isolated CD40 binding molecules comprising: (i) the CDR H1 and CDR H2 regions of SEQ ID NO. 1, (ii) a CDR H3 region comprising SEQ ID NO. 16, and (iii) the CDR L1, CDR L2, and CDR L3 regions of SEQ ID NO. 2.

In further embodiments the present invention provides isolated CD40 binding molecules comprising: (i) a heavy chain variable region comprising: a CDR H1 domain comprising SEQ ID NO. 9, a CDR H2 domain comprising SEQ ID NO. 10, and a CDR H3 domain comprising SEQ ID NO. 16, and (ii) a light chain variable region comprising: a CDR L1 domain comprising SEQ ID NO. 12, a CDR L2 domain comprising the amino acid sequence FTS, and a CDR L3 domain comprising SEQ ID NO. 13. In some such embodiments the CDR H3 domain in the CD40 binding molecule comprises SEQ ID NO. 11 or SEQ ID NO. 14 or SEQ ID NO. 15. In some such embodiments the CDR H3 domain in the CD40 binding molecule comprises SEQ ID NO. 11. In some such embodiments the CDR H3 domain in the CD40 binding molecule comprises SEQ ID NO. 14. In some such embodiments the CDR H3 domain in the CD40 binding molecule comprises SEQ ID NO. 15.

In some embodiments the present invention provides isolated CD40 binding molecules that comprise (a) a heavy chain variable region comprising SEQ ID NO. 3, SEQ ID NO. 5, or SEQ ID NO. 7, and (b) a light chain variable region comprising SEQ ID NO. 4, SEQ ID NO. 6, or SEQ ID NO. 8—all of which variable region sequences are humanized.

In some embodiments the present invention provides CD40 binding molecules that comprise (a) a heavy chain variable region comprising amino acids 1-121 of SEQ ID NO. 1, and (b) a light chain variable region comprising amino acids 1-113 of SEQ ID NO. 2—which variable region sequences are humanized.

In some embodiments the present invention provides CD40 binding molecules that comprise (a) a heavy chain variable region comprising SEQ ID NO. 17 and (b) a light chain variable region comprising SEQ ID NO. 18-which variable region sequences are murine.

In some embodiments the CD40 binding molecules further comprise a human constant region. In some such embodiments such CD40 binding molecules further comprise a human IgG constant region. In some such embodiments such CD40 binding molecules further comprise a human IgG2 constant region.

In some embodiments the CD40 binding molecules comprise a heavy chain comprising SEQ ID NO. 1, and a light chain comprising SEQ ID NO. 2.

The above sequences, as identified by their SEQ ID NOs, are provided in Tables A & B in the Detailed Description section of this patent disclosure.

In some embodiments the CD40 binding molecules described above or elsewhere herein are, or comprise, antibodies. For example, in some embodiments the CD40 binding molecules are, or comprise, humanized antibodies, fully human antibodies, chimeric antibodies, bi-specific antibodies, or multi-specific antibodies.

In some embodiments the CD40 binding molecules described above or elsewhere herein are, or comprise, antibody fragments. Examples of such antibody fragments include, but are not limited to, Fv, Fab, F(ab')2, Fab', single chain Fv (scFv), sc(Fv)2, and disulfide-linked (dsFv) fragments.

In some embodiments the CD40 binding molecules described above or elsewhere herein are, or comprise diabodies, nanobodies, triabodies, tetrabodies, nanobodies, or minibodies.

In those embodiments where a CD40 binding molecule as described above or elsewhere herein comprises a heavy chain constant region, or a portion thereof, the heavy-chain constant region may be an alpha, delta, epsilon, gamma, or mu heavy chain constant region.

Similarly, in some embodiments, the CD40 binding molecules described herein may be, or may comprise, an IgA, IgD, IgE, IgG or IgM class immunoglobulin molecule. In some embodiments, the CD40 binding molecules described herein may be, or may comprise, an IgG1, IgG2, IgG3, or IgG4, class immunoglobulin molecule. In some embodiments, the CD40 binding molecules described herein may be, or may comprise, an IgG1 or IgG2 class immunoglobulin molecule. In some embodiments, the CD40 binding molecules described herein may be, or may comprise, an IgG2 class immunoglobulin molecule.

In those embodiments where a CD40 binding molecule as described above or elsewhere herein comprises a light chain constant region, or a portion thereof, the light-chain constant region may a lambda light chain constant region or a kappa light chain constant region.

In some embodiments, the present invention also provides isolated CD40 binding molecules that bind to the same epitope on human CD40 as any one of the CD40 binding molecules described above or elsewhere herein. Similarly, in some embodiments the present invention provides isolated CD40 binding molecules that compete with any one of the CD40 binding molecules described above or elsewhere herein for binding to human CD40.

In addition to the various CD40 binding molecules described herein, the present invention also provides various compositions comprising such CD40 binding molecules, for example pharmaceutical compositions that comprise a CD40 binding molecule as described herein and a pharmaceutically acceptable carrier.

The present invention also provides nucleotide sequences that encode the CD40 binding molecules described herein.

The present invention also provides vectors that comprise nucleotide sequences that encode the CD40 binding molecules described herein. In some of such embodiments the vectors are expression vectors, for example comprising a nucleotide sequence that encodes a CD40 binding molecule operatively linked to a promoter.

Similarly, the present invention also provides cells (including human cells and murine cells) that comprise nucleotide sequences that encode the CD40 binding molecules described herein. Similarly, in some embodiments the present invention provides cells (including human cells and murine cells) that comprise nucleotide sequences that encode the CD40 binding molecules described herein operatively linked to a promoter and that express the CD40 binding molecules described herein.

The present invention also provides methods of use of the CD40 binding molecules, compositions, and cells described herein.

For example, in some embodiments the present invention provides methods for CD40-mediated activation of cells, such methods comprising contacting cells that express CD40 with a CD40 binding molecule as described herein (or a composition, such as a pharmaceutical composition, comprising such a CD40 binding molecule), thereby inducing intracellular signaling pathways. In some embodiments the present invention provides methods for activating cells expressing CD40, such methods comprising contacting cells that express CD40 with a CD40 binding molecule as described herein (or a composition, such as a pharmaceutical composition, comprising such a CD40 binding molecule), thereby activating CD40-induced signaling pathways in the cells. In some such embodiments the cells are myeloid cells. In some such embodiments the cells are lymphoid cells. In some such embodiments the cells are endothelial cells. In some such embodiments the cells are immune cells. In some such embodiments the cells are cells with innate or adaptive immune cell function. In some such embodiments the cells are antigen presenting cells. In some embodiments the antigen presenting cells are dendritic cells. In some embodiments the antigen presenting cells are B cells. In some embodiments the antigen presenting cells are macrophages. In some embodiments the cells are in vitro. In some embodiments the cells are in vivo.

In some embodiments the present invention provides methods of activating T cells via CD40-mediated activation of antigen presenting cells, such methods comprising contacting the antigen presenting cells with a CD40 binding molecule as described herein (or a composition, such as a pharmaceutical composition, comprising such a CD40 binding molecule). In some embodiments the antigen presenting cells are dendritic cells. In some embodiments the antigen presenting cells are B cells. In some embodiments the antigen presenting cells are macrophages. In some embodiments the antigen presenting cells are monocytes. In some embodiments the antigen presenting cells are endothelial cells. In some embodiments the cells are in vitro. In some embodiments the cells are in vivo.

In some embodiments the present invention provides methods for treating melanoma in subjects in need thereof, such methods comprising administering to a subject that has melanoma an effective amount of a CD40 binding molecule as described herein, (or a composition, such as a pharmaceutical composition, comprising such a CD40 binding molecule). In some such embodiments the method results in regression of a melanoma in the subject. In some such embodiments the method results in limiting proliferation of melanoma tumor cells in the subject. In some such embodiments the method results in killing of melanoma tumor cells in the subject. In some embodiments the survival of subjects treated with such methods is increased as compared to that of subjects with melanoma that are not so treated.

The present invention also provides methods for detecting CD40 or CD40-expressing cells in a sample (such as in a cell or tissue sample—e.g., a biopsy sample) or in a subject. Such methods typically involve contacting a cell or tissue sample with a CD40 binding molecule as described herein, and performing an assay to determine whether the CD40 binding molecule binds to the cell or tissue sample and/or performing an assay to quantify any binding of the CD40 binding molecule binds to the cell or tissue sample.

These and other embodiments of the invention are further described in the "Brief Description of the Figures," "Detailed Description," "Examples," "Figures," and "Claims" sections of this patent disclosure, each of which sections is intended to be read in conjunction with, and in the context of, all other sections of the present patent disclosure. Furthermore, one of skill in the art will recognize that the various embodiments of the present invention described herein can be combined in various ways, and that such combinations are within the scope of the present invention.

("Ab2 hIgG1 S267E"), and dacetuzumab (Seattle-Genetics) ("Ab3-hIgG1") were also included. Expression of the DC activation markers HLA-ABC (FIG. 10 A) and CD80 (FIG. 10 B) was analyzed by flow cytometry.

Figure 11:
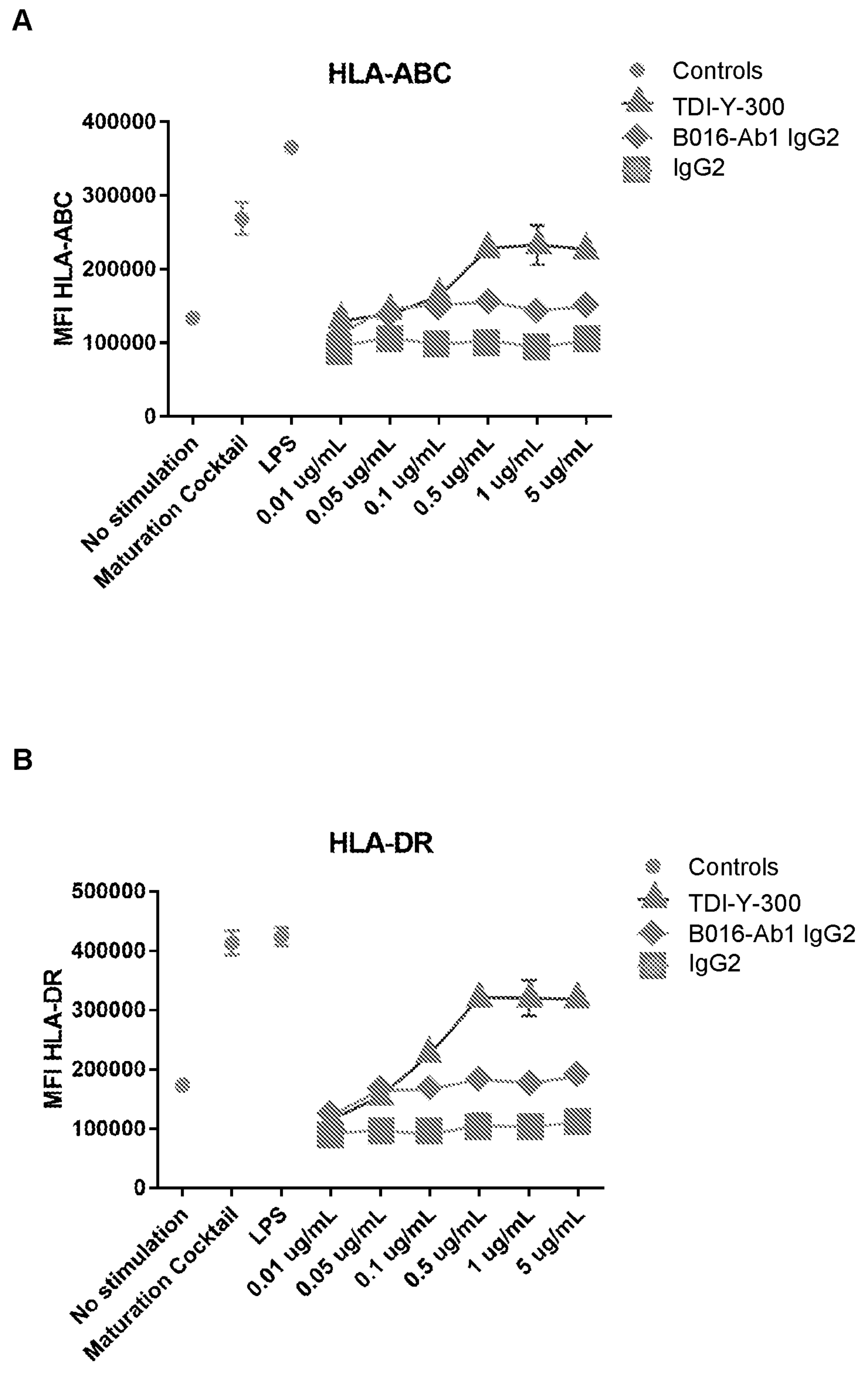
Figure 11:
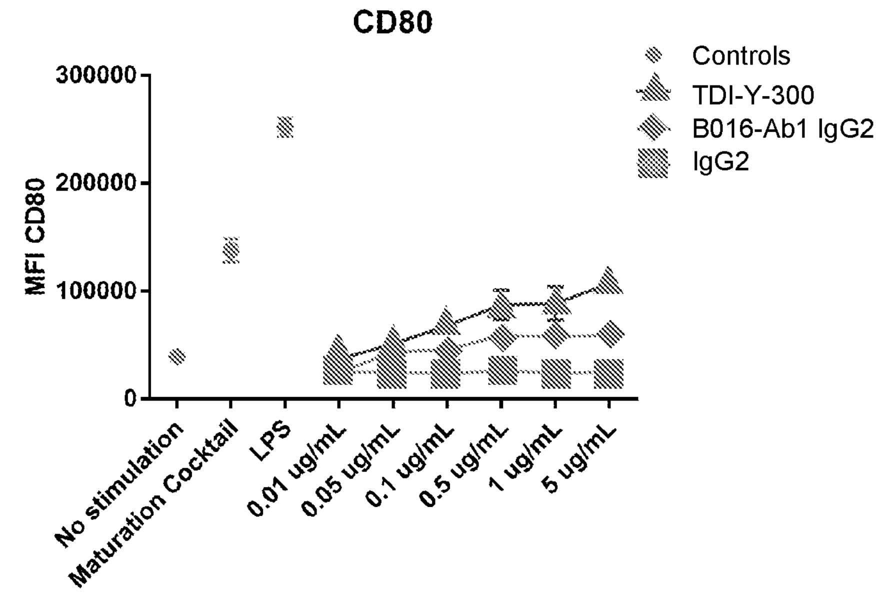
Figure 11:
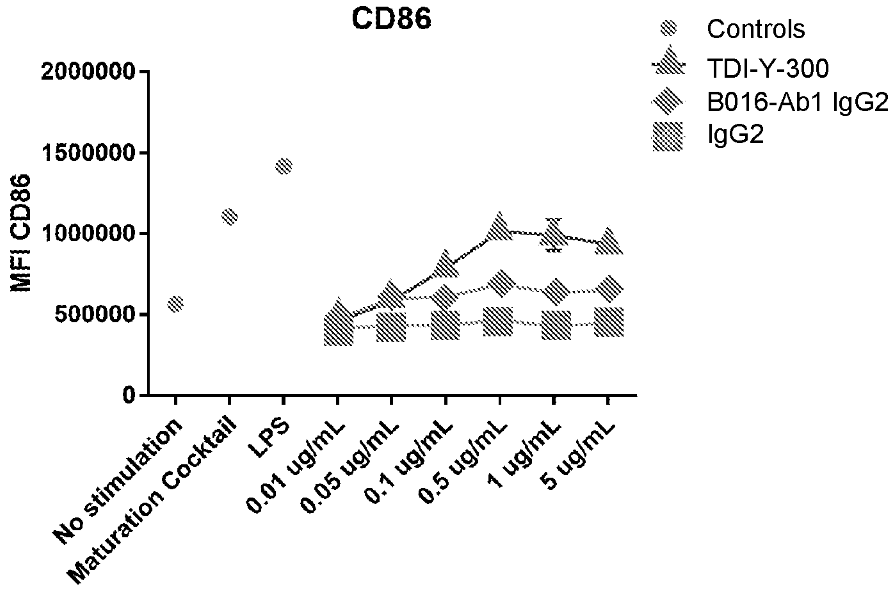

FIG. 11 A-B. Response curves of dendritic cells to TDI-Y-003 or comparator CD40 agonist. Dose response curves for dendritic cells from an individual healthy donor is shown. MFI values for HLA-ABC (FIG. 11 A), HLA-DR (FIG. 11 B), CD80 (FIG. 11 C), and CD86 (FIG. 11 D) are depicted in response to 48 hours stimulation with TDI-Y-003, CD40 agonist B016-Ab1 hIgG2 (equivalent to CP-870893 or selicrelumab), or human IgG2 isotype control.

Figure 12:
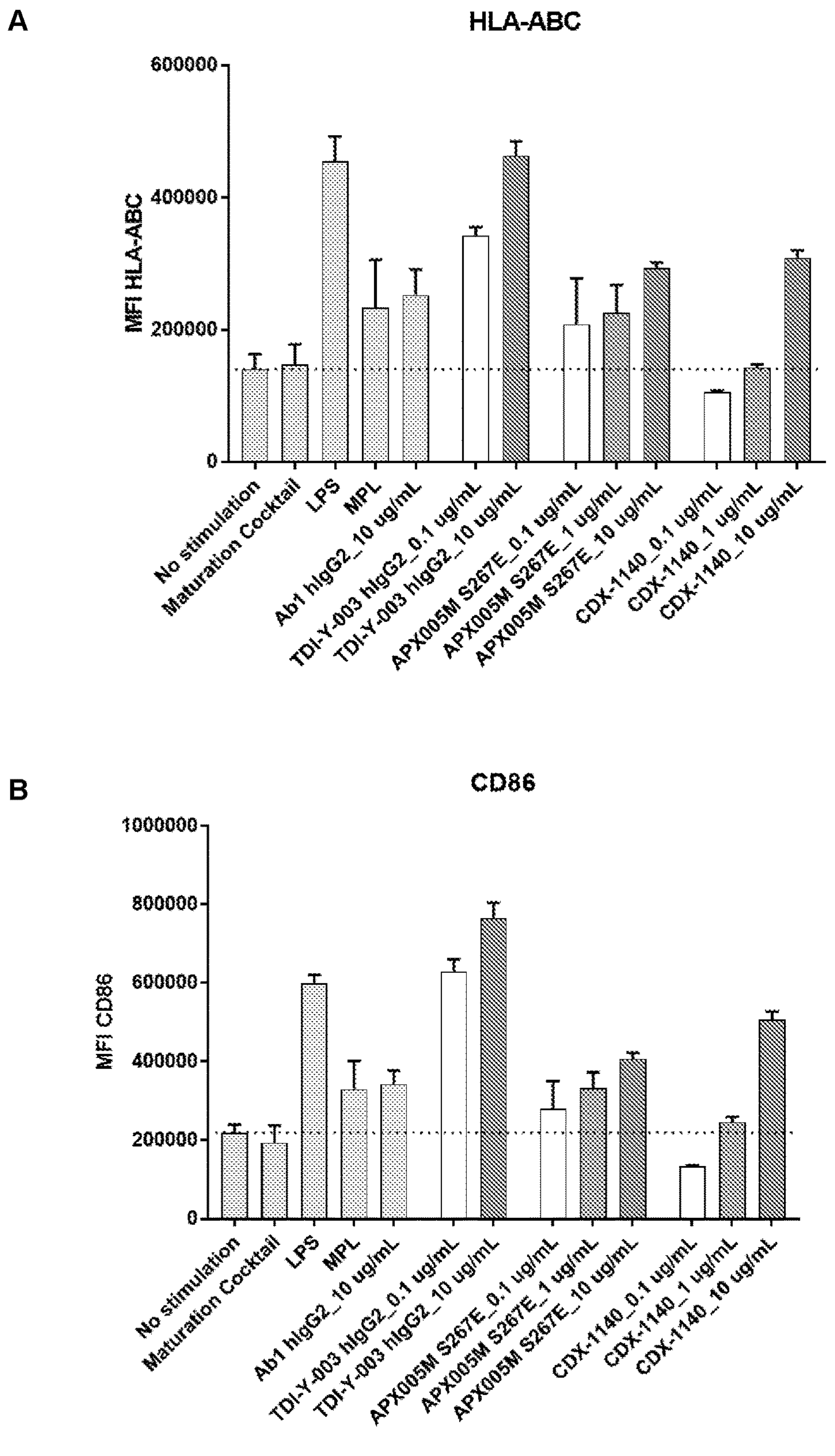

FIG. 12 A-B. Activation of dendritic cells by TDI-Y-003 or comparator CD40 agonists. Dendritic cells from a healthy donor were stimulated with TDI-Y-003, CD40 agonist APX005M, CD40 agonist CDX-1140, or human IgG2 isotype control. Negative (no stimulation) and positive (maturation cocktail, LPS, MPL) assay controls are shown. Expression of the DC activation markers HLA-ABC (FIG. 12 A) and CD86 (FIG. 12 B) was analyzed by flow cytometry.

Figure 13:
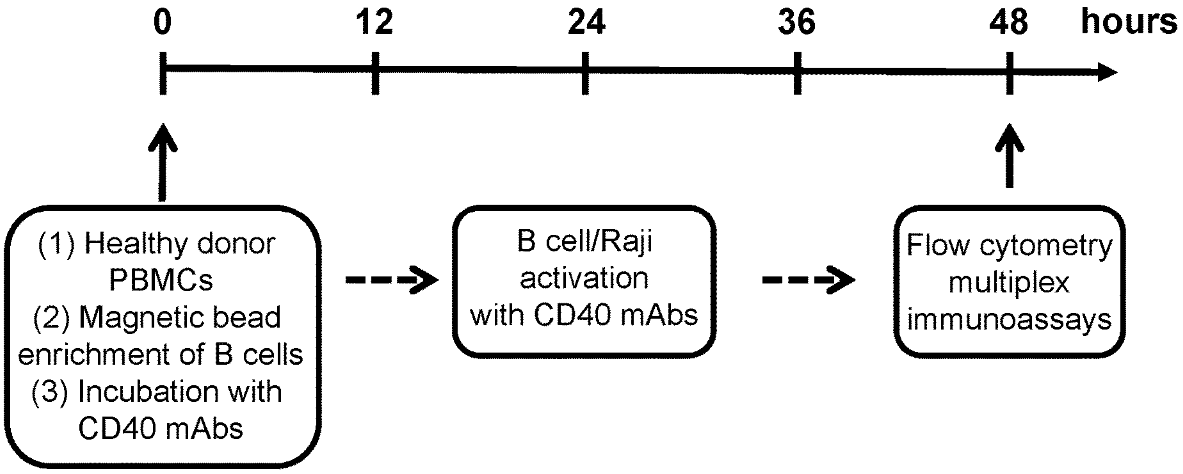

FIG. 13. Cell processing and stimulation schedule. B cells were obtained from magnetic bead-enrichment of PBMCs. Both B cells and Raji B-lymphoblastic cells were stimulated for 48 hours with test agents (TDI-Y-003, controls).

Figure 14:
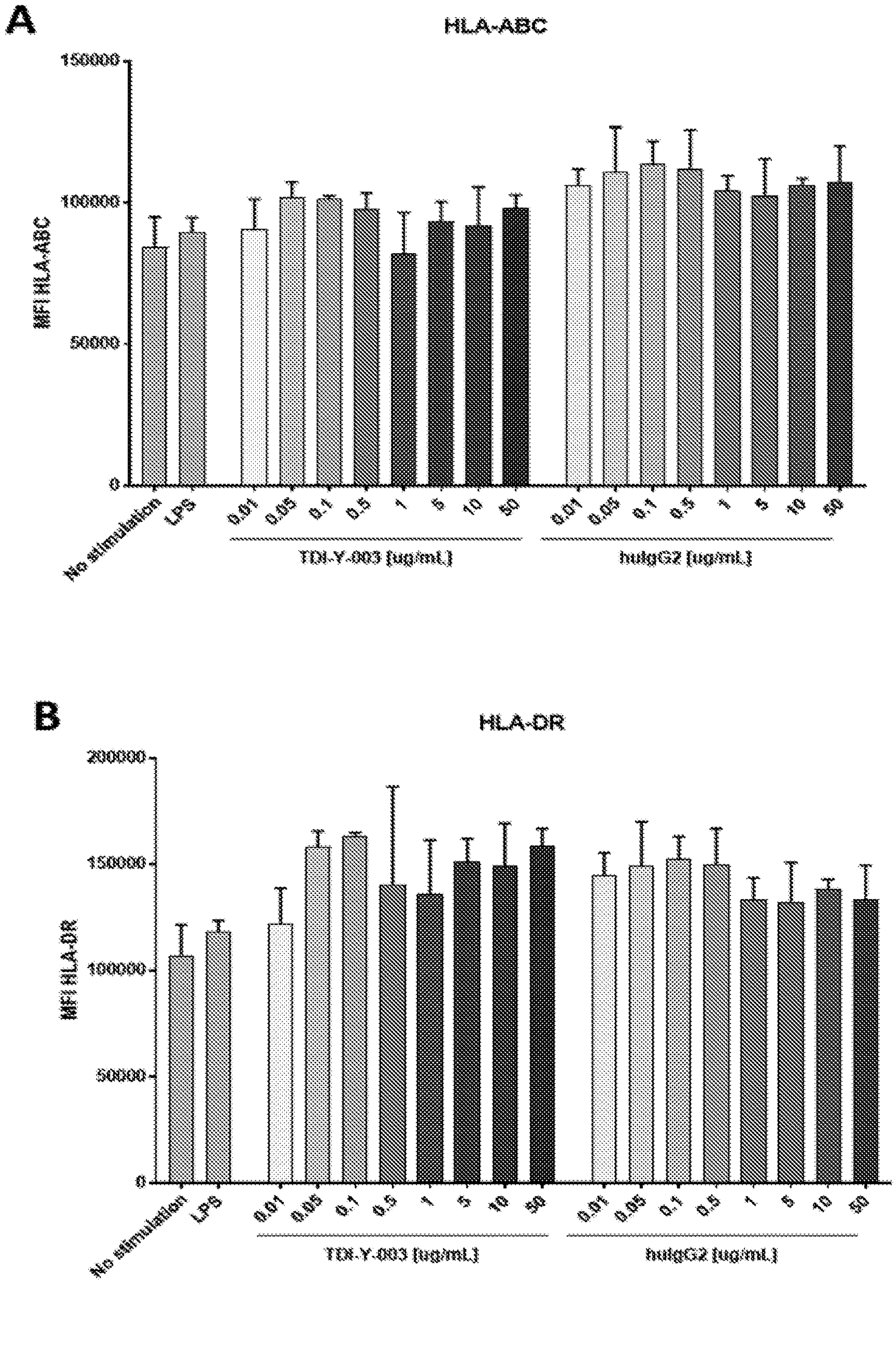
Figure 14:
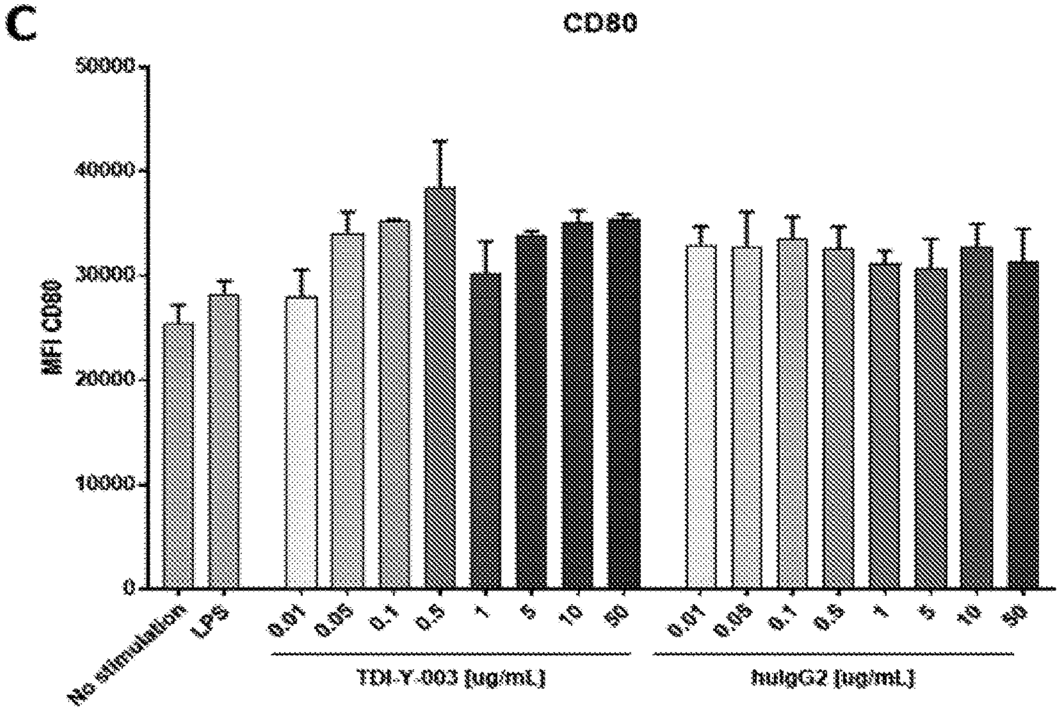
Figure 14:
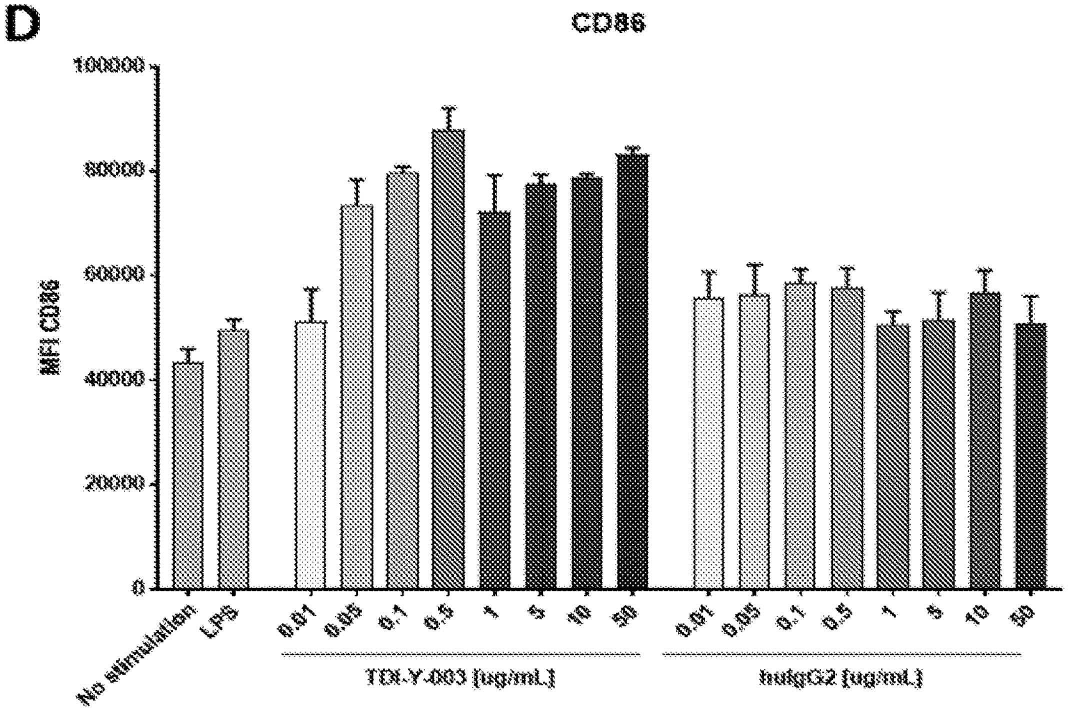

FIG. 14 A-D. Activation of Raji B-lymphoblastic cells by TDI-Y-003. Raji cells were stimulated with increasing doses of TDI-Y-003 or human IgG2 isotype control. Expression of the APC activation markers HLA-ABC (FIG. 14 A), HLA-DR (FIG. 14 B), CD80 (FIG. 14 C), and CD86 (FIG. 14 D) was determined by flow cytometry.

Figure 15:
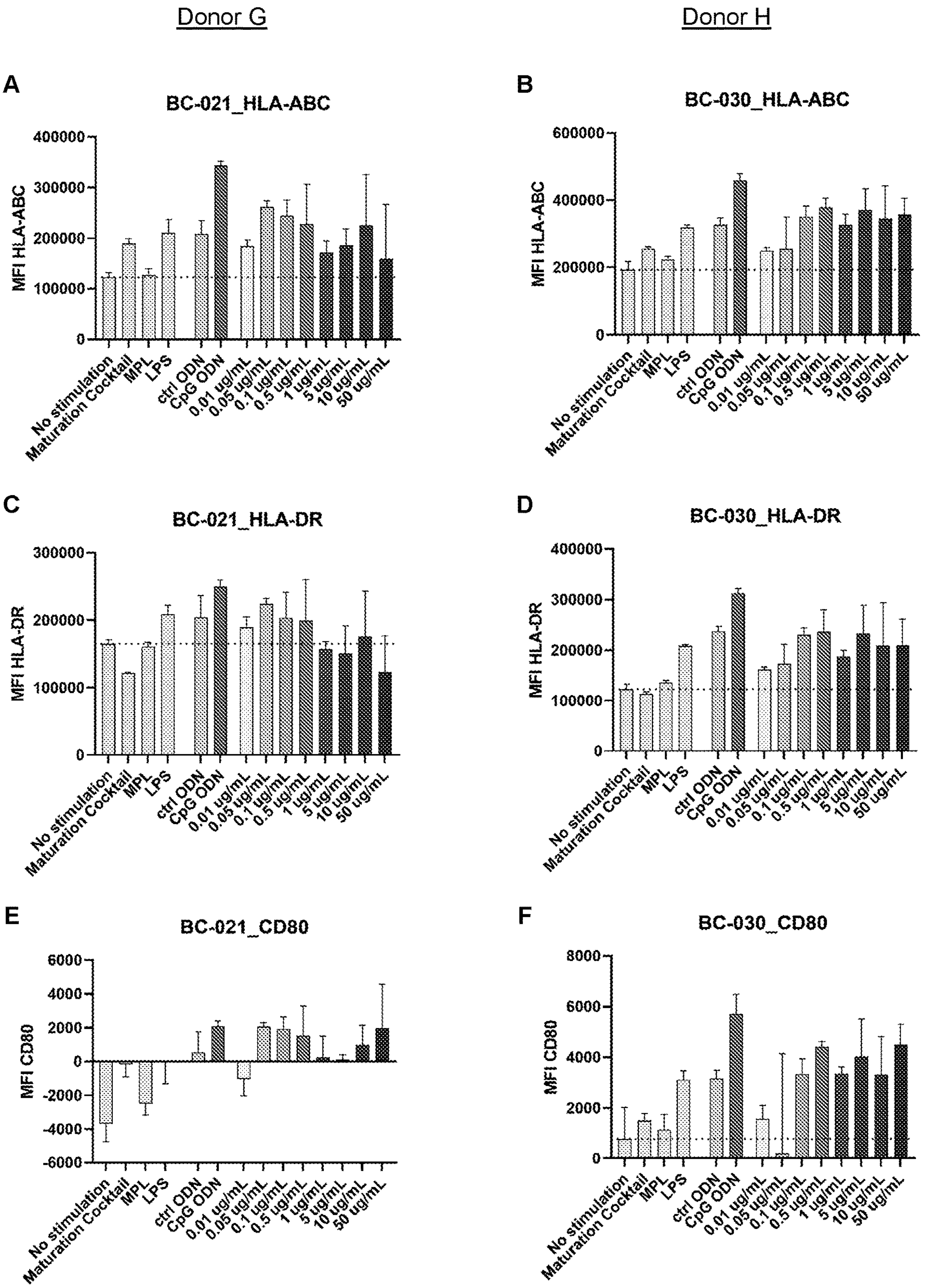
Figure 15:
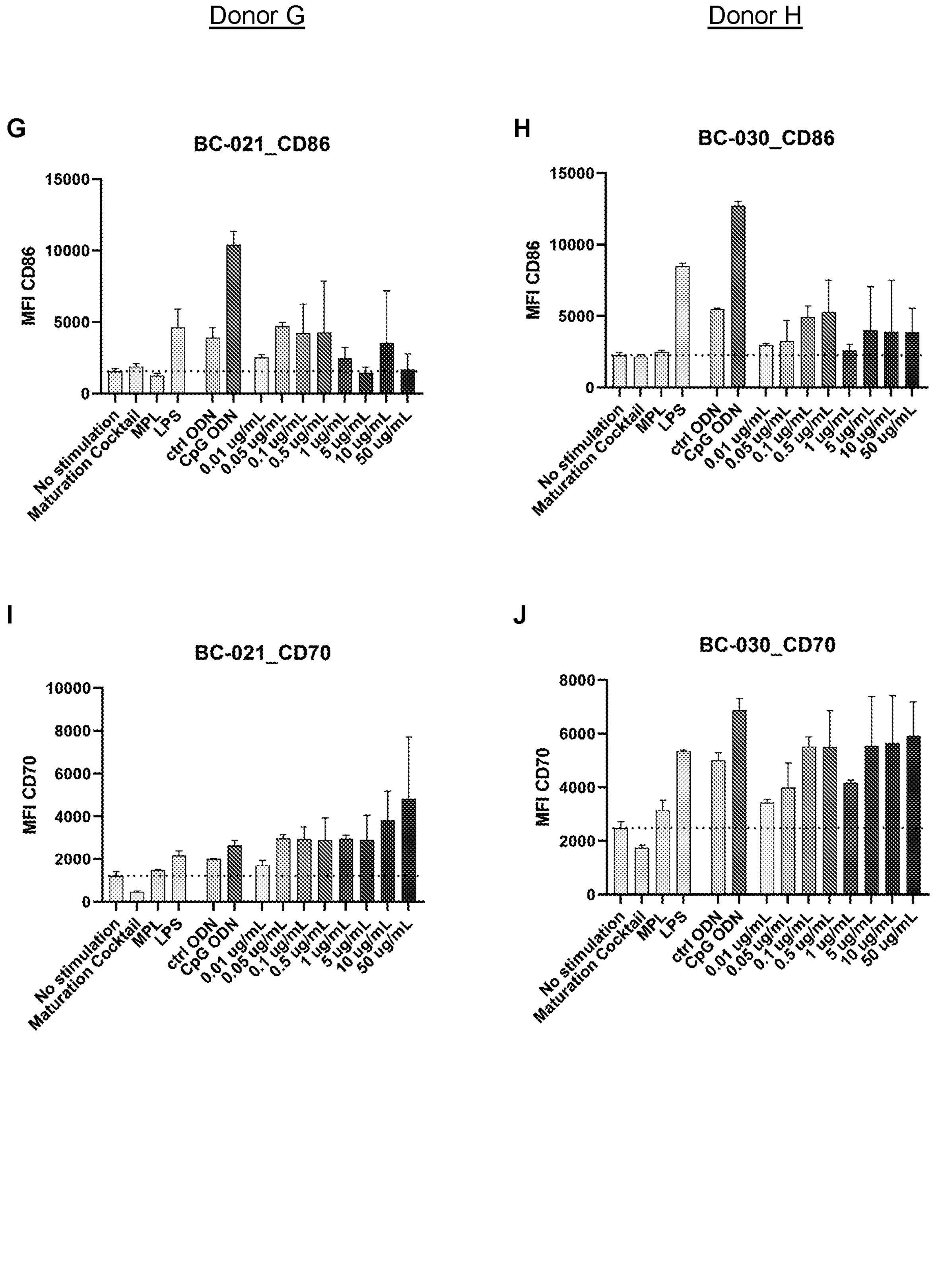

FIG. 15 A-J. Activation by TDI-Y-003 of primary human B cells from 2 different donors. B cells were stimulated with increasing doses of TDI-Y-003. Negative (no stimulation) and positive (maturation cocktail, LPS, MPL) assay controls are shown. CpG ODN, a short oligonucleotide that has been shown to activate B cells via TLR9 agonism, and a control oligonucleotide ("Ctrl ODN") are also included. Expression of the APC activation markers HLA-ABC (FIG. 15 A, B), HLA-DR (FIG. 15 C, D), CD80 (FIG. 15 E, F), CD86 (FIG. 15 G, H), and CD70 (FIG. 15 I, J) was determined for B cells from Donor G and H, respectively, by flow cytometry.

Figure 16:
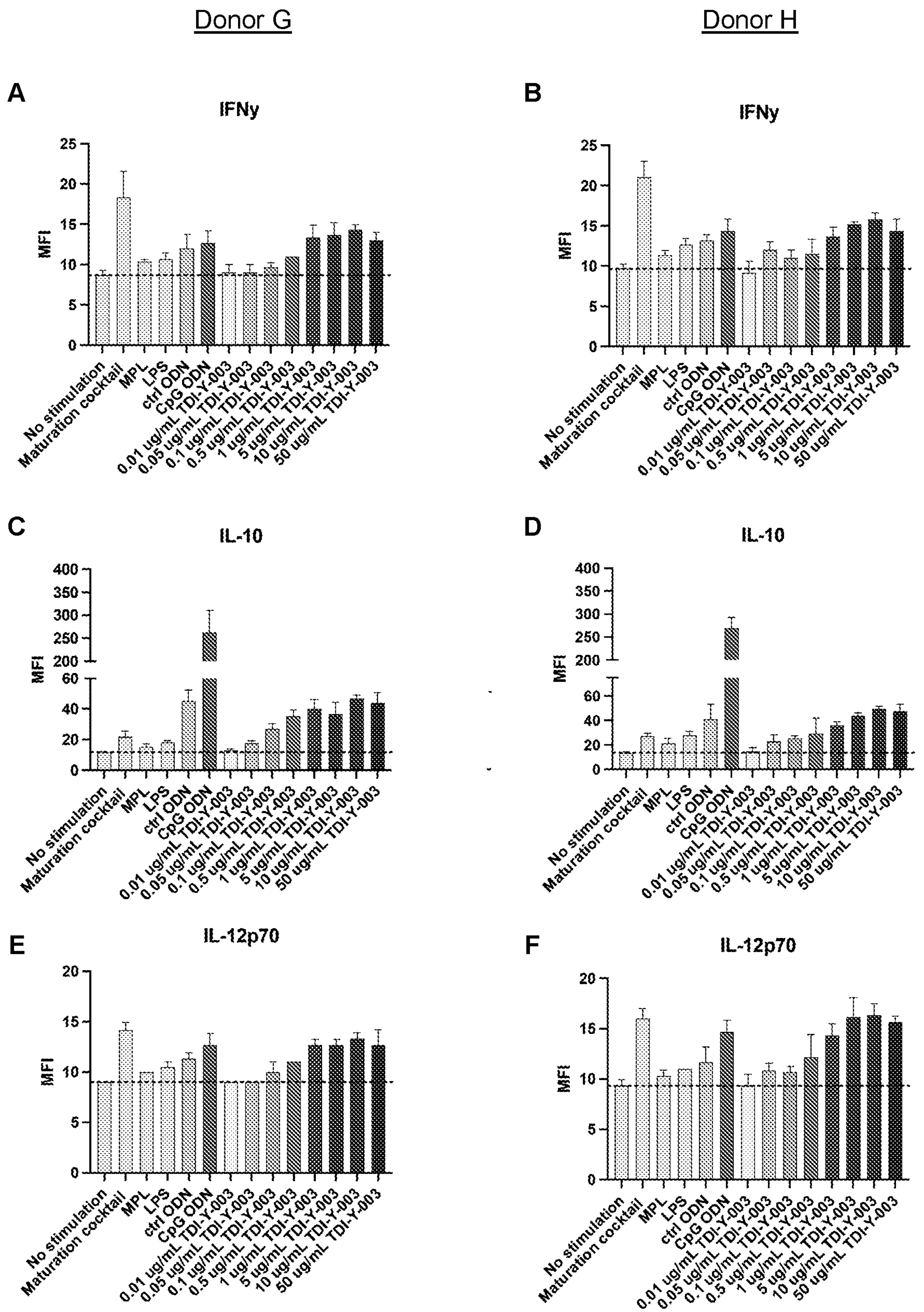
Figure 16:
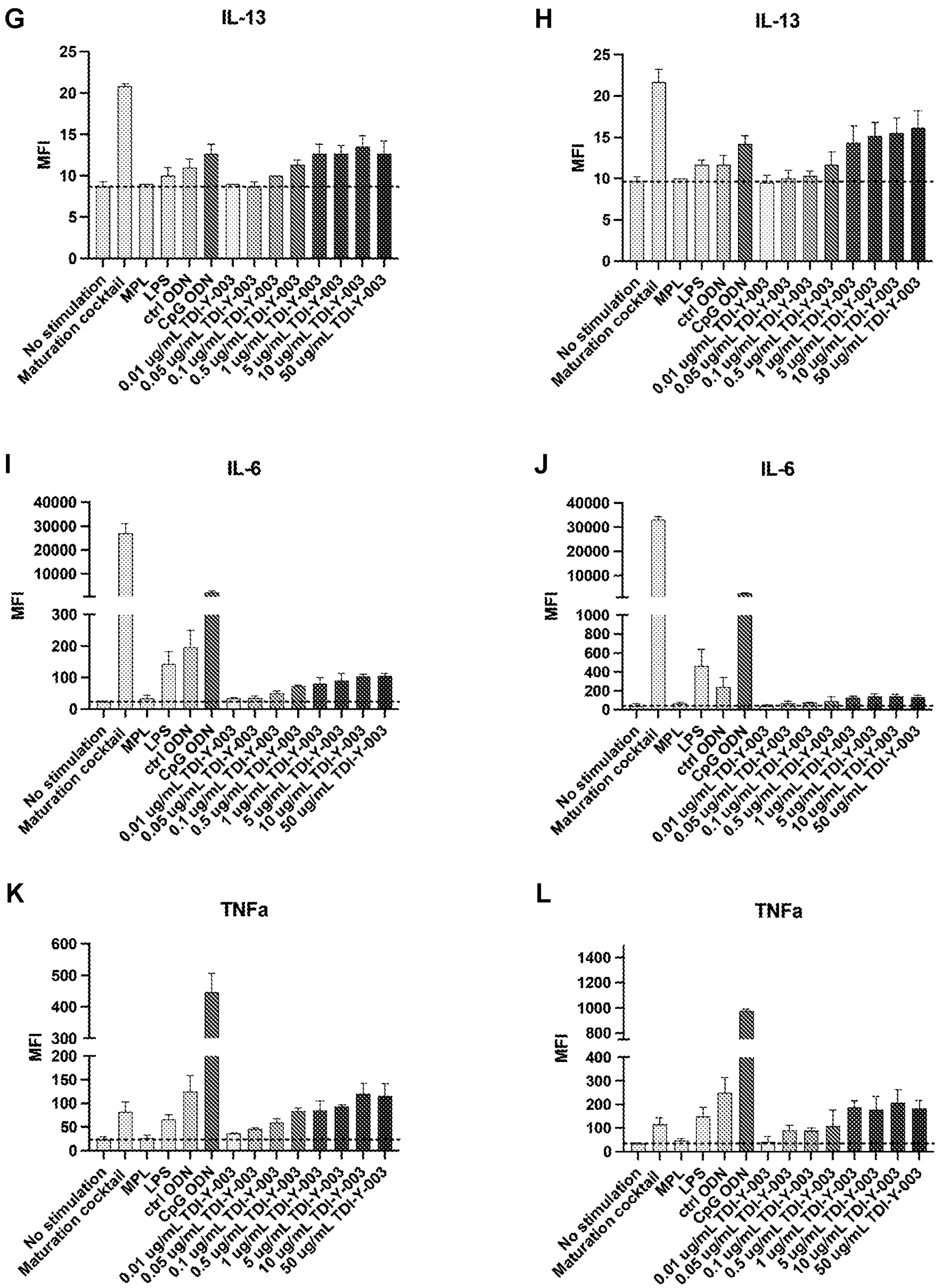

FIG. 16 A-L. Activation by TDI-Y-003 of primary human B cells from 2 different donors. B cells were stimulated with increasing doses of TDI-Y-003. Negative (no stimulation) and positive (maturation cocktail, LPS, MPL) assay controls are shown. CpG ODN and a control oligonucleotide ("Ctrl ODN") are also included. Secretion of cytokines interferon gamma (IFNγ) (FIG. 16 A, B), IL-10 (FIG. 16 C, D), IL-12p70 (FIG. 16 E, F), IL-13 (FIG. 16 G, H), IL-6 (FIG. 16 I, J), and TNFα (FIG. 16 K, L) was determined for B cells from Donors G and H, respectively, by multiplex cytokine assay (Luminex).

Figure 17:
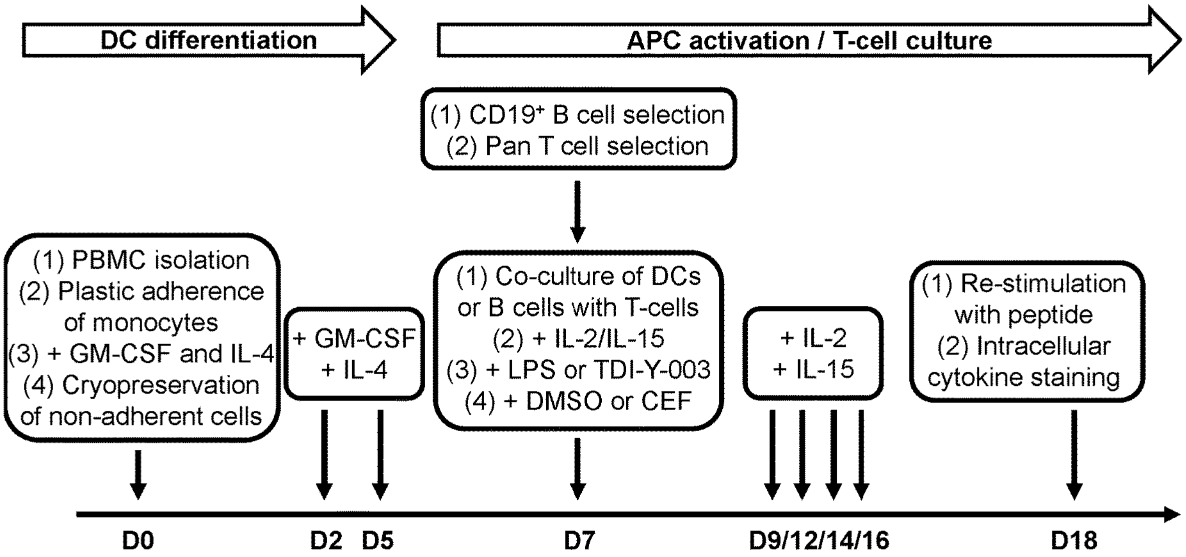

FIG. 17. Cell processing and stimulation schedule. Dendritic cells were differentiated from PBMCs as previously described. Dendritic cells or B cells were co-cultured with autologous T cells in the presence of IL-2 and IL-15, and stimulated for 48 hours with LPS or TDI-Y-003 and viral peptides (CEF) or DMSO vehicle control.

Figure 18:
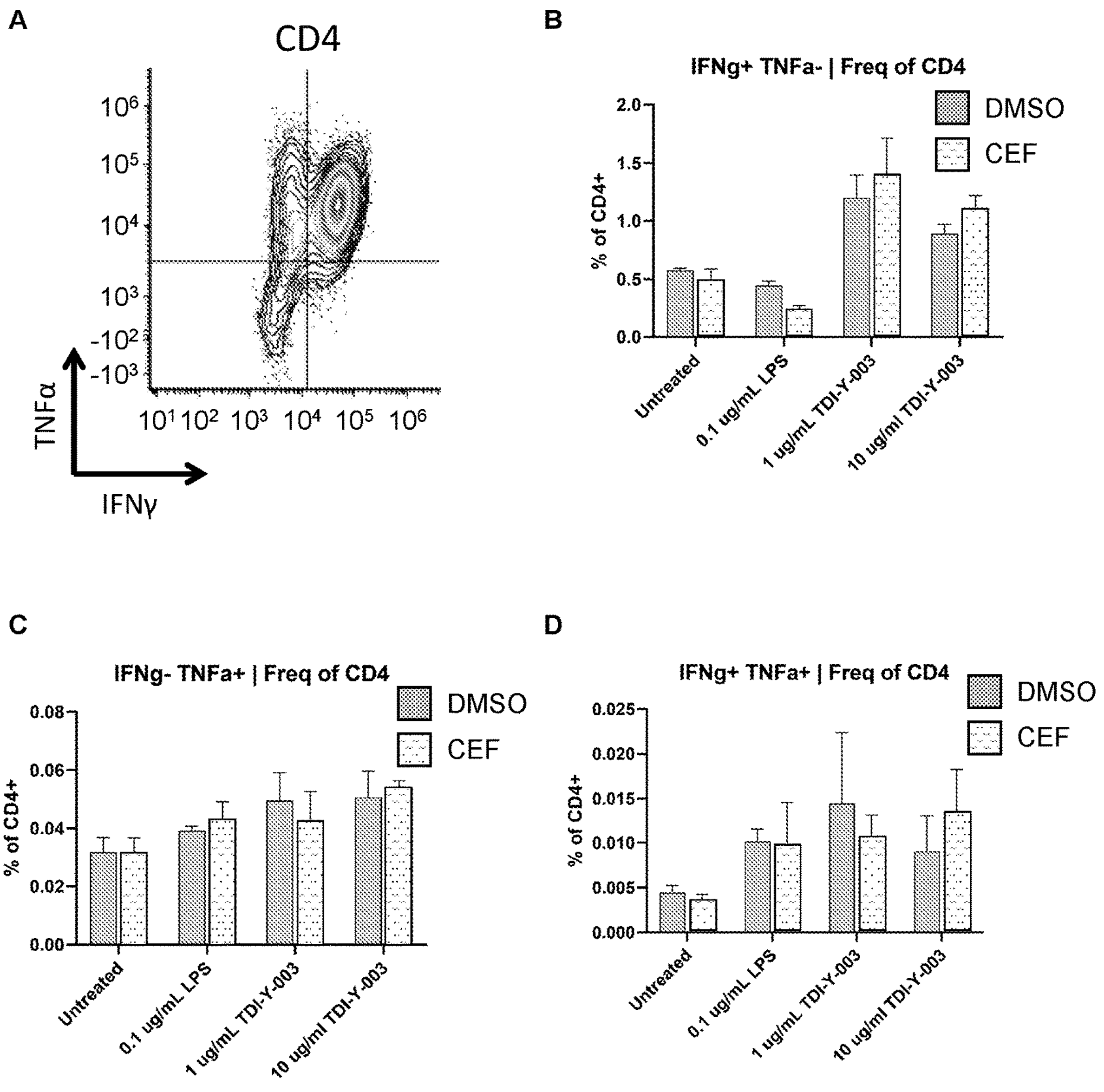
Figure 18:
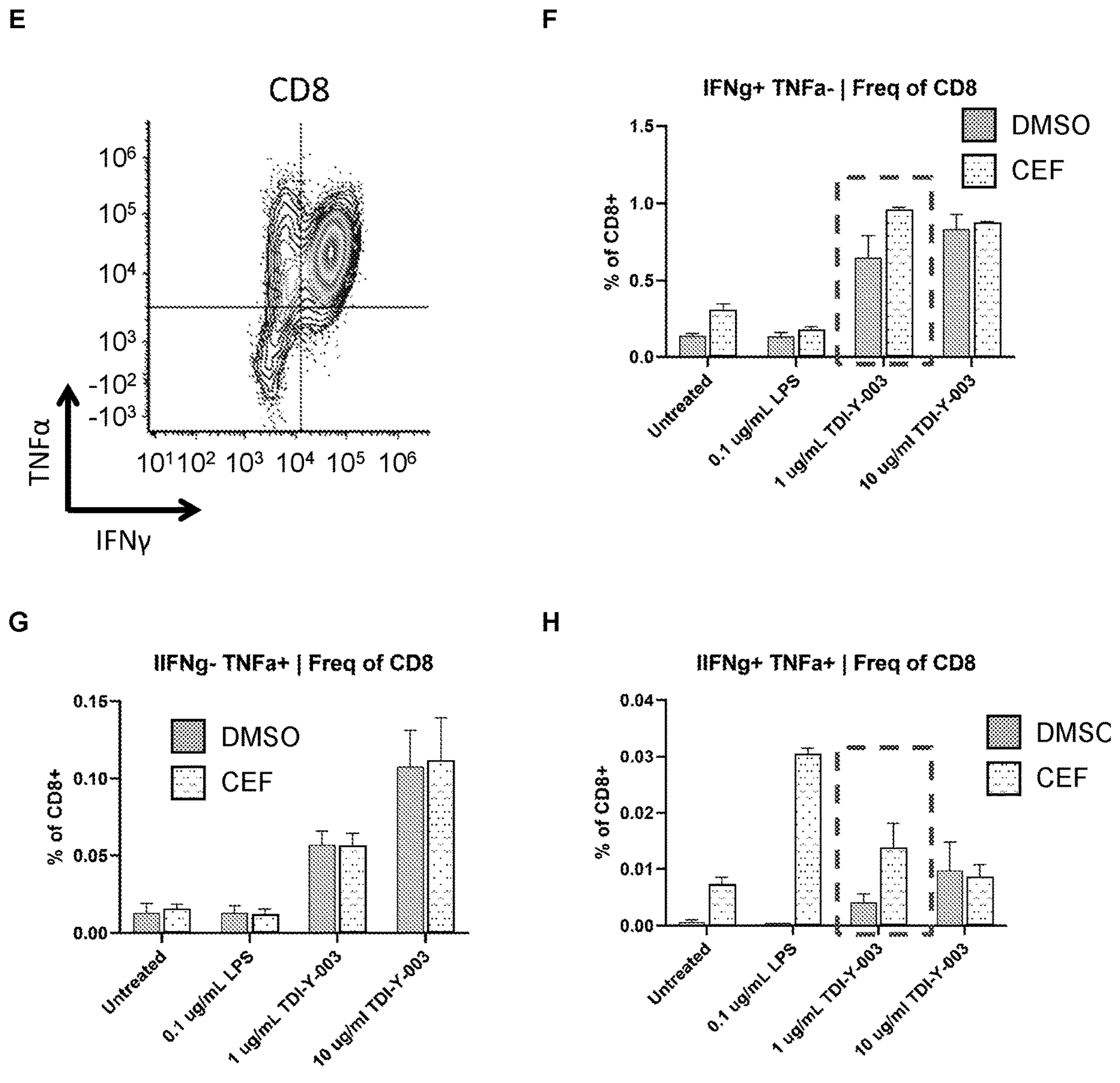

FIG. 18 A-H. Activation of T cells in the presence of dendritic cells stimulated by TDI-Y-003. Dendritic cells were stimulated with TDI-Y-003 (1 μg/mL or 10 μg/mL) or LPS (0.1 μg/mL), with DMSO or CEF. Flow cytometry data on CD4+ T cells is shown in FIGS. 18 A-D, and data on CD8+ T cells is shown in FIGS. 18 E-H. Exemplary gating strategies for identification of IFNγ+ and TNFα+ cells are shown in FIGS. 18 A and E. Frequencies of IFNγ+ TNFα− cells are shown in FIGS. 18 B and F, frequencies of IFNγ− TNFα+ cells are shown in FIGS. 18 C and G, and frequencies of IFNγ+ TNFα+ cells are shown in FIGS. 18 D and H.

Figure 19:
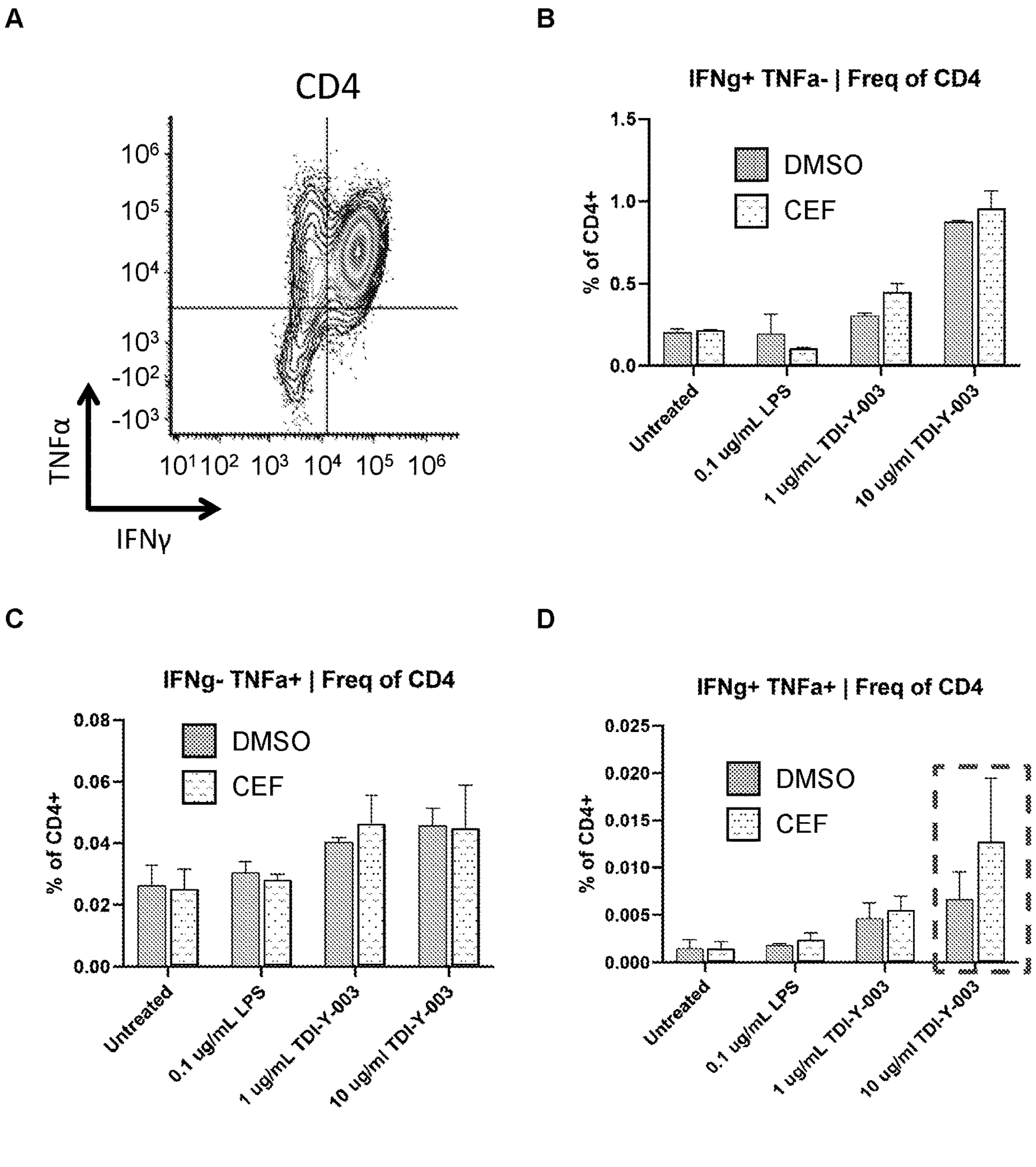
Figure 19:
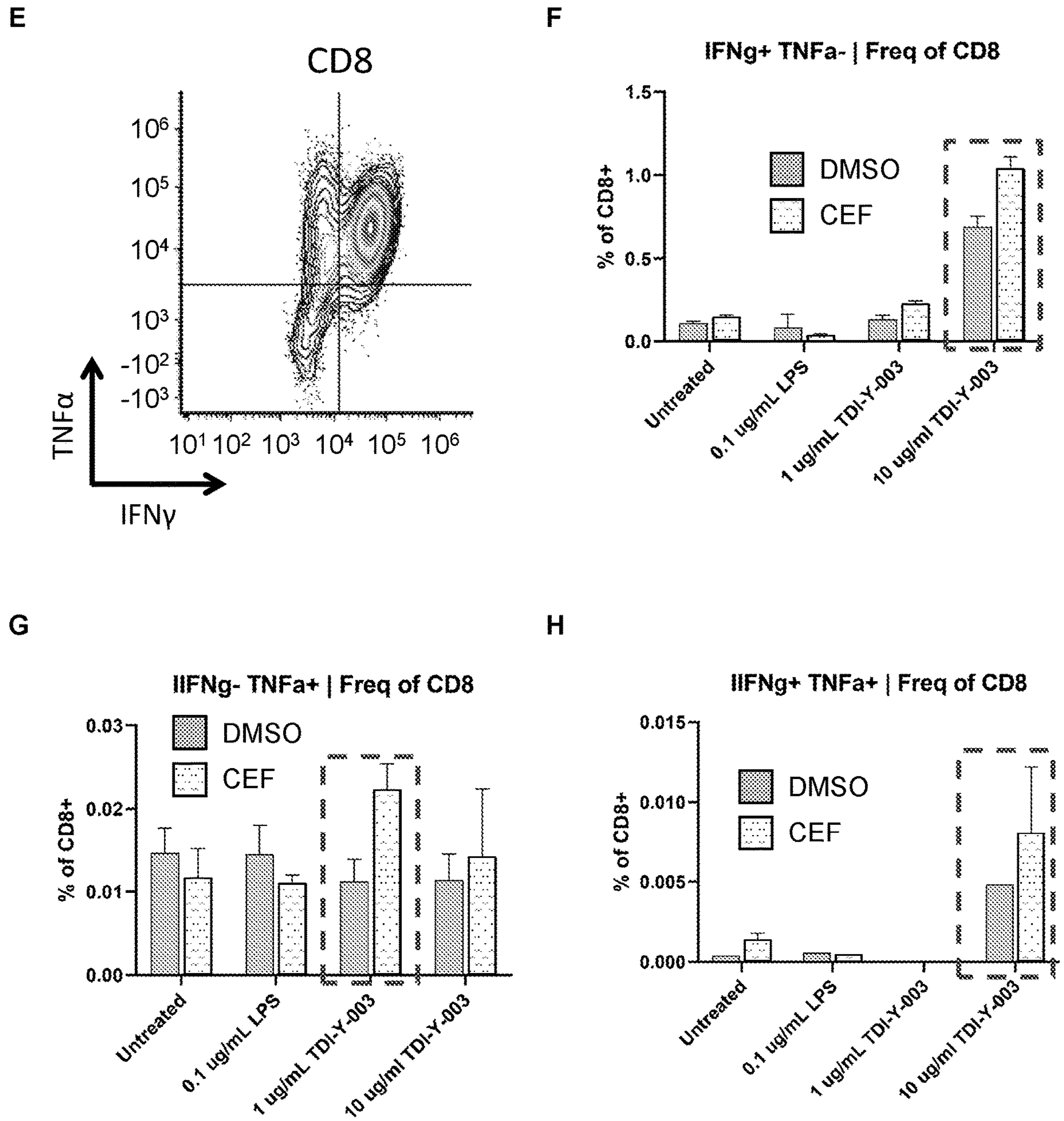

FIG. 19 A-H. Activation of T cells in the presence of B cells stimulated by TDI-Y-003. B cells were stimulated with TDI-Y-003 (1 μg/mL or 10 μg/mL) or LPS (0.1 μg/mL), with DMSO or CEF. Flow cytometry data on CD4+ T cells is shown in FIGS. 19 A-D, and data on CD8+ T cells is shown in FIGS. 19 E-H. Exemplary gating strategies for identification of IFNγ+ and TNFα+ cells are shown in FIGS. 19 A and E. Frequencies of IFNγ+ TNFα− cells are shown in FIGS. 19 B and F, frequencies of IFNγ− TNFα+ cells are shown in FIGS. 19 C and G, and frequencies of IFNγ+ TNFα+ cells are shown in FIGS. 19 D and H.

Figure 20:
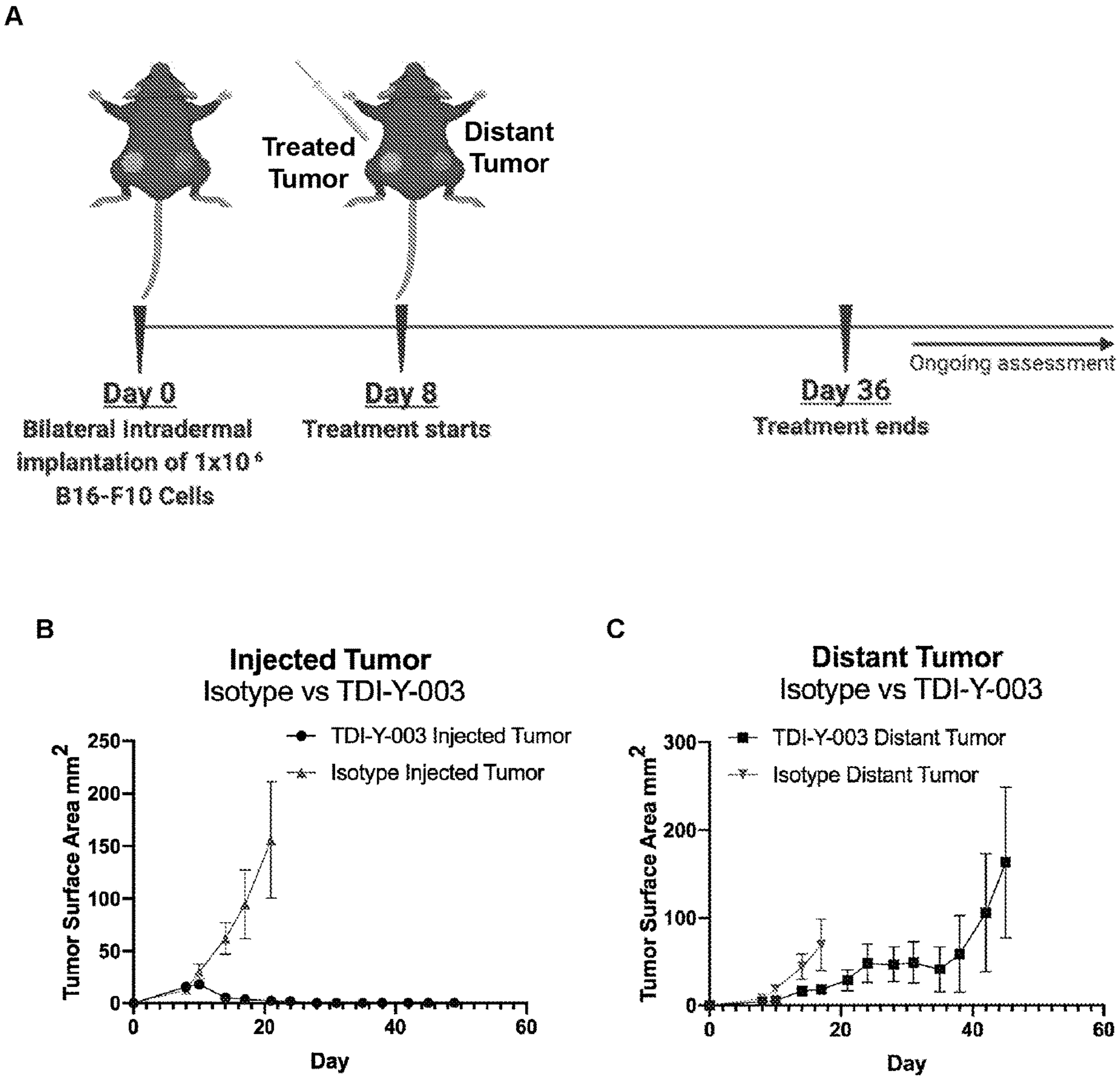

FIG. 20 A-C. Treatment schedule and tumor progression over time after treatment therapy. FIG. 20 A shows the mouse tumor model used and the treatment schedule. Intratumoral biweekly treatments, with TDI-Y-003 or human IgG2 isotype, were started once bilateral tumors were established (day 8); treatment was continued for 4 weeks. Injected tumor growth and distant tumor growth is shown in the graphs in FIG. 20 B and FIG. 20 C, respectively. Data points from the isotype control treatment are shown with triangles. Data points from TDI-Y-003 treatment are shown with circles (injected tumor) or squares (distant tumor). 5-8 mice were used per group.

Figure 21:
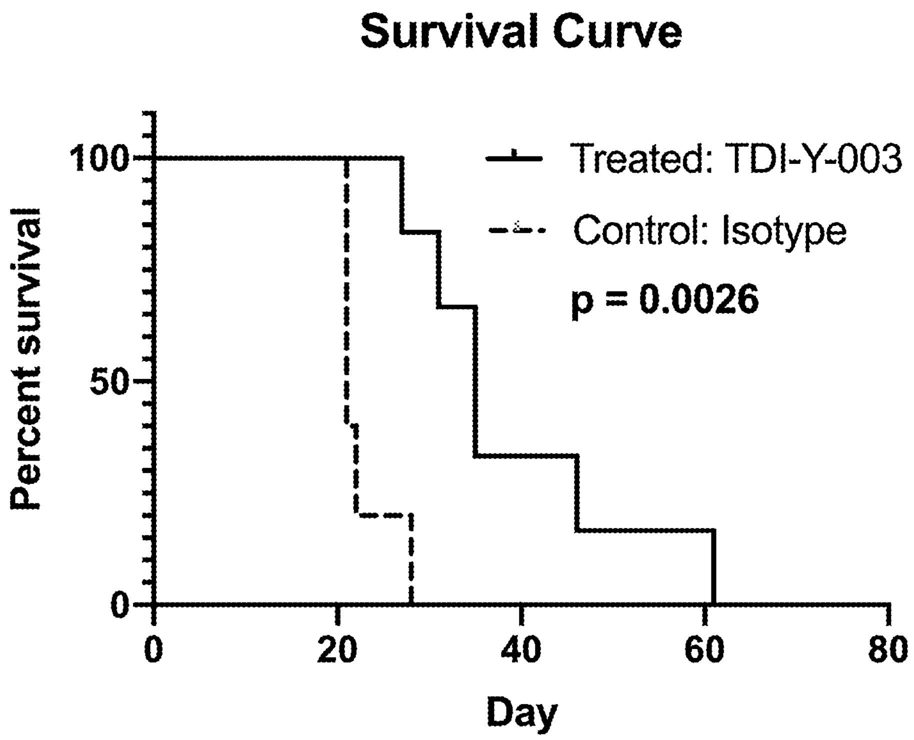

FIG. 21. Kaplan-Meier Curves comparing the survival of hCD40 agonist TDI-Y-003 and isotype control groups. Log-rank (Mantel-Cox) test was used.

Figure 22:
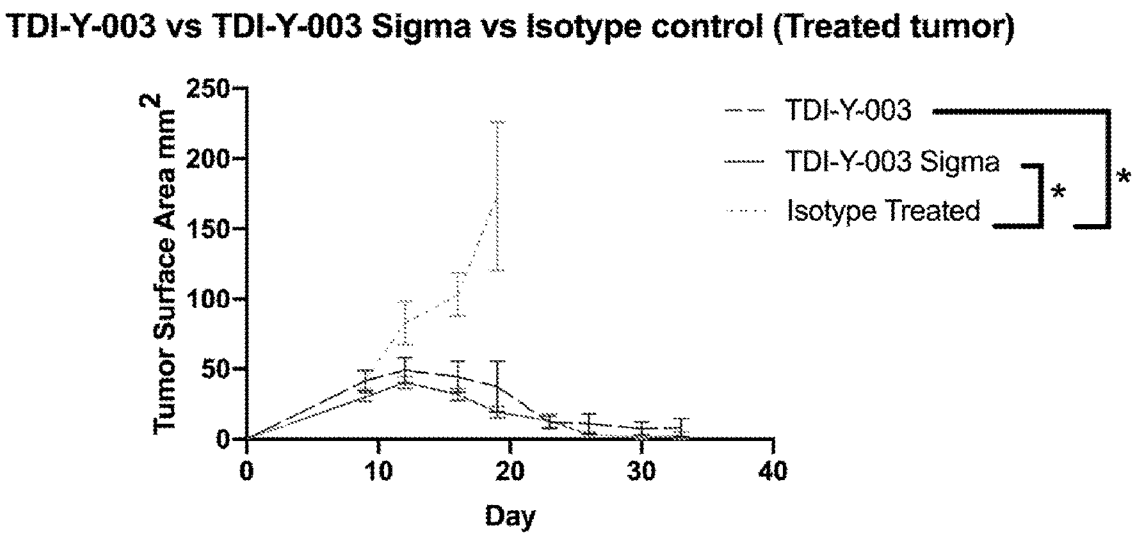
Figure 22:
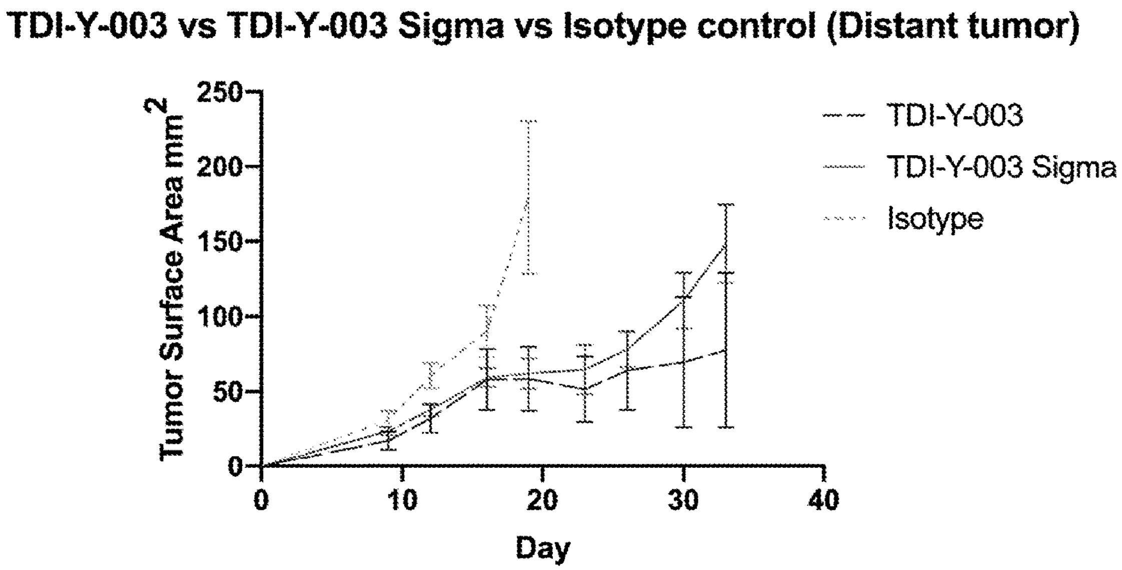

FIG. 22 A-B. Intratumoral biweekly treatments with TDI-Y-003, TDI-Y-003 hIgG26, or human IgG2 isotype were started once bilateral tumors were established (day 8) and continued for 4 weeks. Injected tumor growth (FIG. 22 A) and distant tumor growth (FIG. 22 B) were assessed. 5-8 mice were used per group.

Figure 23:
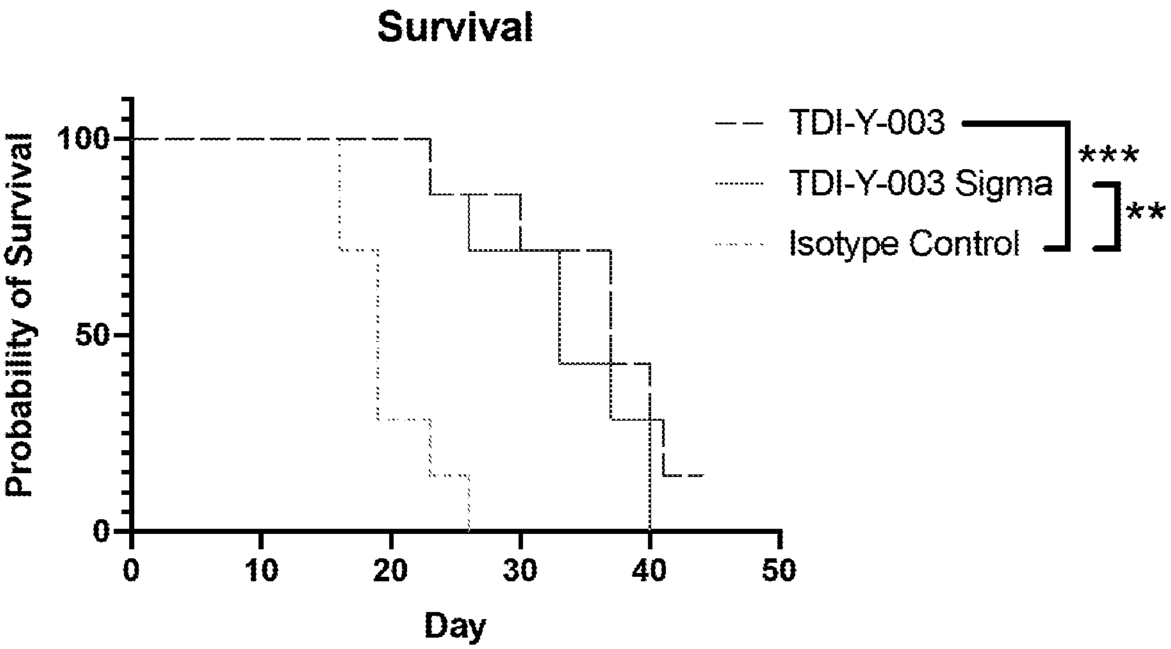

FIG. 23. Kaplan-Meier Curves comparing the survival of mice treated with TDI-Y-003, TDI-Y-003 hIgG26, or human IgG2 isotype. Log-rank (Mantel-Cox) test was used.

Figure 24:
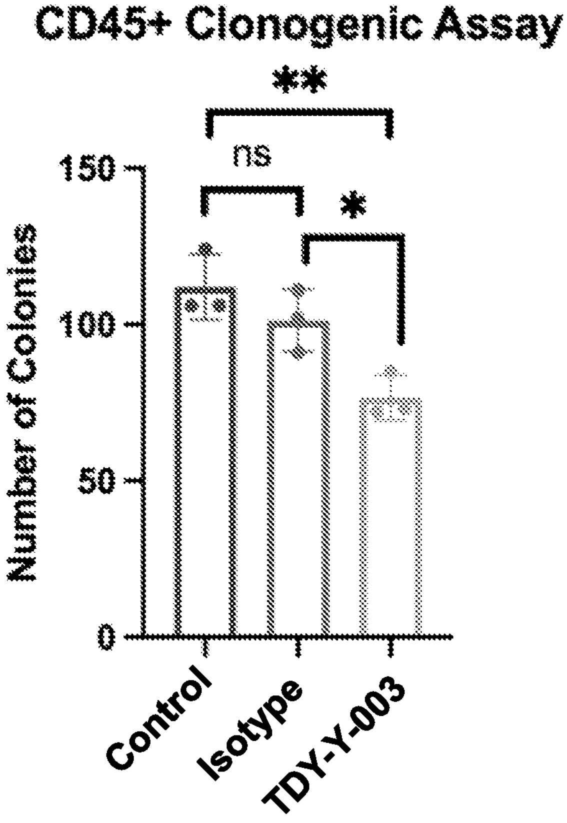

FIG. 24. CD45+ clonogenic assay of bilateral melanoma tumors in C57BL/6 transgenic mice treated with TDI-Y-003 or human IgG2 isotype. Tumor cells were obtained from 3 to 4 mice per group. Number of tumor-cell colonies are shown for tumors from control mice (no treatment), mice injected with the isotype, and mice injected with TDI-Y-003.

DETAILED DESCRIPTION

Some of the embodiments of the present invention are described in the "Summary of the Invention," "Examples," "Brief Description of the Figures," and "Figures" sections of this patent disclosure. This Detailed Description section provides certain additional embodiments and certain additional description and details relating to embodiments described elsewhere herein, and is intended to be read in conjunction with all other sections of the present patent disclosure.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Ausubel et al. eds. (2015) *Current Protocols in Molecular Biology* (John Wiley and Sons); Greenfield, ed. (2013) *Antibodies: A Laboratory Manual* (2nd ed., Cold Spring Harbor Press); Green and Sambrook, eds. (2012), *Molecular Cloning: A Laboratory*

*Manual* (4th ed., Cold Spring Harbor Laboratory Press); Krebs et al., eds. (2012) Lewin's Genes XI (11th ed., Jones & Bartlett Learning); Freshney (2010) *Culture Of Animal Cells* (6th ed., Wiley); Weir and Blackwell, eds., (1996) *Handbook Of Experimental Immunology, Volumes I-IV* (5th ed., Wiley-Blackwell); Borrebaeck, ed. (1995) *Antibody Engineering* (2nd ed., Oxford Univ. Press); Glover and Hames, eds., (1995) *DNA Cloning: A Practical Approach*, Volumes I and II (2nd ed., IRL Press); Rees et al., eds. (1993) *Protein Engineering: A Practical Approach* (1st ed., IRL Press); Mayer and Walker, eds. (1987) *Immunochemical Methods In Cell And Molecular Biology* (Academic Press, London); Nisonoff (1984) *Introduction to Molecular Immunology* (2nd ed., Sinauer Associates, Inc.); and Steward (1984) *Antibodies: Their Structure and Function* (1st ed., Springer Netherlands).

In order that the present invention can be more readily understood, certain terms are defined herein. Additional definitions are set forth throughout the disclosure. Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology* (2d ed. P-S. Juo, 2002) can provide one of skill with general definitions of some terms used herein.

I. Definitions & Abbreviations

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone).

Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Systéme International de Unites (SI) accepted form. Numeric ranges provided herein are inclusive of the numbers defining the range.

Where a numeric term is preceded by "about" or "approximately," the term includes the stated number and values ±10% of the stated number.

Numbers in parentheses or superscript following text in this patent disclosure refer to the numbered references provided in the "Reference List" section of this patent disclosure.

Wherever embodiments are described with the language "comprising," otherwise analogous embodiments described in terms of "consisting of" and/or "consisting essentially of" are included.

Amino acids are referred to herein by their commonly known three-letter symbols or by the one-letter symbols recommended by the IUPAC-IUB Biochemical Nomenclature Commission. Nucleotides, likewise, are referred to by their commonly accepted single-letter codes.

The abbreviation "CDR" refers to a complementary determining region—for example of an antibody or other CD40 binding molecule as described herein. Typically, the variable domains of both the heavy and light chains of antibodies comprise three hypervariable CDRs located within relatively conserved framework regions (FR). In general, the heavy and light chains of the variable domains of antibodies comprise, from N-terminal to C-terminal, FR1, CDR1, FR2, CDR2, FR3, CDR3 and FR4 regions. There are several different methodologies by which the assignment of amino acids in a variable domain to each of these FR and CDR regions can be performed. These include the "Kabat" method (described in Kabat, et al.; National Institutes of Health, Bethesda, Md.; 5.sup.th ed.; NIH Publ. No. 91-3242 (1991); Kabat (1978) Adv. Prot. Chem. 32:1-75; Kabat, et al., (1977) J. Biol. Chem. 252:6609-6616, the "Chothia" method (described by Chothia, et al., (1987) J Mol. Biol. 196:901-917 and Chothia, et al., (1989) Nature 342:878-883) and the "IMGT" ((ImMuno GeneTics) method (described by Lefranc et al., 2003, Dev Comp Immunol 27: 55-77). There can be slight differences in the boundaries of the various FR and CDR regions, and thus slight differences in the precise locations and amino acid sequences of the CDRs, depending on which of these methodologies is used.

The amino acid sequences described herein were analyzed using the IMGT methodology and the CDR sequences provided are those identified by the IMGT methodology. The IMGT (ImMunoGeneTics) numbering scheme is a standardized numbering system for all the protein sequences of the immunoglobulin superfamily, including variable domains from antibody light and heavy chains as well as T cell receptor chains from different species and counts residues continuously from 1 to 128 based on the germ-line V sequence alignment (see Giudicelli et al., Nucleic Acids Res. 25:206-11 (1997); Lefranc, Immunol Today 18:509 (1997); Lefranc et al., Dev Comp Immunol. 27:55-77 (2003)).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, *Science,* 239:1534-1536). In some instances, the Fv framework region (FW) residues of a human immunoglobulin are replaced with the corresponding residues in an antibody from a non-human species that has the desired specificity, affinity, and capability. The term "human antibody" means an antibody produced by a human or an antibody having an amino acid sequence corresponding to an antibody produced by a human made using any technique known in the art. The definition of a human antibody includes intact or full-length antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse) with the desired specificity, affinity, and capability while the constant regions are homologous to the sequences in antibodies derived from another (usually human) to avoid eliciting an immune response in that species.

"Binding affinity" generally refers to the strength of the sum-total of non-covalent interactions between a single binding site of a molecule (e.g., a CD40 binding molecule) and its binding partner (e.g., CD40). Unless indicated otherwise, as used herein, "binding affinity" refers to intrinsic binding affinity which reflects a 1:1 interaction between members of a binding pair (e.g., a CD40 binding molecule and CD40). The affinity of a molecule X for its partner Y can generally be represented by the dissociation constant (KD). Affinity can be measured by common methods known in the art, including those described herein. Low-affinity antibodies generally bind antigen slowly and tend to dissociate readily, whereas high-affinity antibodies generally bind antigen faster and tend to remain bound longer.

The affinity or avidity of an antibody for an antigen can be determined experimentally using any suitable method known in the art, e.g., flow cytometry, enzyme-linked immunosorbent assay (ELISA), or radioimmunoassay (RIA), or kinetics (e.g., KINEXA® or BIACORE™ or OCTET® analysis). Direct binding assays as well as competitive binding assay formats can be readily employed. (See, e.g., Berzofsky et al., "Antibody-Antigen Interactions," In Fundamental Immunology, Paul, W. E., ed., Raven Press: New York, N.Y. (1984); Kuby, Immunology, W. H. Freeman and Company: New York, N.Y. (1992)). The measured affinity of a particular interaction (e.g., antibody-antigen interaction) can vary if measured under different conditions (e.g., salt concentration, pH, temperature). Thus, measurements of affinity and other antigen-binding parameters (e.g., KD or Kd, Kon, Koff) are made with standardized solutions of antibody and antigen, and a standardized buffer, as known in the art.

"Potency" is normally expressed as an $IC_{50}$ or $EC_{50}$ value, in nM or pM, unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $EC_{50}$ is the median effective concentration of an antibody molecule. In functional assays, $EC_{50}$ is the concentration that induces a biological response that is 50% of its maximum biological response. In ligand-binding studies, $EC_{50}$ is the concentration that induces 50% of the maximal specific binding level. $IC_{50}$ and $EC_{50}$ values can be calculated by any number of means known in the art.

As used herein a "subject" is any individual for whom diagnosis, prognosis, or therapy is desired. In some embodiments the subjects are mammalian subjects, including humans, domestic animals, farm animals, sports animals, and zoo animals. In some embodiments the subjects are non-human primates. In some embodiments the subjects are murine subjects. In some embodiments the subjects are humans.

The term "pharmaceutical composition" refers to a preparation that is in such form as to permit the biological activity of the active agent (e.g., a CD40 binding molecule) to be effective and which contains no additional components that are unacceptably toxic to a subject to which the composition may be administered. Such compositions can be sterile.

Typically, such compositions comprise a pharmaceutically acceptable carrier. Examples of pharmaceutically acceptable carriers include, but are not limited to, physiological saline. In some embodiments pharmaceutical compositions can comprise one or more of: a buffer (e.g., acetate, phosphate, or citrate buffer), a surfactant (e.g., polysorbate), a stabilizing agent (e.g., human albumin), a preservative (e.g., benzyl alcohol), an absorption promoter to enhance bioavailability and/or other conventional solubilizing or dispersing agents.

The term "vector" means a construct for delivery of a nucleic acid molecule to a host cell. Examples of vectors include, but are not limited to, viruses, viral-derived vectors, naked DNA or RNA vectors, plasmid vectors, cosmid vectors, phage vectors, and the like. In some embodiments a vector may be an "expression vector" that is capable of delivering a nucleic acid molecule to a host cell and that also contains elements required for expression of the nucleic acid molecule in the host cell.

An "isolated" molecule is not within a living subject or cell and is typically in a form not found in nature. In some embodiments an isolated molecule may have been purified to a degree that it is not in a form in which it is found in nature. In some embodiments, a molecule that is isolated is substantially pure. In some embodiments, a molecule that is isolated has a purity of greater than 75%, or greater than 80%, or greater than 90%, or greater than 95%.

The terms "identical" or percent "identity" in the context of two or more nucleic acid sequences or amino acid sequences, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

Other terms are defined elsewhere in this patent disclosure, or else are used in accordance with their usual meaning in the art.

II. CD40 Binding Molecules

The acronym "CD40" refers to "Cluster of Differentiation 40." CD40 is a costimulatory protein found on antigen-presenting cells that is required for their activation. The CD40 protein, and the nucleotide sequences that encode it, are well known in the art. The present invention provides CD40 binding molecules that specifically bind to and activate/agonize CD40.

The CD40 binding molecules of the present invention include, but are not limited to, those referred to herein as TDS-Y-003, Hu10F12 and Hu10FG2 (N103D)—each of which are humanized antibodies comprising a heavy chain and a light chain. The CD40 binding molecules of the present invention also include three different humanized variants of Hu10F12—each having identical CDRs but differences in their variable domain amino acid sequences outside of the CDR regions. Amino acid sequences comprising the variable regions of TDI-Y-003, three different humanized variants of Hu10F12, and Hu10F12 (N103D) are provided in Table A, below. The amino acid sequences provided in Table A were analyzed using the IMGT methodology, and the location and sequence of the CDR regions shown in Table A are those identified using the IMGT methodology.

TABLE A

TDI-Y-003 and Hu10F12 Heavy & Light Chain Sequences

| Antibody Name | Chain | SEQ ID NO. | Amino Acid Sequence |
|---|---|---|---|
| TDI-Y-003 | Heavy chain | SEQ ID NO. 1 | **QVQLQESGPGLVKPSETLSLTCTVSGFSLTTYGLHWI**<br>**RQPPGKGLEWIGVIWRGGNTDYNPSLKSRVTISKDTS**<br>**KNQVSLKLSSVTAADTAVYYCAKNSYYG*Q*GGHAMD**<br>**YWGQGTLVTVSS**ASTKGPSVFPLAPCSRSTSESTAAL<br>GCLVKDYFPEPVTVSWNSGALTSGVHTFPAVLQSSGL<br>YSLSSVVTVPSSNFGTQTYTCNVDHKPSNTKVDKTVE<br>RKCCVECPPCPAPPVAGPSVFLFPPKPKDTLMISRTP<br>EVTCVVVDVSHEDPEVQFNWYVDGVEVHNAKTKPRE<br>EQFNSTFRVVSVLTVVHQDWLNGKEYKCKVSNKGLP<br>APIEKTISKTKGQPREPQVYTLPPSREEMTKNQVSLTC<br>LVKGFYPSDIAVEWESNGQPENNYKTTPPMLDSDGS<br>FFLYSKLTVDKSRWQQGNVFSCSVMHEALHNHYTQK<br>SLSLSPG<br>Bold = variable domain<br>Bold & underlined = CDRs<br>Red/italicized = position 103 with N103Q mutation<br>Non-bold = constant domain |
| TDI-Y-003 | Light chain | SEQ ID NO. 2 | **DIVMTQSPDSLAVSLGERATINCKSSQSLLHSFNQKN**<br>**YLAWYQQKPGQPPKLLIYFTSTRESGVPDRFSGSGS**<br>**GTDFTLTISSLQAEDVAVYYCQQHYTTPFTFGQGTKL**<br>**EIK**RTVAAPSVFIFPPSDEQLKSGTASVVCLLNNFYPR<br>EAKVQWKVDNALQSGNSQESVTEQDSKDSTYSLSST<br>LTLSKADYEKHKVYACEVTHQGLSSPVTKSFNRGEC<br>Bold = variable domain<br>Bold & underlined = CDRs<br>Non-bold = constant domain |
| Hu10F12 Humanized Variant 1 | Heavy chain | SEQ ID NO. 3 | **QVQLQESGPGLVKPSETLSLTCTVSGFSLTTYGLHWI**<br>**RQPPGKGLEWIGVIWRGGNTNYNPSLKSRVTISVDTS**<br>**KNQFSLKLSSVTAADTAVYYCAKNSYYG*N*GGHAMD**<br>**YWGQGTLVTVSS**<br>Bold = variable domain<br>Bold & underlined = CDRs<br>Red/italicized = position 103 |
| Hu10F12 Humanized Variant 1 | Light chain | SEQ ID NO. 4 | **DIVMTQSPDSLAVSLGERATINCKSSQSLLHSFNQKN**<br>**YLAWYQQKPGQPPKLLIYFTSTRESGVPDRFSGSGS**<br>**GTDFTLTISSLQAEDVAVYYCQQHYTTPFTFGQGTKL**<br>**EIK**<br>Bold = variable domain<br>Bold & underlined = CDRs |
| Hu10F12 Humanized Variant 2 | Heavy chain | SEQ ID NO. 5 | **QVQLQESGPGLVKPSETLSLTCTVSGFSLTTYGLHWI**<br>**RQPPGKGLEWIGVIWRGGNTDYNPSLKSRVTISKDTS**<br>**KNQVSLKLSSVTAADTAVYYCAKNSYYG*N*GGHAMD**<br>**YWGQGTLVTVSS**<br>Bold = variable domain<br>Bold & underlined = CDRs<br>Red/italicized = position 103 |
| Hu10F12 Humanized Variant 2 | Light chain | SEQ ID NO. 6 | **DIVMTQSPDSLAVSLGERATINCKSSQSLLHSFNQKN**<br>**YLAWYQQKPGQPPKLLIYFTSTRESGVPDRFLGSGS**<br>**GTDFTLTISSLQAEDVAVYFCQQHYTTPFTFGQGTKL**<br>**EIK**<br>Bold = variable domain<br>Bold & underlined = CDRs |
| Hu10F12 Humanized Variant 3 | Heavy chain | SEQ ID NO. 7 | **QVQLVESGGGVVQPGRSLRLSCAASGFSLTTYGMH**<br>**WVRQAPGKGLEWVAVIWRGGNTDYNADSVKGRFTI**<br>**SRDNSKNTLYLQMNSLRAEDTAVYYCAKNSYYG*N*G**<br>**GHAMDYWGQGTLVTVSS**<br>Bold = variable domain<br>Bold & underlined = CDRs<br>Red/italicized = position 103 |
| Hu10F12 Humanized Variant 3 | Light | SEQ ID NO. 8 | **DIVMTQVPVSLAVSLGERATINCKSSQSLLHSFNQKN**<br>**YLAWYQQKPGQSPKLLIYFTSTRESGVPDRFSGSGS**<br>**GTDFTLTISSLQAEDVAVYFCQQHYTTPFTFGQGTKL**<br>**EIK**<br>Bold = variable domain<br>Bold & underlined = CDRs |

TABLE A-continued

| TDI-Y-003 and Hu10F12 Heavy & Light Chain Sequences | | | |
|---|---|---|---|
| Antibody Name | Chain | SEQ ID NO. | Amino Acid Sequence |
| 10F12 Mouse | Heavy Chain | SEQ ID NO. 17 | **QVQLKQSGPGLVQPSQSLSITCTVSGFSLTTYGLHW VRQSPGKGLEWLGVIWRGGNTDYNAAFMSRLSITKD NSKSQVFFKMNSLQADDTAIYYCAKNSYYG*N*GGHA MDYWGQGTSVTVSS**<br>Bold = variable domain<br>Bold & underlined = CDRs<br>Red/italicized = position 103 |
| 10F12 Mouse | Light Chain | SEQ ID NO. 18 | **DIVMTQSPSSLAMSVGQKVTMSCKSSQSLLHSFNQK NYLAWYQQRPGQSPKLLIYFTSTRESGVPDRFLGSG SGTDFTLTISSVQAEDLADYFCQQHYTTPFT**FGSGTK **LEIK**<br>Bold = variable domain<br>Bold & underlined = CDRs |

In Table A, the amino acid sequences of the TDI-Y-003 heavy and light chains are presented in a human IgG2 format. However, one of skill in the art will recognize, as described elsewhere herein, that these sequences can be engineered to different immunoglobulin formats, and/or to produce antigen binding fragments and the like while retaining the key determinants for their CD40 binding and agonist activity—i.e., their CDRs. Similarly, in Table A the amino acid sequences of three different variants of the Hu10F12 heavy and light chain variable regions are presented. For these molecules, only the variable domain sequences are shown.

One of skill in the art will recognize that the specific full-length antibody sequences or full variable domain sequences provided herein can be engineered to contain various different constant regions and/or can be engineered to various different immunoglobulin formats, and/or can be engineered to produce antigen binding fragments and the like—as long as the molecules retain the key determinants for their CD40 binding and agonist activity—i.e., their CDRs.

Accordingly, in some embodiments the present invention provides CD40 binding molecules that comprise the CDR sequences of either TDI-Y-003, the 3 variants of Hu10F12 or Hu10F12 (N103D). The CDRs of these CD40 binding molecules are the same with the exception that they vary at the amino acid position in CDRH3 that corresponds to amino acid number 103 of SEQ ID NO. 1 (the position in CDRH3 that corresponds to amino acid number 103 of SEQ ID NO. can be readily determined by alignment of a given sequence to SEQ ID NO. 1 or to a portion of SEQ ID NO. 1). The amino acid sequences of the CDRs of TDI-Y-003, the 3 Hu10F12 variants and Hu10F12 (N103D), as determined using the IMGT methodology, are provided in Table B, below.

TABLE B

| CDR Sequences | | | | | | |
|---|---|---|---|---|---|---|
| Antibody | CDR H1 | CDR H2 | CDR H3 | CDR L1 | CDR L2 | CDR L3 |
| Hu10F12 | GFSLTTYG<br>SEQ ID NO. 9 | IWRGGNT<br>SEQ ID NO. 10 | AKNSYYG*N*GG<br>HAMDY<br>SEQ ID NO. 11 | QSLLHSFNQKN<br>Y<br>SEQ ID NO. 12 | FTS | QQHYTTPFT<br>SEQ<br>ID NO. 13 |
| Hu10F12<br>(N103D) | GFSLTTYG<br>SEQ ID NO. 9 | IWRGGNT<br>SEQ ID NO. 10 | AKNSYYG*D*GG<br>HAMDY<br>SEQ ID NO. 14 | QSLLHSFNQKN<br>Y<br>SEQ ID NO. 12 | FTS | QQHYTTPFT<br>SEQ ID NO. 13 |
| TDI-Y-003 | GFSLTTYG<br>SEQ ID NO. 9 | IWRGGNT<br>SEQ ID NO. 10 | AKNSYYG*Q*GG<br>HAMDY<br>SEQ ID NO. 15 | QSLLHSFNQKN<br>Y<br>SEQ ID NO. 12 | FTS | QQHYTTPFT<br>SEQ ID NO. 13 |
| 10F12<br>Mouse | GFSLTTYG<br>SEQ ID NO. 9 | IWRGGNT<br>SEQ ID NO. 10 | AKNSYYG*N*GG<br>HAMDY<br>SEQ ID NO. 11 | QSLLHSFNQKN<br>Y<br>SEQ ID NO. 12 | FTS | QQHYTTPFT<br>SEQ ID NO. 13 |
| | | | AKNSYYGXGG<br>HAMDY<br>SEQ ID NO. 16<br>Wherein "X" is A, R, N, D, E, Q, G, H, I, L, K, M, F, S, T, W, Y or V | | | |

The red/italicized text in Table B represents the location of the amino acid in CDR H3 that corresponds to amino acid residue 103 of SEQ ID NO. 1. This amino acid is an N in hu10F12 and in SEQ ID NO. 11, a D in Hu10F12 (N103D) and in SEQ ID NO. 14, and a Q in TDI-Y-003 and in SEQ ID NO. 11. In SEQ ID NO. 16 this amino acid is A, R, N, D, E, Q, G, H, I, L, K, M, F, S, T, W, Y or V.

Accordingly, in some embodiments, the present invention provides CD40 binding molecules that comprise:

(i) a heavy chain variable region comprising:
  a. a CDR H1 domain comprising SEQ ID NO. 9,
  b. a CDR H2 domain comprising SEQ ID NO. 10, and
  c. a CDR H3 domain comprising SEQ ID NO. 11 or SEQ ID NO. 14 or SEQ ID NO. 15, and
(ii) a light chain variable region comprising:
  a. a CDR L1 domain comprising SEQ ID NO. 12,
  b. a CDR L2 domain comprising the amino acid sequence FTS, and
  c. a CDR L3 domain comprising SEQ ID NO. 13,
    wherein such molecules bind to, and are agonists of, human CD40.

In some of such embodiments the CDR H3 domain in the CD40 binding molecule comprises SEQ ID NO. 11. In some such embodiments the CDR H3 domain in the CD40 binding molecule comprises SEQ ID NO. 14. In some such embodiments the CDR H3 domain in the CD40 binding molecule comprises SEQ ID NO. 15.

In some embodiments other amino acids are present at the position in CDR H3 that corresponds to amino acid residue 103 of SEQ ID NO. 1. In particular, in some embodiments this amino acid is A, R, N, D, E, Q, G, H, I, L, K, M, F, S, T, W, Y or V. Thus, in some embodiments the present invention provides CD40 binding molecules that comprise:

(i) a heavy chain variable region comprising:
  a. a CDR H1 domain comprising SEQ ID NO. 9,
  b. a CDR H2 domain comprising SEQ ID NO. 10, and
  c. a CDR H3 domain comprising the amino acid sequence AKNSYYG<u>X</u>GGHAMDY (SEQ ID NO. 16), and
(ii) a light chain variable region comprising:
  a. a CDR L1 domain comprising SEQ ID NO. 12,
  b. a CDR L2 domain comprising the amino acid sequence FTS, and
  c. a CDR L3 domain comprising SEQ ID NO. 13,
    wherein X in SEQ ID NO. 17 is selected from A, R, N, D, E, Q, G, H, I, L, K, M, F, S, T, W, Y and V, and
    wherein such molecules bind to, and are agonists of, human CD40.

As described above, the locations/boundaries of the CDRs shown in Table A and Table B above were determined using the IMGT system. However, as also described above, there can be slight differences in the assignment of amino acids to particular FR or CDR region depending on the methodology used. The present invention encompasses CD40 binding molecules comprising the CDRs of the various molecules shown in Table A regardless of which system is used to identify the locations/boundaries of the CDRs. Accordingly, in some embodiments, the present invention provides CD40 binding molecules that comprise: (i) the CDR H1, CDR H2, and CDR H3 regions of SEQ ID NO. 1, 3, 5, 7, or 17; and (i) the CDR L1, CDR L2, and CDR L3 regions of SEQ ID NO. 2, 4, 6, 8, or 18.

For example, in some embodiments, the present invention provides a CD40 binding molecule that comprises: (i) the CDR H1, CDR H2, and CDR H3 regions of SEQ ID NO 1; and (i) the CDR L1, CDR L2, and CDR L3 regions of SEQ ID NO. 2. Similarly, in some embodiments, the present invention provides a CD40 binding molecule that comprises: (i) the CDR H1, CDR H2, and CDR H3 regions of SEQ ID NO 3; and (i) the CDR L1, CDR L2, and CDR L3 regions of SEQ ID NO. 4. In some embodiments, the present invention provides a CD40 binding molecule that comprises: (i) the CDR H1, CDR H2, and CDR H3 regions of SEQ ID NO 5; and (i) the CDR L1, CDR L2, and CDR L3 regions of SEQ ID NO. 6. In some embodiments, the present invention provides a CD40 binding molecule that comprises: (i) the CDR H1, CDR H2, and CDR H3 regions of SEQ ID NO 7; and (i) the CDR L1, CDR L2, and CDR L3 regions of SEQ ID NO. 8. In some embodiments, the present invention provides a CD40 binding molecule that comprises: (i) the CDR H1, CDR H2, and CDR H3 regions of SEQ ID NO 17; and (i) the CDR L1, CDR L2, and CDR L3 regions of SEQ ID NO. 18.

In some embodiments, in addition to the specific CD40 binding molecules (or portions thereof) whose sequences are provided in Table A, and in addition to CD40 binding molecules comprising the CDRs of the molecules whose sequences are provided in Table A, and in addition to CD40 binding molecules comprising the specific CDRs whose sequences are provided in Table B, the present invention also provides variant CD40 binding molecules ("variant molecules"). In some embodiments such variant molecules include humanized, chimeric, optimized, germ-lined, and/or other Ig-formatted versions of any of the specific CD40 binding molecules disclosed—herein provided that such variant molecules bind to, and are agonists of, human CD40. Similarly, in some embodiments such variant molecules include molecules that comprise variants of the specific CDR sequences disclosed herein—provided that such variant molecules bind to, and are agonists of, human CD40. For example, in some embodiments variant molecules that comprise a CDR that has 85%, 90%, 95%, 96%, 97%, 98% or 99% amino acid identity to a CDR sequence as set forth herein are included—provided that such variant molecules bind to, and are agonists of, human CD40. Similarly, in some embodiments variant molecules that comprise a CDR that has 1, or 2, or 3 amino acid substitutions, additions, or deletions as compared to a CDR sequence as set forth herein are included—provided that such variant molecules bind to, and are agonists of, human CD40. In some of such embodiments such amino acid substitutions are conservative substitutions.

Similarly, in some embodiments the present invention provides variant molecules that comprise a VH and/or VL amino acid sequence that is at least 75%, 80%, 85%, 90%, 95%, 96%, 97%, 98% or 99% identical to one of the specific VH or VL sequences provided herein (e.g., as provided by, or comprised within, one of SEQ ID NO. 1 to SEQ ID NO. 8) and/or that comprises 1, 2, 3, 4, 5, 6, 7, 8, 9, 10, or more amino acid substitutions (e.g., conservative substitutions), additions or deletions relative to one of the specific VH or VL sequences provided herein (e.g., as provided by, or comprised within, one of SEQ ID NO. 1 to SEQ ID NO. 8)—provided that such variant molecules bind to, and are agonists of, human CD40. In some such embodiments, the amino acid differences (e.g., substitutions, additions, deletions, etc.) are outside of the CDRs.

In some embodiments, a CD40 binding molecule or variant CD40 binding molecule as described herein, in addition to binding to, and being an agonist of human CD40, also has one or more the following properties: (a) binding to the epitope on CD40 that is bound by TDI-Y-003, Hu10F12 or Hu10F12 (N103D), (b) competition with TDI-Y-003 or Hu10F12 or Hu10F12 (N103D) for binding to its epitope on CD40, (c) CD40 agonist activity without a requirement for Fc receptor engagement, and (d) APC activation activity (e.g., dendritic cell activation activity).

In some embodiments, a CD40 binding molecule according to the present invention is a murine antibody, a human antibody, a humanized antibody, a chimeric antibody, a monoclonal antibody, a polyclonal antibody, a bi-specific antibody, or a multi-specific antibody.

In some embodiments a CD40 binding molecule according to the present invention is, or comprises, a Fab, a Fab', a $F(ab')_2$, a Fd, a Fv, a scFv, a disulfide linked Fv, a V-NAR domain, an IgNar, a VHH domain, a nanobody, an intrabody, an IgGΔCH2, a minibody, a $F(ab')_3$, a tetrabody, a triabody, a diabody, a single-domain antibody, DVD-Ig, Fcab, $mAb^2$, a (scFv)2, or a scFv-Fc.

In some embodiments, a CD40 binding molecule according to the present invention comprises a heavy chain variable domain (VH). In some embodiments, a CD40 binding molecule according to the present invention comprises a light chain variable domain (VL). In some embodiments, a CD40 binding molecule according to the present invention comprises a heavy chain variable domain (VH) and a light chain variable domain (VL). In some embodiments, a CD40 binding molecule according to the present invention comprises a heavy chain constant region (CH). In some embodiments, a CD40 binding molecule according to the present invention comprises a light chain constant region (CL). In those embodiments where the CD40 binding molecule comprises a constant region, in some of such embodiments the constant region is a human constant region. In some of such embodiments the human constant region is a human IgG constant region. In some of such embodiments the human constant region is a human IgG2 constant region.

In some embodiments the present invention provides CD40 binding molecules that can specifically bind to the same CD40 epitope as is bound by TDI-Y-003, Hu10F12 or Hu10F12 (N103D). Similarly, in some embodiments the present invention provides CD40 binding molecules that compete for binding to CD40 with TDI-Y-003 or Hu10F12 Hu10F12 (N103D).

In some embodiments, the CD40 binding molecules provided herein bind to human CD40 with a binding affinity characterized by a dissociation constant ($K_D$) of about 100 pM to about 50 nM. In some embodiments, the CD40 binding molecules provided herein bind to human CD40 with a binding affinity characterized by a dissociation constant ($K_D$) of about 10 nM to about 50 nM. In some embodiments, the CD40 binding molecules provided herein bind to human CD40 with a binding avidity characterized by a dissociation constant ($K_D$) of about 1 nM to about 2 nM. In some embodiments such binding affinities or avidities are determined using a Biacore™ assay or on a Kinetic Exclusion Assay (KinExA®) 3000 platform or on an Octet® instrument.

In some embodiments, the CD40 binding molecules provided herein specifically bind to human CD40 with a dissociation constant or $K_D$ of less than $10^{-6}$ M, or of less than $10^{-7}$ M, or of less than $10^{-8}$ M, or of less than $10^{-9}$ M, or of less than $10^{-10}$ M, or of less than $10^{-11}$ M, of less than $10^{-12}$ M, of less than $10^{-13}$ M, of less than $10^{-14}$ M, or of less than $10^{-15}$ M as measured, e.g., by Biacore™ or KinExA® or Octet®.

In some embodiments, the CD40 binding molecules provided herein bind to human CD40 with a $K_{off}$ of less than $1\times10^{-3}$ $s^{-1}$, or less than $2\times10^{-3}$ $s^{-1}$. In other embodiments, the CD40 binding molecules provided herein bind to human CD40 with a $K_{off}$ of less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than less than $5\times10^{-7}$ $s^{-1}$, less than $10^{-8}$ $s^{-1}$, less than $5\times10^{-8}$ $s^{-1}$, less than $10^{-9}$ $s^{-1}$, less than $5\times10^{-9}$ $s^{-1}$, or less than 101 $s^{-1}$ as measured, e.g., by Biacore™ or KinExA® or Octet®.

In some embodiments, the CD40 binding molecules provided herein bind to human CD40 with an association rate constant or $K_{on}$ rate of at least $10^5$ $M^{-1}$ $s^{-1}$, at least $5\times10^5$ $M^{-1}$ $s^{-1}$, at least $10^6$ $M^{-1}$ $s^{-1}$ at least $5\times10^6$ $M^{-1}$ $s^{-1}$, at least $10^7$ $M^{-1}$ $s^{-1}$ at least $5\times10^7$ $M^{-1}$ $s^{-1}$, or at least $10^8$ $M^{-1}$ $s^{-1}$, or at least $10^9$ $M^{-1}$ $s^{-1}$ as measured, e.g., by Biacore™ or KinExA® or Octet®.

III. Preparation of CD40 Binding Molecules

The CD40 binding molecules of the invention can be prepared using any suitable means known in the art. For example, the CD40 binding molecules of the invention can be prepared using recombinant DNA methods. For example, polynucleotides encoding the CD40 binding molecules can be cloned into suitable expression vectors. Transfection of host cells with the expression vector results in generation of the molecules by the host cells.

IV. Use of CD40 Binding Molecules

The present invention provides various methods of using the CD40 binding molecules described herein.

For example, in some embodiments the present invention provides methods for activating cells expressing CD40, such methods comprising contacting cells that express CD40 with a CD40 binding molecule as described herein (or a composition, such as a pharmaceutical composition, comprising such a CD40 binding molecule), thereby activating CD40-induced signaling pathways in the cells. In some embodiments the present invention provides methods for activating cells expressing CD40, such methods comprising contacting cells that express CD40 with a CD40 binding molecule as described herein (or a composition, such as a pharmaceutical composition, comprising such a CD40 binding molecule), thereby activating CD40-induced signaling pathways in the cells. In some such embodiments the cells are myeloid cells. In some such embodiments the cells are lymphoid cells. In some such embodiments the cells are endothelial cells. In some such embodiments the cells are immune cells. In some such embodiments the cells are cells with innate or adaptive immune cell function. In some such embodiments the cells are antigen presenting cells. In some embodiments the antigen presenting cells are dendritic cells. In some embodiments the antigen presenting cells are B cells. In some embodiments the antigen presenting cells are macrophages. In some embodiments the cells are in vitro. In some embodiments the cells are in vivo.

The present invention provides methods of activating T cells via CD40-mediated activation of antigen presenting cells, such methods comprising contacting the antigen presenting cells with a CD40 binding molecule as described herein (or a composition, such as a pharmaceutical composition, comprising such a CD40 binding molecule). In some embodiments the antigen presenting cells are dendritic cells. In some embodiments the antigen presenting cells are B cells. In some embodiments the antigen presenting cells are macrophages. In some embodiments the antigen presenting cells are monocytes. In some embodiments the antigen presenting cells are endothelial cells. In some embodiments the cells are in vitro. In some embodiments the cells are in vivo.

The present invention also provides methods for detecting CD40 or CD40-expressing cells in a sample (such as in a cell or tissue sample—e.g., a biopsy sample) or in a subject. Such methods typically involve contacting a cell or tissue sample with a CD40 binding molecule as described herein, and performing an assay to determine whether the CD40 binding molecule binds to the cell or tissue sample and/or performing an assay to quantify any binding of the CD40 binding molecule binds to the cell or tissue sample.

In some embodiments the present invention provides methods for treating melanoma in subjects in need thereof, such methods comprising administering to a subject that has melanoma an effective amount of a CD40 binding molecule as described herein, (or a composition, such as a pharmaceutical composition, comprising such a CD40 binding molecule). In some such embodiments the method results in regression of a melanoma in the subject. In some such embodiments the method results in a delay of tumor growth or a reduction in the rate of tumor growth. In some such embodiments the method results in limiting proliferation of melanoma tumor cells in the subject. In some such embodiments the method results in killing of melanoma tumor cells in the subject. In some embodiments the survival of subjects treated with such methods is increased as compared to that of subjects with melanoma that are not so treated.

As used herein, the terms "treat," "treating," "treatment," "administration," and "administering" refer to contact of an exogenous pharmaceutical, therapeutic, or composition to an animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, binding compound, or by another cell.

In carrying out the treatment methods described herein, any suitable method or route of administration can be used to deliver the CD40 binding molecules described herein. In some embodiments systemic administration may be employed, for example, intravenous administration, or any other route of systemic administration known in the art that is suitable for use with the present CD40 binding molecules. In some embodiments intra-tumoral delivery may be employed. For example, the active agents described herein may be administered directly into a tumor by local injection, infusion through a catheter placed into the tumor, delivery using an implantable drug delivery device inserted into a tumor, or any other means known in the art for direct delivery of an agent to a tumor.

As used herein the term "effective amount" refers to an amount of a CD40 binding molecule (or a composition comprising a CD40 binding molecule) as described herein that, when administered alone or in combination with an additional therapeutic/prophylactic agent to a cell, tissue, or subject, is effective to prevent or cause a measurable improvement in one or more symptoms of the condition being treated (e.g., melanoma). For example, such measurable improvements include, but are not limited to, reducing the rate of growth of a tumor (or of tumor cells), halting the growth of a tumor (or of tumor cells), causing regression of a tumor (or of tumor cells), reducing the size of a tumor (for example as measured in terms of tumor volume or tumor mass), reducing the grade of a tumor, eliminating a tumor (or tumor cells), and the like. When applied to a combination, an effective dose refers to combined amounts of the active ingredients that result in the prophylactic or therapeutic effect, whether administered in combination, serially or simultaneously.

An appropriate "effective" amount in any individual case may be determined using standard techniques known in the art, such as dose escalation studies, and may be determined taking into account such factors as the desired route of administration (e.g., systemic vs. intra-tumoral), desired frequency of dosing, etc. Furthermore, an "effective amount" may be determined in the context of any co-administration method to be used. One of skill in the art can readily perform such dosing studies (whether using single agents or combinations of agents) to determine appropriate doses to use, for example using assays such as those described in the Examples section of this patent application—which involve administration of CD40 binding molecules to animal subjects routinely used in the pharmaceutical sciences for performing dosing studies.

In certain embodiments the compositions and methods of treatment provided herein may be employed together with other compositions and treatment methods known to be useful for the given condition being treated (here—melanoma), including, but not limited to, surgical methods (e.g., melanoma resection), radiation therapy methods, treatment with chemotherapeutic agents, treatment with immune checkpoint inhibitors, and the like. Similarly, in certain embodiments the methods of treatment provided herein may be employed together with procedures used to monitor disease status/progression, such as biopsy methods and diagnostic methods (e.g., MRI methods or other imaging methods).

The invention is further described by, and understood with reference to, the following non-limiting Examples, as well as the Figures referred to therein.

Examples

Development & Characterization of CD40 Binding Molecules

Background

Stimulation of the CD40 pathway in APCs has been recognized as a highly effective way to activate APCs.[6,7] CD40 agonists have demonstrated antitumor activity as monotherapy in human cancers.[8-10] Currently there is great interest in the use of CD40 stimulation in the treatment of pancreatic cancer, in part because of compelling early-phase data incorporating the CD40 agonist mAb APX005M (Apexigen) along with chemotherapy and PD-1 blockade in the first-line treatment of metastatic pancreatic cancer.[11]

Several approaches to induce CD40 signaling with an agonist agent have been explored.[20] For example, certain CD40 agonist antibodies with a modified Fc portion that increases binding to FcγRIIB, which is present on intra-tumoral myeloid cells, can more potently stimulate APCs.[13] This has led to the production of a series of CD40 agonist antibodies designed to have increased FcγRIIB binding, including APX005M[14] or 2141-V11[15].

Instead of relying on Fc receptor engagement, this approach focused on identifying CD40 agonist antibodies with certain other intrinsic features, including competition with the binding site of CD40L, the ligand for CD40. Binding CD40 at the natural ligand binding site has been shown to increase agonist activity,[22] and may further reduce inter-patient variability by preventing uncontrolled activation of CD40 by endogenous CD40L.

Identification & Characterization of CD40 Binding Molecules

Antibody generation was carried out by immunizing mice with recombinant CD40 protein. Hybridomas were generated by electrofusion, and the supernatants were screened for antibodies that bound to CD40, competed with CD40L for binding to CD40, and displayed potent agonist activity on cells that overexpress CD40. After completion of subcloning and sequencing, chimeric versions of the top-ranked agonist antibodies were produced with the murine variable regions fused to human constant regions with either an IgG1 or IgG2 isotype subclass. The human/mouse chimeric antibodies were tested along with the parental murine antibodies in an APC activation assay using dendritic cells isolated from PBMCs.

The 10F12 antibody was selected as a lead candidate based on it having the following biological and functional properties:

- Binding to monomeric CD40 in solution at intermediate affinity,
- High-affinity binding to cells overexpressing CD40, and to cells that endogenously express CD40,
- Cross-reactivity to cynomolgus monkey CD40 within 2-fold (no cross-reactivity to mouse CD40),
- Competition with CD40L for the ligand binding site on CD40,
- Potent agonist activity in an in vitro assay using HEK293 cells that overexpress CD40 and contain a NF-kB luciferase reporter gene,
- Potent activation of dendritic cells isolated from PBMCs when formatted as a human IgG2.

For immunizations, the extracellular domains of human CD40 (residues 21-192), cynomolgus monkey CD40 (residues 21-192) and mouse CD40 (residues 24-192), each fused via their carboxy-terminus to a human Fc fragment, were used.

Two cohorts of mice (Balb/c and NZB/W strains) were immunized with human CD40-Fc. For another cohort of Balb/c mice, human, cynomolgus monkey and mouse CD40-Fc were used alternatively in consecutive immunizations, with the goal to obtain antibodies that are cross-reactive between human, cynomolgus and mouse CD40. Serum was collected to assess the immune response to CD40. All animals had midpoint titers of 1; 10,000 or greater when analyzed by ELISA using recombinant human CD40 (residues 21-192) fused to a 6×His-tag (SEQ ID NO. 19) at the carboxy-terminus. Weak binding to mouse CD40-His at mid-point titers of 1:200 or lower was observed for sera from the Balb/c mice that had been immunized with CD40-Fc from various species. Three days after the final boost, lymph nodes were collected and pooled for each cohort, followed by isolation of IgG-producing B cells by magnetic sorting. The enriched B cells were fused with mouse myeloma cells to generate hybridomas, which were plated for screening.

Hybridoma supernatants were analyzed. Binding to human, cynomolgus monkey and mouse CD40 was analyzed by ELISA, followed by testing of the binders for interaction with a HEK293 cell line stably expressing human CD40 on the surface.

Subsequently, competition of the antibodies with human CD40L for binding to CD40 was analyzed by ELISA, and agonist activity was assessed using a HEK293 cell line that overexpresses human CD40 and includes a luciferase reporter gene under the NF-kB promoter.

To assess the contribution of the Fc portion to the agonist activity of the CD40 lead candidate antibodies, they were re-formatted to generate chimeric molecules with mouse variable regions fused to human constant regions of either the IgG1 or IgG2 isotype subclass. The chimeric mAbs were expressed recombinantly in HEK293 cells to obtain purified material that can be used to determine dissociation constants in solution, agonist potency on cells, and activity in an APC stimulation assay.

Dissociation constants (KD), on-rates (kon) and off-rates (koff) for the 10F12 chimeric mAb were determined by BLI using soluble, monomeric human CD40-His (Table 1). The KD value for binding to human CD40 in solution was 27.1 nM and 26.5 nM for human IgG1 and human IgG2, respectively.

TABLE 1

Dissociation constants (KD), on-rates (kon) and off-rates (koff) of chimeric lead candidate mAb.

| | Human IgG1 | | | Human IgG2 | | |
|---|---|---|---|---|---|---|
| Antibody | $K_D$ [nM] | $k_{on}$ [1/Ms] | $k_{off}$ [1/s] | $K_D$ [nM] | $k_{on}$ [1/Ms] | $k_{off}$ [1/s] |
| 10-F12 | 27.1 | 2.62E+05 | 7.10E−03 | 26.5 | 3.44E+05 | 9.11E−03 |

Agonist activity was measured using the HEK293-CD40 NF-kB luciferase reporter cell line in the presence of anti-human Fc to mediate antibody crosslinking. Table 2 summarizes the $EC_{50}$ values and maximum stimulation compared to CD40L.

TABLE 2

$EC_{50}$ for agonist activity and maximum stimulation of chimeric lead candidate mAb (HEK293-CD40 NF-κB-Luciferase reporter system)

| | Human IgG1 | | Human IgG2 | |
|---|---|---|---|---|
| Antibody | $EC_{50}$ [nM] | Max Stim [% CD40L] | $EC_{50}$ [nM] | Max Stim [% CD40L] |
| 10-F12 | 0.333 | 63.4 | 0.010 | 96.5 |
| hCD40L | 3.580 | 100.0 | — | — |

The chimeric CD40 antibodies were tested in a human dendritic cell activation assay. Monocytes were first isolated from healthy human donor blood by Ficoll density gradient centrifugation and plastic adherence. To obtain monocyte-derived dendritic cells, adherent cells were cultured in the presence of hIL-4 and hGM-CSF for five to seven days. Differentiated dendritic cells (DCs) were harvested and plated in 96 wells at a concentration of $0.5\text{-}2\times10^6$/mL and stimulated for 48 hours with 10 μg/mL anti-CD40 antibodies. A maturation mix of prostaglandin E, TNFα, IL-1b, IL-4, IL-6, and GM-CSF or the Toll-like receptor 4 (TLR4) agonists lipopolysaccharide (LPS) and monophosphoryl lipid A (MPL) were used as positive controls to activate DCs. Cell culture supernatants were analyzed for cytokine secretion in multiplexed immunoassays. Dendritic cells were washed and subjected to immunostaining, followed by flow cytometry analysis. The following DC activation markers were analyzed: HLAABC, HLA-DR, CD80, and CD86.

Figure 1:
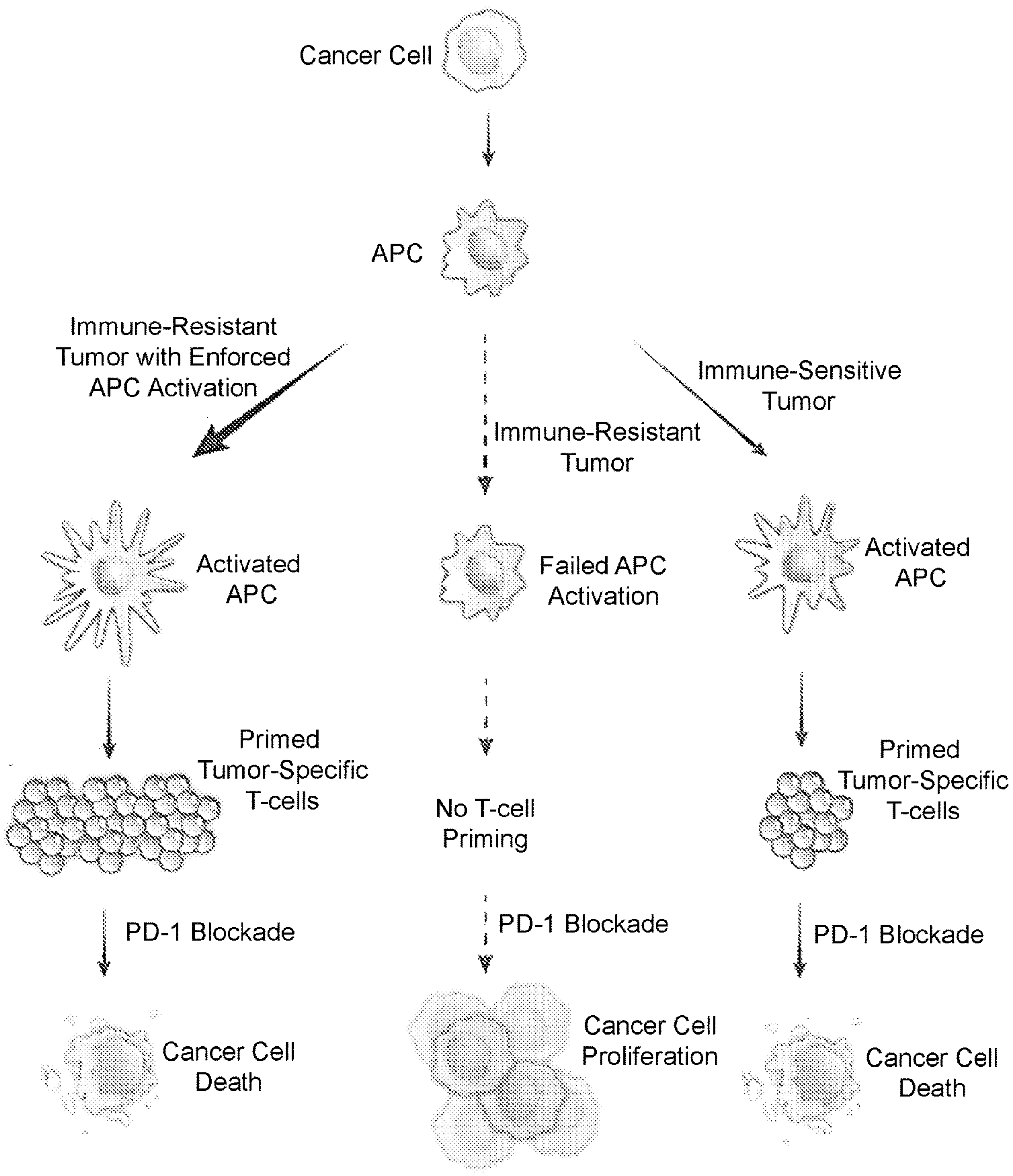
FIG. 1. Model of treatment to overcome resistance to PD-1 blockade in resistant cancers. Patients sensitive to PD-1 blockade have activated APCs presenting tumor antigens at baseline, as depicted in the top row. Patients resistant to PD-1 blockade have been found to have limited or defective APC activation at baseline, as shown in the middle row. Treatment with a CD40 agonist antibody, represented by the bottom row, enforces the activation of APCs capable of priming tumor-specific T cells.
Figure 2:
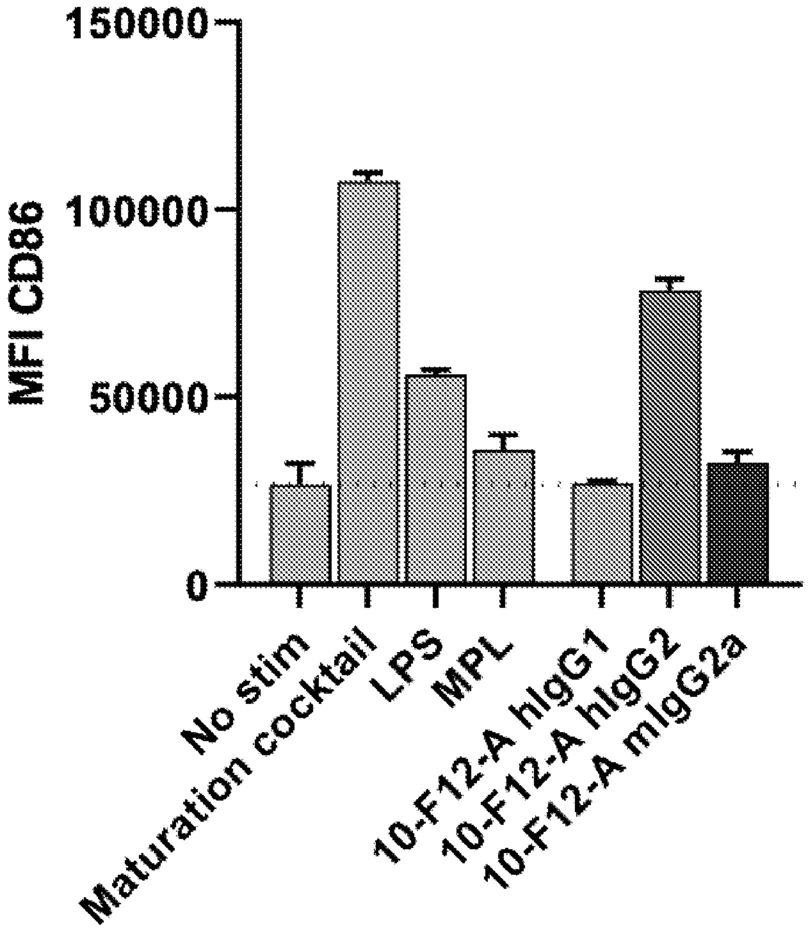
FIG. 2. Activation of dendritic cells by chimeric CD40 agonist antibodies. Dendritic cells were stimulated with a "maturation cocktail" (tumor necrosis factor alpha (TNFα) 10 ng/mL, IL-6 1000 IU/mL, IL-1 beta 2 ng/mL, PGE-2 5 mM, GM-CSF 1000 IU/mL and IL-4 500 IU/mL), lipopolysaccharide (LPS), monophosphoryl lipid (MPL), or 10 μg/mL chimeric antibodies in hIgG1, hIgG2, or mIgG format for 24 hours and subjected to flow cytometry analysis. Shown is the mean fluorescence intensity (MFI) for the activation marker CD86.
Figure 3:
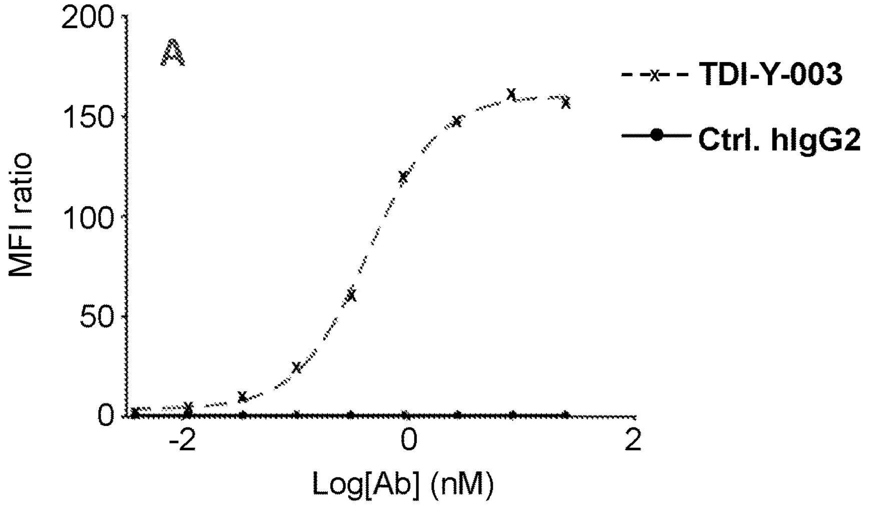
FIG. 3 A-C. Binding of TDI-Y-003 to overexpressed and endogenous CD40 on cells. TDI-Y-003 and human IgG2 isotype control antibody was used to stain HEK293 overexpressing CD40 (FIG. 3 A) as well as Raji (FIG. 3 B) and primary human dendritic cells (FIG. 3 C) expressing endogenous CD40 at the indicated concentrations. MFI values are normalized to secondary antibody only controls (MFI ratio).
Figure 3:
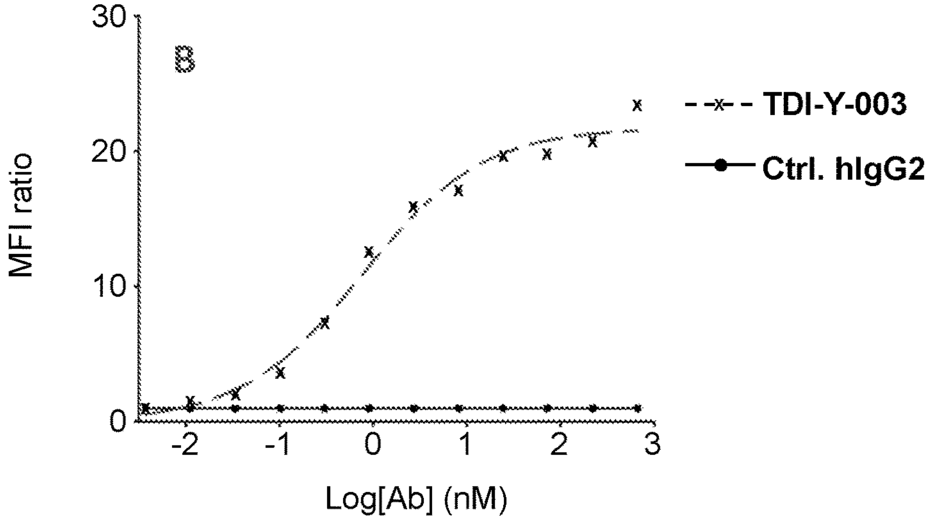
Figure 3:
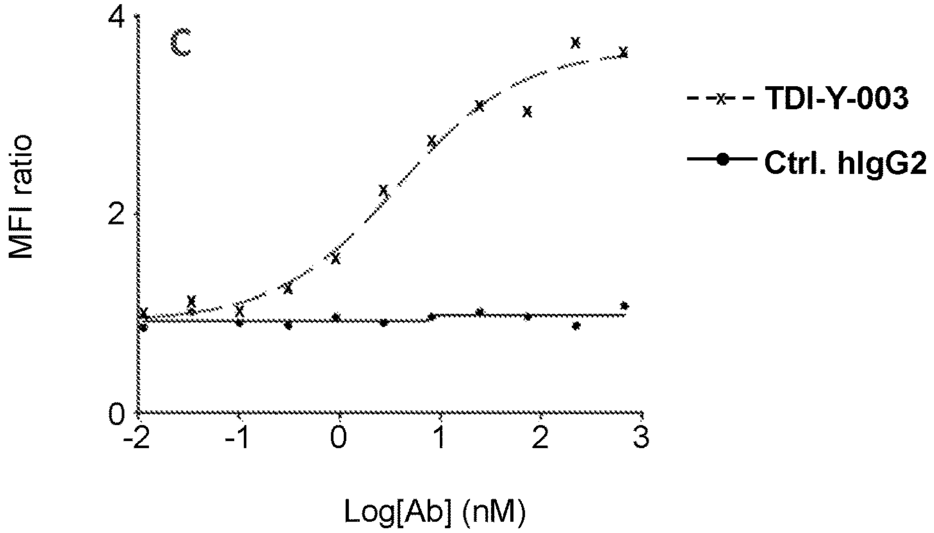

Antibody 10-F12A formatted with a human IgG2 constant region (10-F12 hIgG2) emerged as a robust agonist in a series of dendritic cell activation assays with peripheral blood mononuclear cells (PBMCs) from multiple donors (FIG. 2). Several other cell surface activation markers (including CD80, MHC class I and II) as well as multiple cytokines (e.g., IL-6, IL-10, IL-12 and TNFα) were also elevated for 10-F12A hIgG2.

Humanization of the 10F12 Antibody

Humanization of the murine 10F12 antibody variable region was carried out by homology modeling followed by assessment of the productivity and antigen binding properties of a panel of candidate molecules. The selected humanized candidate antibody sequence was then analyzed in silico for potential post-translational modification sites in the CDRs and for potential predicted immunogenicity.

Analysis of the humanized mAb 10F12 variable region sequence identified a potential deamidation 'hot-spot' (an asparagine followed by a glycine, NG) in CDR3 of the heavy chain. To evaluate the impact of deamidation on the binding properties of the humanized 10F12 antibody, a charge mimic mutation (N103D) was introduced. The charge mimic variant, mAb hu10F12 (N103D), retained the specificity and affinity of the parent antibody hu10F12. An N103Q mutation was introduced in the hu10F12 mAb in order to ablate the CDR3 deamidation site, generating mAb hu10F12 (N103Q). The introduction of the conservative N to Q change had minimal impact on the biopharmaceutical, binding, and functional properties. Hu10F12 (N103Q) was selected as the lead mAb and designated TDI-Y-003.

Antibody TDI-Y-003 produced in stable CHO pools was tested in a series of binding and functional assays in vitro as well as an in vivo study in a disease-relevant animal model. Affinity to human CD40 was measured by BLI using an Octet Red96e. TDI-Y-003 binds to CD40 with a KD of 40 nM, with an intermediate on-rate and a relatively fast off-rate (Table 3). The KD of TDI-Y-003 for binding to human CD40-Fc was 1.2 nM. The slower off-rate seen for this interaction is likely a result of the avidity between the bivalent TDI-Y-003 IgG and the dimeric CD40-Fc.

TABLE 3

Binding kinetics of TDI-Y-003 to human CD40

| Antigen | $k_{on}$ (1/Ms) | $k_{off}$ (1/s) | $K_D$ (nM) |
|---|---|---|---|
| Human CD40-His | $1.2 \times 10^6$ | $4.8 \times 10^{-2}$ | 40 |
| Human CD40-Fc | $1.0 \times 10^6$ | $1.3 \times 10^{-3}$ | 1.2 |

Affinity to cynomolgus monkey and mouse CD40 was measured by BLI using an Octet Red96e. TDI-Y-003 binds to cyno CD40 with a KD of 48 nM (Table 4), which is similar to human CD40 (40 nM). TDI-Y-003 showed no binding to mouse CD40-His at concentrations up to 1.7 μM.

TABLE 4

Binding kinetics of TDI-Y-003 to monomeric cynomolgus monkey and mouse CD40

| Antigen | $k_{on}$ (1/Ms) | $k_{off}$ (1/s) | $K_D$ (nM) |
|---|---|---|---|
| Cyno CD40-His | $9.77 \times 10^5$ | $4.71 \times 10^{-2}$ | 48 |
| Mouse CD40-His | No binding | No binding | No binding |

To assess the binding of TDI-Y-003 to cell surface-bound CD40, HEK293 overexpressing CD40 as well as Raji cells (B-lymphocytes) and primary human dendritic cells, which express endogenous CD40, were used. TDI-Y-003 bound HEK293-CD40 and Raji cells with $EC_{50}$ values in the sub-nanomolar range at 0.44 and 0.77 nM, respectively (Table 5). The $EC_{50}$ value for binding to dendritic cells was 3.85 nM.

TABLE 5

$EC_{50}$ Binding Values of TDI-Y-003 on Different Cell Lines

| Cell Line | Antibody | $EC_{50}$ (nM) |
|---|---|---|
| HEK293 CD40 | TDI-Y-003 | 0.44 |
| Raji | TDI-Y-003 | 0.77 |
| Dendritic Cells | TDI-Y-003 | 3.85 |

Figure 4:
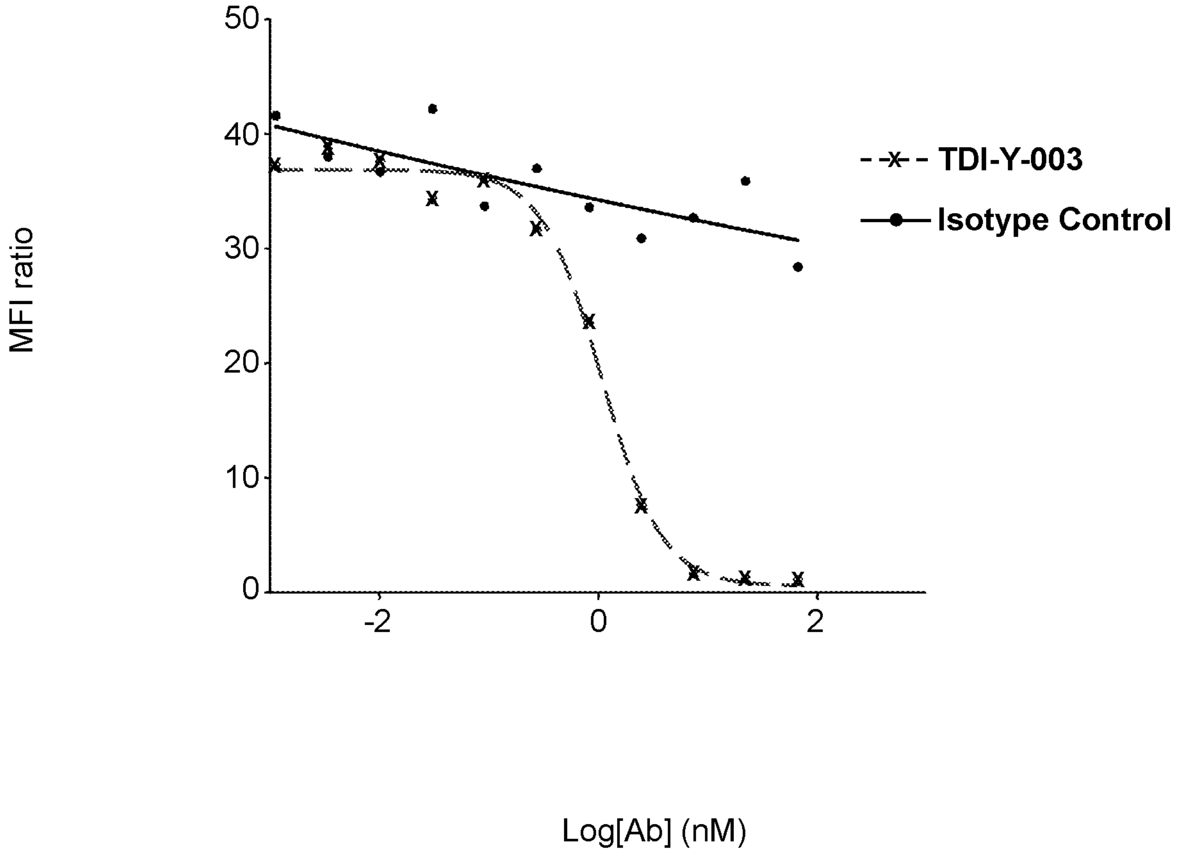
FIG. 4. Competitive binding of TDI-Y-003 with CD40 ligand to CD40 stably expressed on HEK293 cells. HEK293 cells stably expressing CD40 were co-incubated with either TDI-Y-003 or isotype control antibody and HA-tagged CD40 ligand. CD40 ligand binding was assessed by flow cytometry with a PE labeled anti-HA antibody. Results are normalized to secondary antibody only controls (MFI ratio).

Competitive binding of TDI-Y-003 with CD40L for binding to CD40 was assessed using HEK293 cells stably expressing CD40. Cells were co-incubated with HA tagged CD40 ligand and TDI-Y-003 or isotype control at the indicated concentrations and analyzed for CD40 ligand binding by flow cytometry (FIG. 4). The $IC_{50}$ for competition of TDI-Y-003 with CD40L was 1.07 nM (Table 6).

TABLE 6

$IC_{50}$ Value of TDI-Y-003 in Ligand Competition Assay

| Antibody | $IC_{50}$ (nM) |
|---|---|
| TDI-Y-003 | 1.07 |

Figure 5:
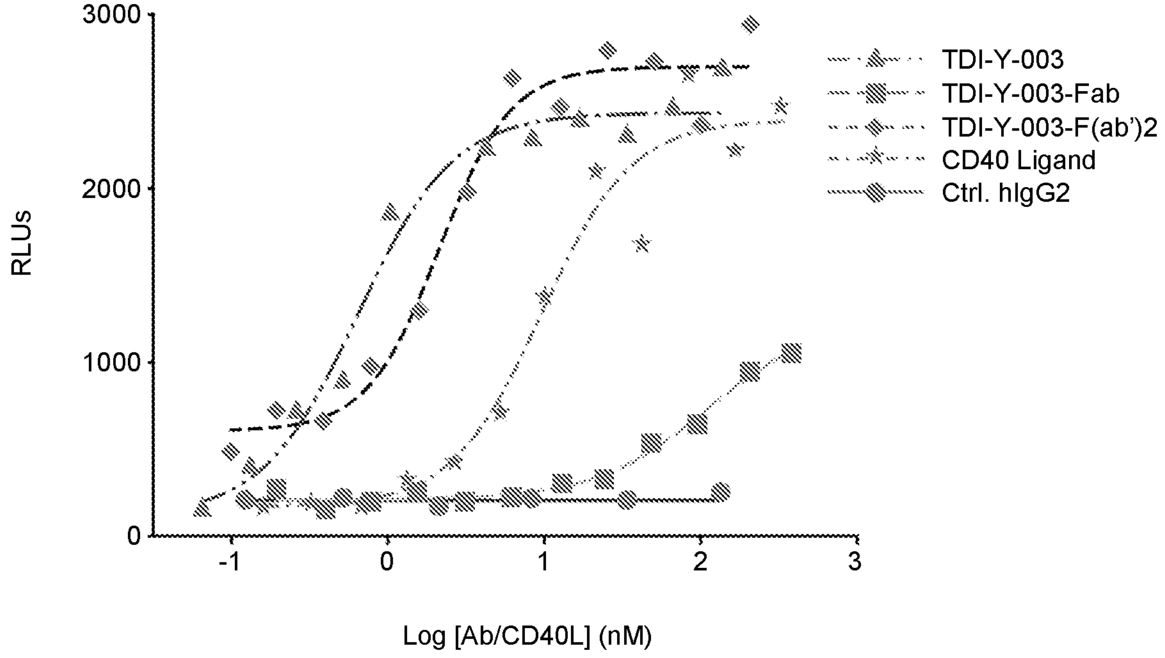
FIG. 5. Agonist activity of TDI-Y-003 variants in an HEK293 NF-kB Luciferase reporter line stably expressing CD40. HEK293 NF-kB luciferase reporter cell line overexpressing CD40 was treated with TDI-Y-003, a TDI-Y-003 Fab fragment generated by papain cleavage (TDI-Y-003-Fab), a TDI-Y-003 F(ab')2 fragment generated by pepsin cleavage (TDI-Y-003-F(ab')2), CD40 ligand and human IgG2 isotype control antibody at the indicated concentrations for 24 hours.

TDI-Y-003 was tested for agonist activity using a HEK293 cell line stably expressing CD40 with an NF-kB-luciferase reporter. To assess the contribution of the Fc portion, a F(ab')2 fragment of TDI-Y-003 was included. In addition, CD40 ligand and a Fab fragment of TDI-Y-003 were utilized controls. FIG. 5 shows potency curves for TDI-Y-003 in various formats. TDI-Y-003 showed potent agonist activity with an $EC_{50}$ value of 0.64 nM (Table 7). The F(ab')2 variant of TDI-Y-003 had an $EC_{50}$ of 2.14 nM.

TABLE 7

$EC_{50}$ Values of TDI-Y-003 in Agonist Assay

| Antibody | $EC_{50}$ (nM) |
|---|---|
| TDI-Y-003 | 0.64 |
| TDI-Y-003-F(ab')$_2$ | 2.14 |
| TDI-Y-003-Fab | 112 |
| CD40 Ligand | 9.62 |

Figure 6:
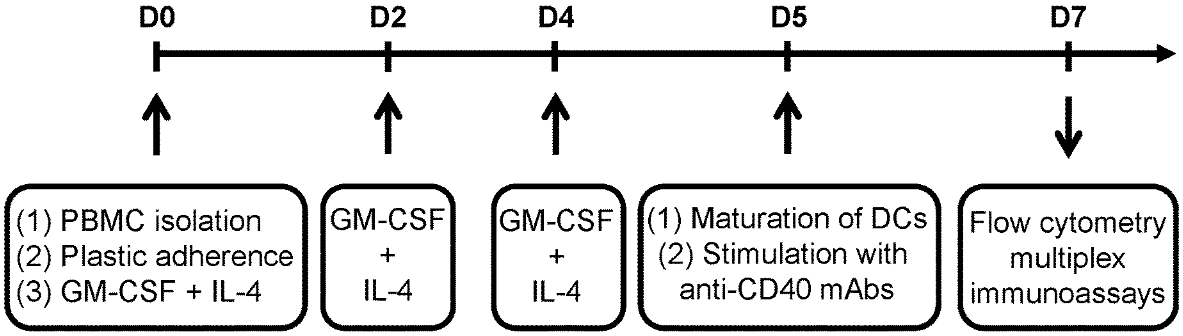
FIG. 6. Cell processing and cell stimulation schedule. Dendritic cells were differentiated from healthy donor peripheral blood mononuclear cells (PBMCs) by culturing isolated monocytes in the presence of human interleukin (IL)-4 and human granulocyte-macrophage colony-stimulating factor (GM-CSF). The dendritic cells were stimulated for 48 hours with test agents (TDI-Y-003, controls).
Figure 7:
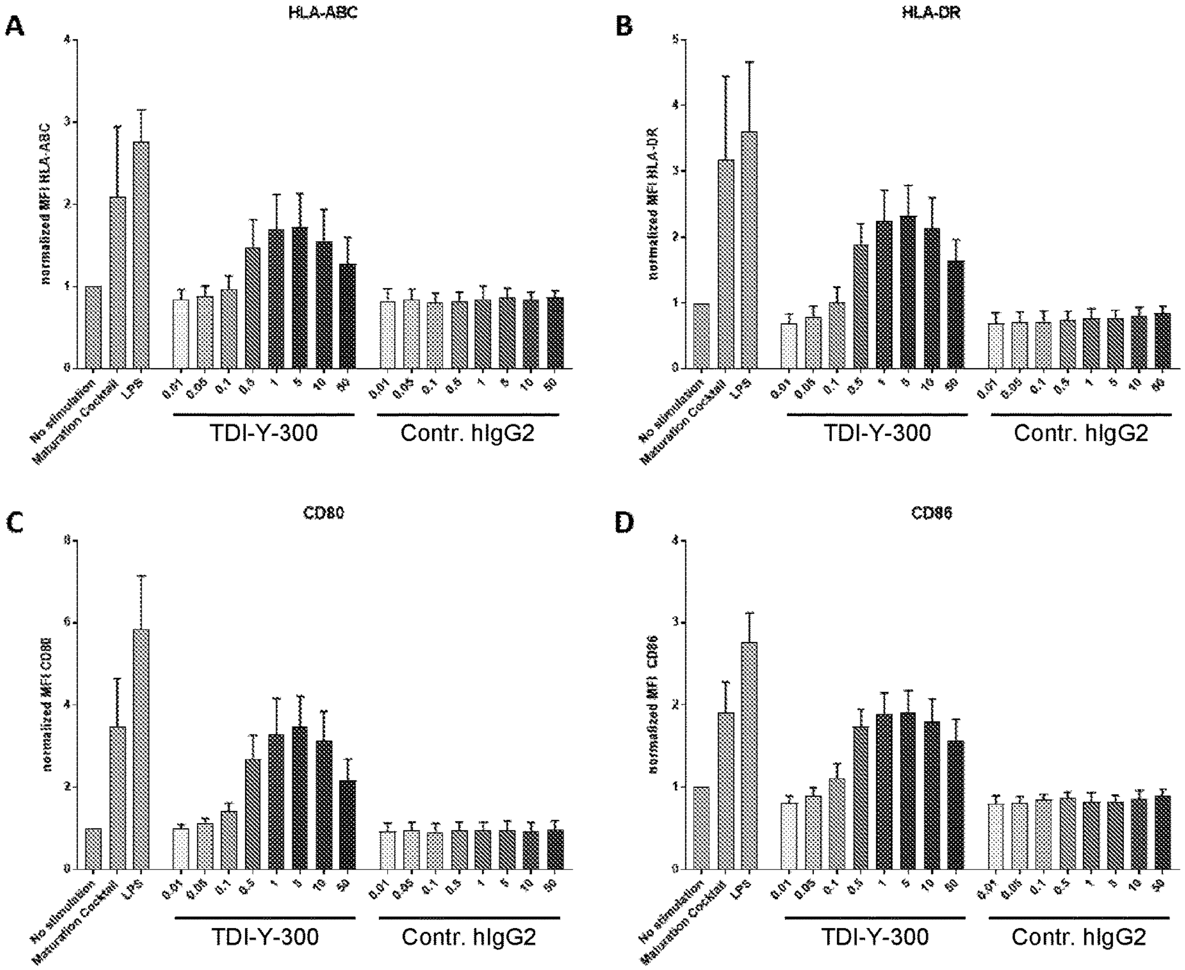
FIG. 7 A-D. Activation of dendritic cells by TDI-Y-003. Dendritic cells from 4 different healthy donors were stimulated with increasing doses of TDI-Y-003 or human IgG2 isotype control. Negative (no stimulation) and positive (maturation cocktail, LPS) assay controls are shown. Expression of the DC activation markers HLA-ABC (FIG. 7 A), HLA-DR (FIG. 7 B), CD80 (FIG. 7 C), and CD86 (FIG. 7 D) was analyzed by flow cytometry. MFI values were normalized to unstimulated control across all donors.

Human dendritic cells were used to analyze the ability of the TDI-Y-003 antibody to activate professional antigen presenting cells. Monocytes were isolated from human blood and differentiated into dendritic cells as previously described and as shown in FIG. 6. Differentiated and matured dendritic cells were stimulated for 48 hours with TDI-Y-003 or human IgG2 isotype control concentrations ranging from 0.01 μg/mL to 50 μg/mL. As previously described, a maturation cocktail or the TLR4 agonist lipopolysaccharide (LPS) were used as positive controls to activate DCs. The following DC activation markers were analyzed: HLA-ABC, HLA-DR, CD80, and CD86 (FIG. 7).

TABLE 8

| EC$_{50}$ values for TDI-Y-003 in DC activation assay | | | |
|---|---|---|---|
| Antibody | Marker | EC$_{50}$ [nM] | MFI$_{max}$ [% of TDI-Y-003] |
| TDI-Y-003 | HLA-ABC | 2.5 | 100 |
| | HLA-DR | 1.7 | 100 |
| | CD80 | 2.0 | 100 |
| | CD86 | 5.5 | 100 |

Figure 8:
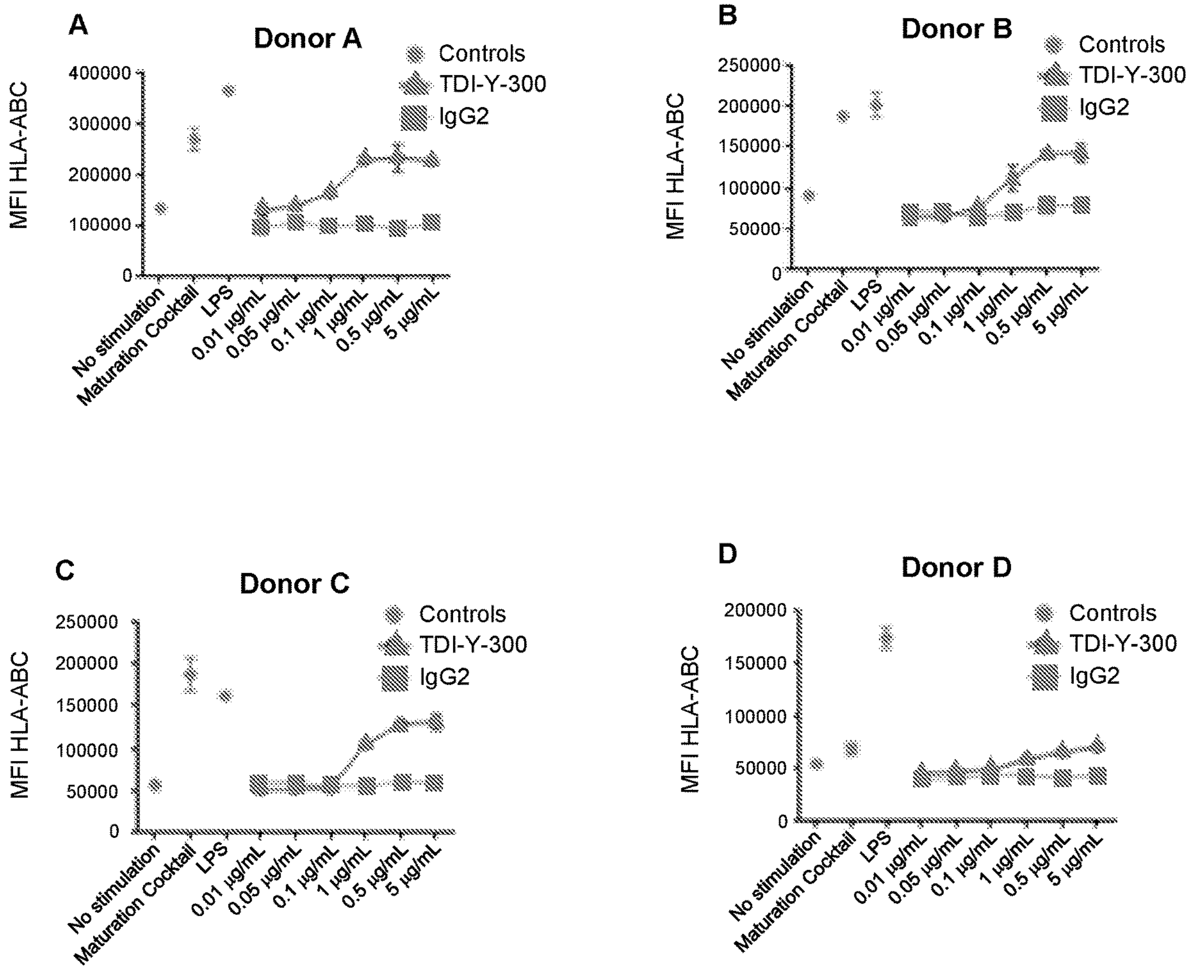
FIG. 8 A-P. Response curves of dendritic cells to TDI-Y-003. Dose response curves for dendritic cells from four individual healthy donors (Donors A-D), are shown. MFI values for HLA-ABC (FIG. 8 A-D), HLA-DR (FIG. 8 E-H), CD80 (FIG. 8 I-L), and CD86 (FIG. 8 M-P) are depicted in response to 48 hours stimulation with TDI-Y-003 or human IgG2 isotype control.
Figure 8:
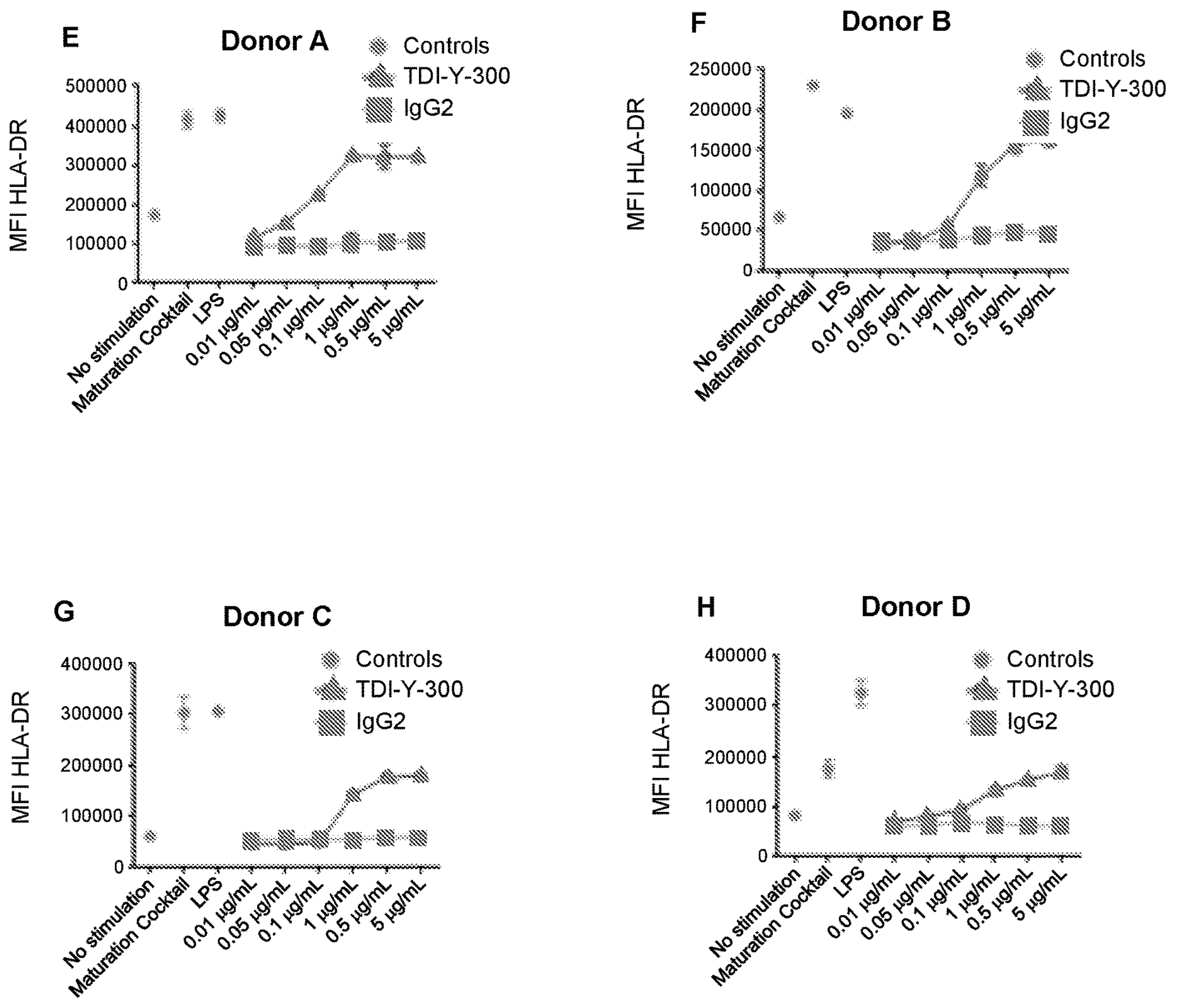
Figure 8:
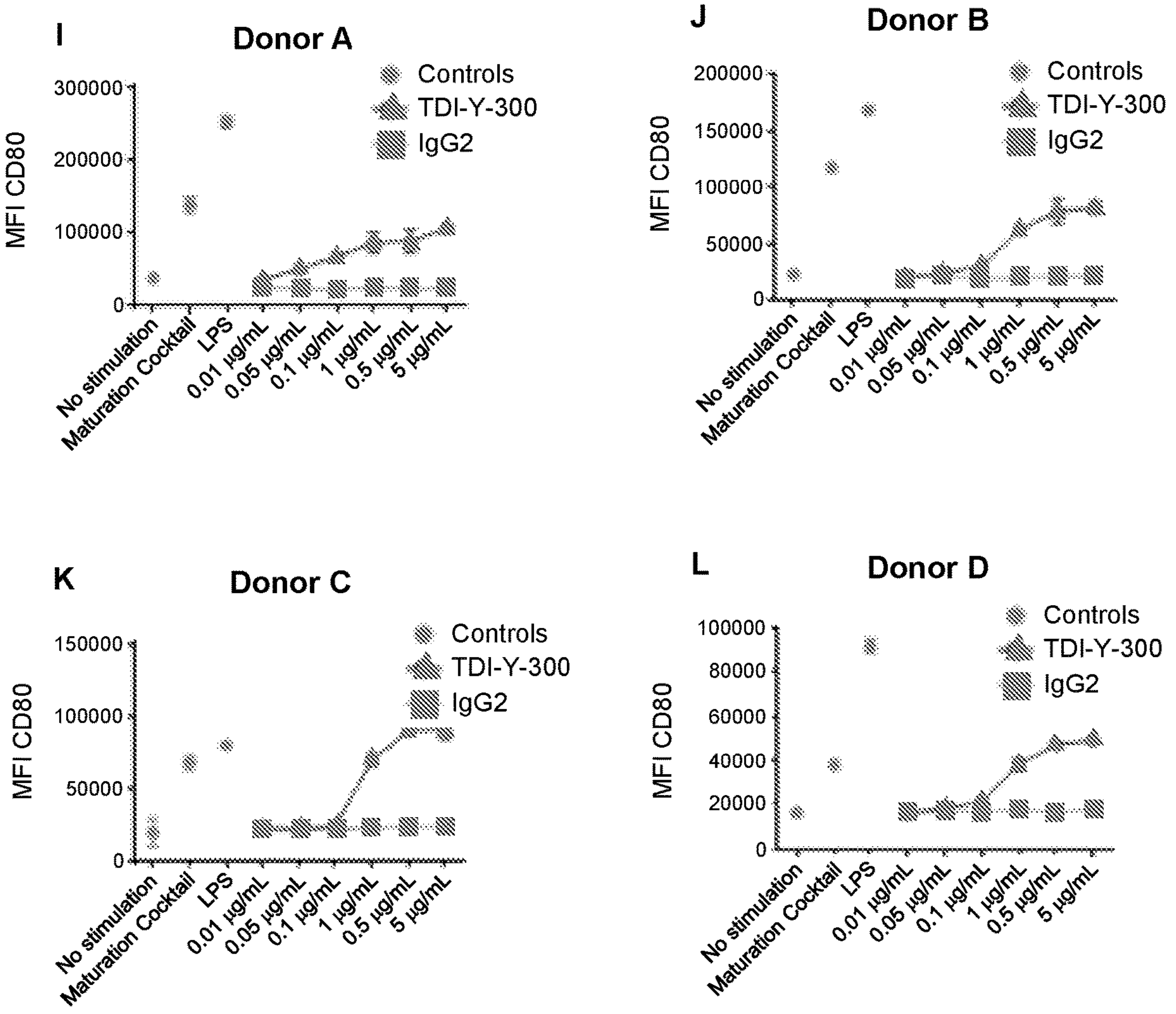
Figure 8:
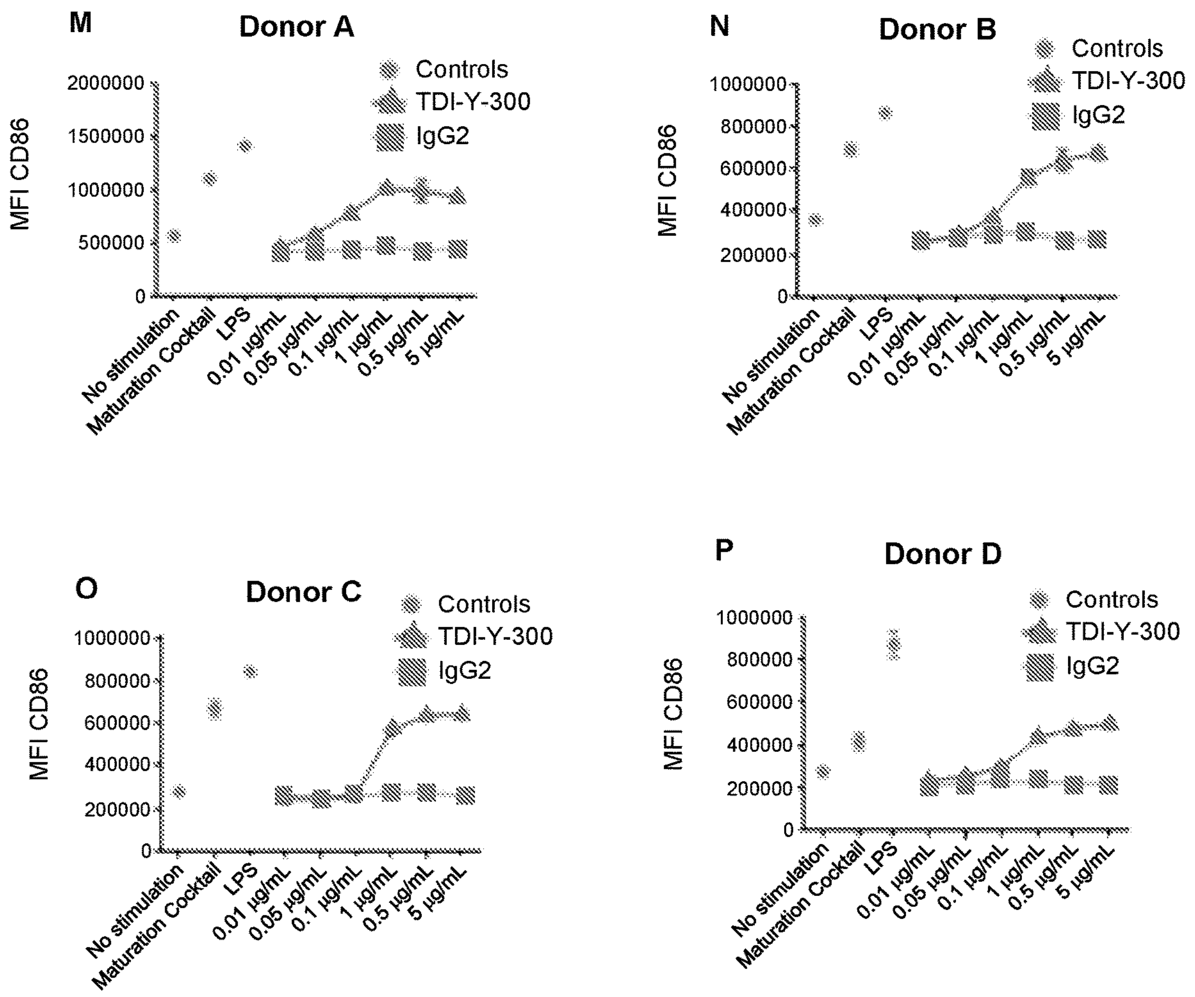

The DC activation assay showed a strong increase in expression of all dendritic cell activation markers tested. Expression levels of HLA-ABC, HLA-DR, CD80, and CD86 increased in a dose-dependent manner and to comparable extents in four different donors. Efficacy of TDI-Y-003 reached a plateau at a concentration of 5 μg/mL in all individually tested donors. Treatment with a human IgG2 isotype control did not result in detectable DC activation. Average EC$_{50}$ values were calculated (Table 8) using dose-response curves from four different donors (FIG. 8).

Figure 9:
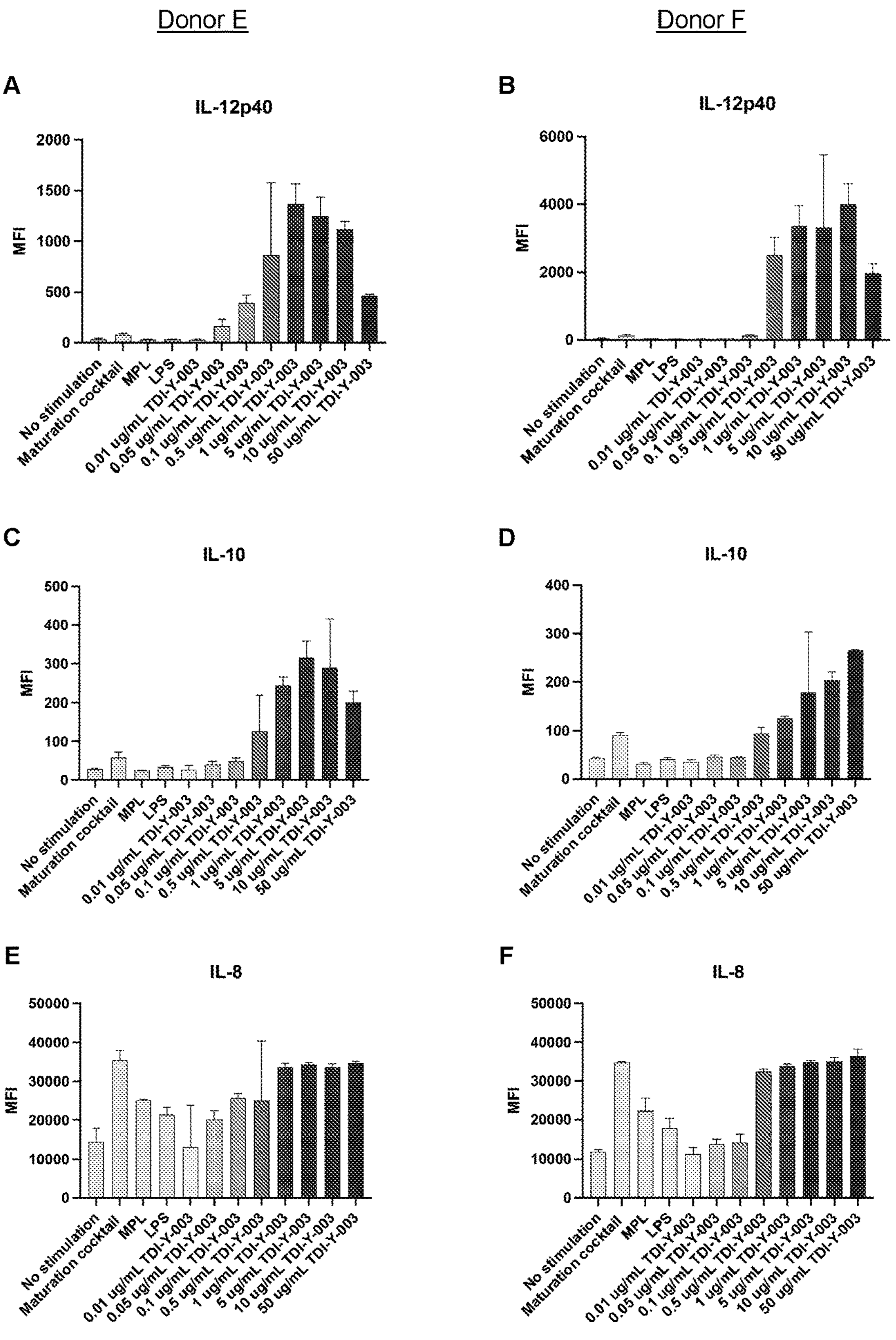
FIG. 9 A-J. Cytokine secretion of dendritic cells induced by TDI-Y-003. Dendritic cells from 2 different healthy donors were stimulated with increasing doses of TDI-Y-003. Negative (no stimulation) and positive (maturation cocktail, MPL, LPS) assay controls are shown. For each of Donor E and F, secretion of interleukin (IL)-12p40 (FIGS. 9 A and 9 B, respectively), IL-10 (FIGS. 9 C and 9 D, respectively), IL-8 ((FIGS. 9 E and 9 F, respectively), macrophage inflammatory protein (MIP)-1α (FIGS. 9 G and 9 H, respectively), and TNFα (FIGS. 9 I and 9 J, respectively) was analyzed by multiplex cytokine assay (Luminex).
Figure 9:
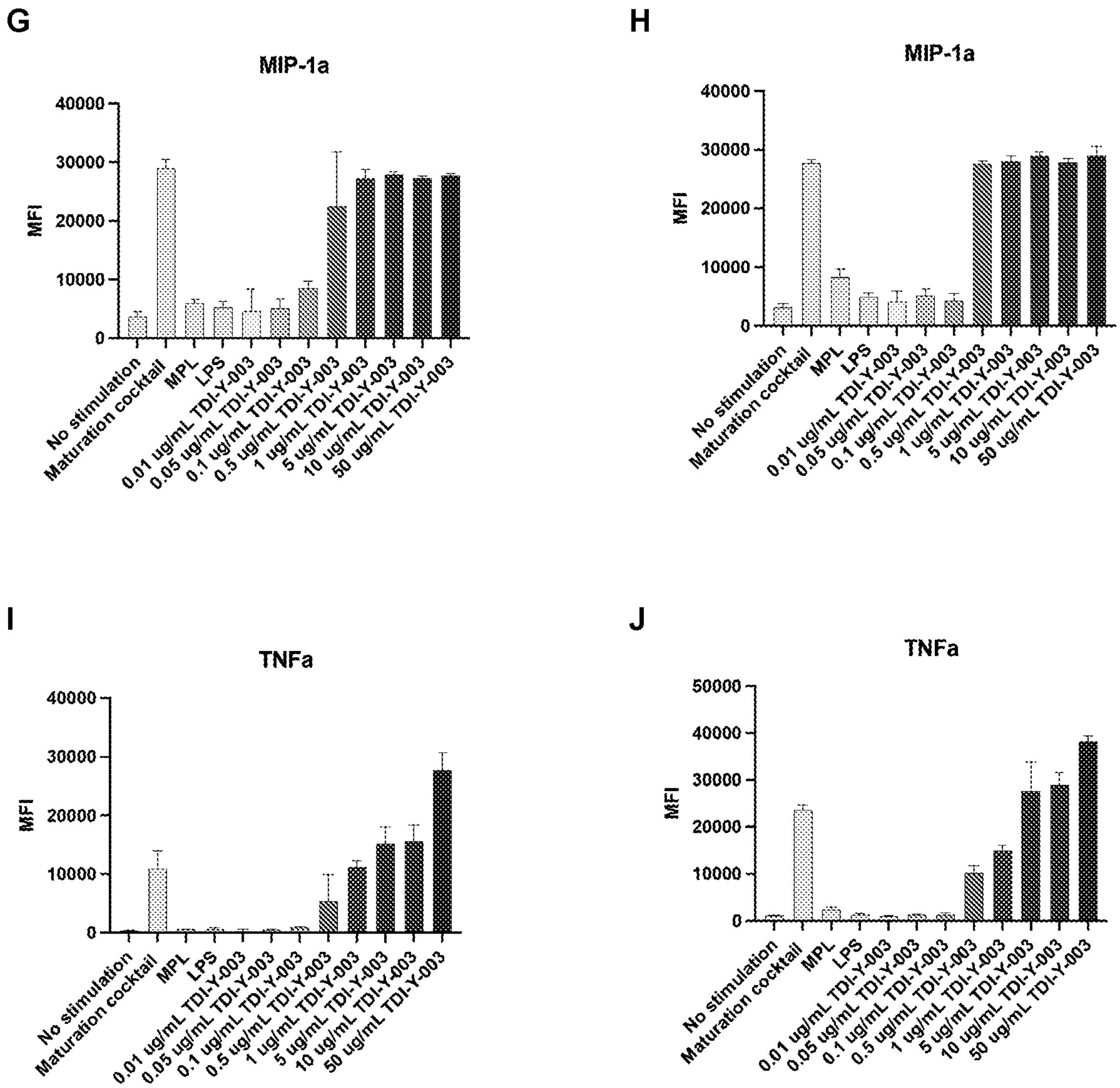

Differentiated, matured dendritic cells and other antigen presenting cells stimulated with TDI-Y-003 were also assessed for cytokine secretion. Secretion of the following cytokines were analyzed: IL-12p40, IL-10, IL-8, MIP-1α, and TNFα (FIG. 9). Results show that secretion increased in a dose-dependent manner for all cytokines tested in two different donors. Secretion of IL-8 and MIP1-α plateaued at higher concentrations.

The DC activation assay was also used to analyze the impact of abrogating the TDI-Y-003 antibody's ability to bind to the Fc receptor on the efficacy of the TDI-Y-003 antibody on activating dendritic cells. Differentiated and matured dendritic cells were stimulated for 48 hours with TDI-Y-003 (full version), a variant of TDI-Y-003 that includes Fc mutations that abrogate Fcγ receptor binding ("TDI-Y-003 hIgG2d"), a variant of TDI-Y-003 that is a bivalent pepsin-digested IgG with no Fc portion ("TDI-Y-003 F(ab)2"), a variant of TDI-Y-003 that is a monovalent pepsin-digested IgG with no Fc portion ("TDI-Y-003 F(ab)"), or human IgG2 isotype control, at concentrations ranging from 0.001 μg/mL to 100 μg/mL. A maturation cocktail, LPS, or MPL were used as positive controls to activate DCs. CD agonists CP-870893 (Pfizer) or selicrelumab (Roche) ("Ab1 hIgG2"), APX-005 (Apexigen) ("Ab2 hIgG1 S267E"), and dacetuzumab (Seattle-Genetics) ("Ab3-hIgG1") were also included as additional controls. DC activation markers HLA-ABC and CD80 were analyzed (FIG. 10).

Figure 10:
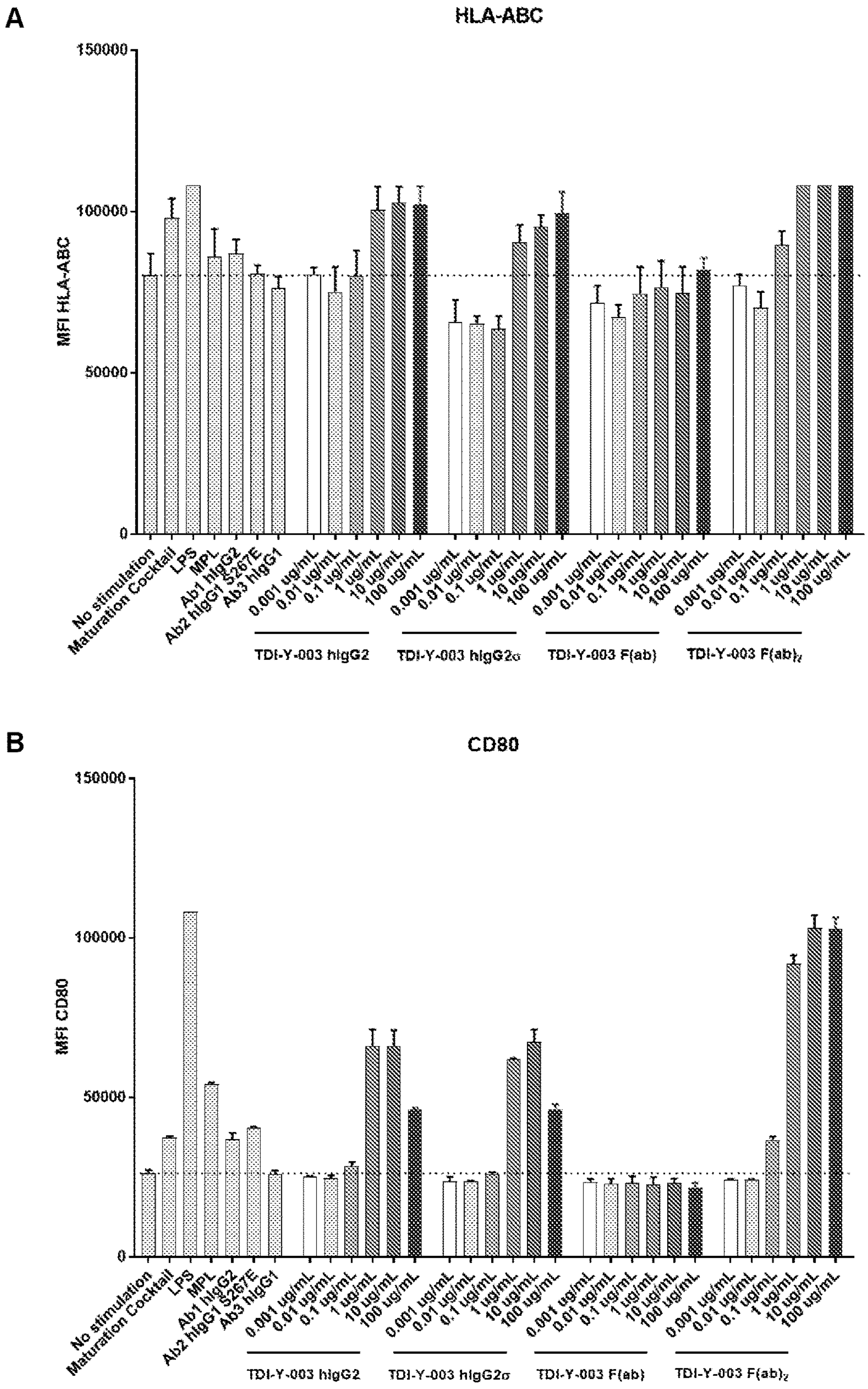
FIG. 10 A-B. Activation of dendritic cells by TDI-Y-003 or TDI-Y-003 FC-mutated variants. Dendritic cells from healthy donors were stimulated with increasing doses of TDI-Y-003 (full version), a variant of TDI-Y-003 that includes Fc mutations that abrogate Fcγ receptor binding ("TDI-Y-003 hIgG2d"), a variant of TDI-Y-003 that is a bivalent pepsin-digested IgG with no Fc portion ("TDI-Y-003 F(ab)2"), a variant of TDI-Y-003 that is a monovalent pepsin-digested IgG with no Fc portion ("TDI-Y-003 F(ab)"), or human IgG2 isotype control. Negative (no stimulation) and positive (maturation cocktail, LPS, MPL) assay controls are shown. CD agonists CP-870893 (Pfizer) or selicrelumab (Roche) ("Ab1 hIgG2"), APX-005 (Apexigen)

As shown in FIG. 10, TDI-Y-003 FC-mutated variants maintained efficacy in DC activation, despite that the Fc binding was abrogated. These results demonstrate that TDI-Y-003 binds and activates dendritic cells independent of Fc.

Additionally, the DC activation assay was used to compare the ability to activate dendritic cells of TDI-Y-003 with other CD40 agonists. In one study, differentiated and matured dendritic cells were stimulated for 48 hours with TDI-Y-003, CD40 agonist B016-Ab1 (equivalent to selicrelumab), or human IgG2 isotype control at concentrations ranging from 0.01 μg/mL to 5 μg/mL. A maturation cocktail and LPS were used as positive controls to activate DCs. As shown in FIG. 11, expression levels of HLA-ABC, HLA-DR, CD80, and CD86 increased in a dose-dependent manner, and expression of the activation markers in dendritic cells stimulated with TDI-Y-003 was generally greater than expression of the activation markers in dendritic cells stimulated with B016-Ab1.

In another study, differentiated and matured dendritic cells were stimulated for 48 hours with TDI-Y-003, CD40 agonist APX005M, CD40 agonist CDX-1140, or human IgG2 isotype control at concentrations of 0.1 μg/mL and 10 μg/mL. A maturation cocktail, LPS, or MPL were used as positive controls to activate DCs. As shown in FIG. 12, expression levels of HLA-ABC and CD86 increased in a dose-dependent manner, and expression of the activation markers in dendritic cells stimulated with TDI-Y-003 was generally greater than expression of the activation markers in dendritic cells stimulated with APX005M or CDX-1140.

To expand functional in vitro analyses of TDI-Y-003 efficacy to another antigen-presenting cell type, B cells were tested (FIG. 13). The human B-lymphoblastic cell line Raji was used as a cell culture model for human B cells. Raji cells were stimulated with TDI-Y-003 or human IgG2 isotype control at concentrations ranging from 0.01 μg/mL to 50 μg/mL. After 48 hours cells were washed, stained, and subjected to flow cytometry analysis. The following B cell activation markers were analyzed: HLA-ABC, HLA-DR, CD80, and CD86 (FIG. 14).

TDI-Y-003 efficacy was also studied on primary human B cells. The B cells were stimulated with TDI-Y-003 at concentrations ranging from 0.01 μg/mL to 50 μg/mL. After 48 hours cells were washed, stained, and subjected to flow cytometry analysis to study activation marker expression and cytokine secretion. CpG ODN was included as a positive control to activate B cells, and ctrl ODN was the corresponding control oligonucleotide. The following B cell activation markers were analyzed: HLA-ABC, HLA-DR, CD80, CD86, and CD70 (FIG. 15); and the following cytokines were analyzed: IFNγ, IL-10, IL-12p70, IL-13, IL-6, and TNFα (FIG. 16). The results show that TDI-Y-003 leads to dose-dependent increases in activation marker expression and cytokine secretion in human B cells.

T cells were used to analyze whether stimulation of antigen presenting cells by TDI-Y-003 can lead to activation of T cells (FIG. 17). PBMCs were isolated from leukocyte-enriched human blood by density gradient centrifugation and plated in cell culture dishes. After 1 hour non-adherent cells were cryopreserved and used to isolate T and B cells. Adherent monocytes were differentiated into monocyte-derived dendritic cells by culturing them in the presence of hIL-4 and hGM-CSF for 5-7 days. T cells were co-cultured with either the dendritic cells or CD19+ B cells in the presence of hIL-2 and hIL-15, stimulated with either LPS or TDI-Y-003, and with DMSO or CEF viral peptide pool. The results show that, when in the presence of T cells, stimulation of dendritic cells (FIG. 18) or B cells (FIG. 19) by TDI-Y-300 can lead to the activation of the T cells.

The in vivo efficacy of TDI-Y-003 was assessed using syngeneic B16F10 melanoma (known to be resistant to PD-1 and CTLA-4 blocakde[18,19]) in C57BL/6 transgenic mice engineered to express human CD40 and human FcγRs17. These mice recapitulate normal antibody pharmacokinetics as they include the human version of FcRn. These mice also contain a human IgG1 knock-in tolerizing them to human IgGs, allowing for repeated human antibody administration without excess risk of immunogenicity from exogenously administered human IgG antibodies.

Bilateral B16-F10 melanoma tumors were implanted in hCD40/hFcγRs mice by injecting $1\times10^6$ cells intradermally in two flanks in each mouse (FIG. 20). After the tumors were established, the mice were randomized to either the control or the experimental group (TDI-Y-003). The control group and the experimental group received 20 μg of antibody administered intratumorally (based on our prior experience with anti-mouse CD40, we used 4% of the usual systemic dose[12]). The control mice received human IgG2 isotype control and the treatment group received TDI-Y-003. Injections were administered to established tumors twice weekly for four weeks starting at day 8 after tumor implantation. Survival and tumor growth were monitored twice weekly.

Administration of TDI-Y-003 led to regression of injected tumors and delay of distant (nontreated) tumors, resulting in a significant survival benefit of the humanized mice with bilateral tumors (FIG. 21). These data support the use of this mAb as a monotherapy.

TDI-Y-003 resulted in greater tumor control as a monotherapy than our initial experiments using an anti-mouse CD40 antibody (FGK45) suggested[12]. The in vivo studies with TDI-Y-003 indicate that the antibody may confer clinical benefit as monotherapy.

In addition, the impact of abrogating TDI-Y-003's ability to bind to the Fc receptor on the in vivo efficacy of TDI-Y-003 was assessed. Bilateral B16-F10 melanoma tumors were implanted in hCD40/hFcγRs mice by injecting $1\times10^6$ cells intradermally in two flanks in each mouse. After the tumors were established, the mice were injected with TDI-Y-300 (20 μg), TDI-Y-003 hIgG2σ (which has Fc mutations that abrogate Fcγ receptor binding) (20 μg), or an isotype control intratumorally twice weekly for four weeks. Administration of TDI-Y-003 and TDI-Y-003 hIgG2σ each led to significant regression of injected tumors and to delay of distant tumors (FIG. 22). Further, mice injected with TDI-Y-003 or TDI-Y-003 hIgG2σ experienced a significantly greater probably of survival (FIG. 23). These results show that TDI-Y-003 demonstrates in vivo efficacy independent of its ability to bind to Fc.

Finally, a clonogenic assay was performed on in C57BL/6 mice having bilateral B16-F10 melanoma tumors as described above. Human IgG2 isotype control or TDI-Y-003 were injected into the established tumors at day 8 after tumor implantation. The tumors were then harvested within 24 hours and CD45+ cells were separated. The results show that there were significantly fewer tumor cell colonies from tumors injected with TDI-Y-003 (FIG. 24), suggesting that TDI-Y-003 may directly limit the proliferation of, or kill, melanoma tumor cells.

REFERENCE LIST

1. Wei, S. C., Duffy, C. R. & Allison, J. P. Fundamental Mechanisms of Immune Checkpoint Blockade Therapy. Cancer Discov 8, 1069-1086 (2018).
2. Gabrilovich, D. I., Corak, J., Ciernik, I. F., Kavanaugh, D. & Carbone, D. P. Decreased antigen presentation by dendritic cells in patients with breast cancer. Clin Cancer Res 3, 483-490 (1997).
3. Nagorsen, D., et al. Tumor-infiltrating macrophages and dendritic cells in human colorectal cancer: relation to local regulatory T cells, systemic T-cell response against tumor-associated antigens and survival. J Transl Med 5, 62 (2007).
4. Perrot, I., et al. Dendritic cells infiltrating human non-small cell lung cancer are blocked at immature stage. J Immunol 178, 2763-2769 (2007).
5. Troy, A., Davidson, P., Atkinson, C. & Hart, D. Phenotypic characterisation of the dendritic cell infiltrate in prostate cancer. J Urol 160, 214-219 (1998).
6. Caux, C., et al. Activation of human dendritic cells through CD40 cross-linking. J Exp Med 180, 1263-1272 (1994).
7. Byrne, K. T. & Vonderheide, R. H. CD40 Stimulation Obviates Innate Sensors and Drives T Cell Immunity in Cancer. Cell Rep 15, 2719-2732 (2016).
8. de Vos, S., et al. A phase II study of dacetuzumab (SGN-40) in patients with relapsed diffuse large B cell lymphoma (DLBCL) and correlative analyses of patient-specific factors. J Hematol Oncol 7, 44 (2014).
9. Vonderheide, R. H., et al. Clinical activity and immune modulation in cancer patients treated with CP-870,893, a novel CD40 agonist monoclonal antibody. J Clin Oncol 25, 876-883 (2007).
10. Vonderheide, R. H., et al. Phase I study of recombinant human CD40 ligand in cancer patients. J Clin Oncol 19, 3280-3287 (2001).
11. O'Hara, M. H., et al. A Phase 1b study of CD40 agonistic monoclonal antibody APX005M together with gemcitabine (Gem) and nab-paclitaxel (NP) with or without nivolumab (Nivo) in untreated metastatic ductal pancreatic adenocarcinoma (PDAC) patients. Cancer Research 79(2019).
12. Khalil, D. N., et al. In situ vaccination with defined factors overcomes T cell exhaustion in distant tumors. J Clin Invest 130(2019).
13. Li, F. B. & Ravetch, J. V. Inhibitory Fc gamma Receptor Engagement Drives Adjuvant and Anti-Tumor Activities of Agonistic CD40 Antibodies. Science 333, 1030-1034 (2011).
14. Piechutta, M. & Berghoff, A. S. New emerging targets in cancer immunotherapy: the role of Cluster of Differentiation 40 (CD40/TNFR5). ESMO Open 4, e000510 (2019).
15. A Study Investigating the Safety and Tolerability of an Immune Treatment in Cancer Patients With Lesions to the Skin. https://clinicaltrials.gov/ct2/show/NCT04059588.
16. Engblom, C., Pfirschke, C. & Pittet, M. J. The role of myeloid cells in cancer therapies. Nat Rev Cancer 16, 447-462 (2016).
17. Dahan, R., et al. Therapeutic Activity of Agonistic, Human Anti-CD40 Monoclonal Antibodies Requires Selective FcgammaR Engagement. Cancer Cell 29, 820-831 (2016).
18. Fu, J., et al. Preclinical evidence that PD1 blockade cooperates with cancer vaccine TEGVAX to elicit regression of established tumors. Cancer Res 74, 4042-4052 (2014).

The invention claimed is:

1. An isolated CD40 binding molecule comprising:
(i) CDR H1 and CDR H2 regions of SEQ ID NO. 1,
(ii) CDR H3 region of SEQ ID NO. 1, 3, 5, 7, or 17, and
(iii) CDR L1, CDR L2, and CDR L3 regions of SEQ ID NO. 2,
wherein the molecule binds to, and is an agonist of, human CD40.

2. The isolated CD40 binding molecule of claim 1, comprising the CDR H3 region of SEQ ID NO. 1.

3. An isolated CD40 binding molecule comprising:
(i) CDR H1 and CDR H2 regions of SEQ ID NO. 1,
(ii) CDR H3 region comprising, and
(iii) CDR L1, CDR L2, and CDR L3 regions of SEQ ID NO. 2,
wherein the molecule binds to, and is an agonist of, human CD40.

4. The isolated CD40 binding molecule according to claim 1, comprising:
(a) a heavy chain variable region comprising amino acids 1-121 of SEQ ID NO. 1, and
(b) a light chain variable region comprising amino acids 1-113 of SEQ ID NO. 2.

5. The isolated CD40 binding molecule according to claim 1, comprising:
(a) a heavy chain variable region comprising SEQ ID NO. 3, SEQ ID NO. 5, SEQ ID NO. 7 or SEQ ID NO. 17, and
(b) a light chain variable region comprising SEQ ID NO. 4, SEQ ID NO. 6, SEQ ID NO. 8 or SEQ ID NO. 18.

6. The isolated CD40 binding molecule according to claim 1, comprising:
(a) a heavy chain comprising SEQ ID NO. 1, and
(b) a light chain comprising SEQ ID NO. 2.

7. The isolated CD40 binding molecule according to claim 1, wherein the binding molecule is a humanized antibody, a fully human antibody, a chimeric antibody, a bi-specific antibody, or a multi-specific antibody.

8. A pharmaceutical composition comprising a CD40 binding molecule according to claim 1 and a pharmaceutically acceptable carrier.

9. A method of activating CD40 in an immune cell, the method comprising contacting an immune cell that expresses CD40 with an effective amount of a CD40 binding molecule according to claim 1, thereby activating CD40 in the cell.

10. A method of activating a T cell that is in the presence of an antigen presenting cell, the method comprising contacting the antigen presenting cell with an effective amount of a CD40 binding molecule according to claim 1, thereby activating the T cell.

11. A method of treating melanoma in a subject in need thereof, the method comprising administering to a subject that has melanoma an effective amount of a CD40 binding molecule according to claim 1.

12. A method of detecting CD40 in a sample, the method comprising contacting a cell or tissue sample with a CD40 binding molecule according to claim 1 and performing an assay to determine whether the CD40 binding molecule binds to the cell or tissue sample, wherein if the CD40 binding molecule binds to the cell or tissue sample the cell or tissue sample contains CD40.

13. The isolated CD40 binding molecule according to claim 3, wherein:
(i) CDR H1 domain comprises SEQ ID NO. 9,
(ii) CDR H2 domain comprises SEQ ID NO. 10, and
(iii) CDR H3 domain comprises SEQ ID NO. 11, 14 or 15, and
(iv) CDR L1 domain comprises SEQ ID NO. 12,
(v) CDR L2 domain comprises amino acid sequence FTS, and
(vi) CDR L3 domain comprises SEQ ID NO. 13.

14. The isolated CD40 binding molecule according to claim 3, wherein the binding molecule is a humanized antibody, a fully human antibody, a chimeric antibody, a bi-specific antibody, or a multi-specific antibody.

15. A pharmaceutical composition comprising a CD40 binding molecule according to claim 3 and a pharmaceutically acceptable carrier.

16. A method of activating CD40 in an immune cell, the method comprising contacting an immune cell that expresses CD40 with an effective amount of a CD40 binding molecule according to claim 3, thereby activating CD40 in the cell.

17. A method of activating a T cell that is in the presence of an antigen presenting cell, the method comprising contacting the antigen presenting cell with an effective amount of a CD40 binding molecule according to claim 3, thereby activating the T cell.

18. A method of treating melanoma in a subject in need thereof, the method comprising administering to a subject that has melanoma an effective amount of a CD40 binding molecule according to claim 3.

19. A method of detecting CD40 in a sample, the method comprising contacting a cell or tissue sample with a CD40 binding molecule according to claim 3 and performing an assay to determine whether the CD40 binding molecule binds to the cell or tissue sample, wherein if the CD40 binding molecule binds to the cell or tissue sample the cell or tissue sample contains CD40.

* * * * *

SEQUENCE LISTING

<160> NUMBER OF SEQ ID NOS: 19

<210> SEQ ID NO 1
<211> LENGTH: 446
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Gly Leu His Trp Ile Arg Gln Pro Pro Gly Lys Gly Leu Glu Trp Ile
        35                  40                  45

Gly Val Ile Trp Arg Gly Gly Asn Thr Asp Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys Asn Ser Tyr Tyr Gly Gln Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
```

385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly
435 440 445

<210> SEQ ID NO 2
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu His Ser
20 25 30

Phe Asn Gln Lys Asn Tyr Leu Ala Trp Tyr Gln Gln Lys Pro Gly Gln
35 40 45

Pro Pro Lys Leu Leu Ile Tyr Phe Thr Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

His Tyr Thr Thr Pro Phe Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Gln Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Thr Thr Tyr

```
            20                  25                  30

Gly Leu His Trp Ile Arg Gln Pro Pro Gly Lys Gly Leu Glu Trp Ile
        35                  40                  45

Gly Val Ile Trp Arg Gly Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Asn Ser Tyr Tyr Gly Asn Gly Gly His Ala Met Asp Tyr Trp Gly
            100                 105                 110

Gln Gly Thr Leu Val Thr Val Ser Ser
        115                 120


<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu His Ser
            20                  25                  30

Phe Asn Gln Lys Asn Tyr Leu Ala Trp Tyr Gln Gln Lys Pro Gly Gln
        35                  40                  45

Pro Pro Lys Leu Leu Ile Tyr Phe Thr Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Thr Thr Pro Phe Thr Phe Gly Gln Gly Thr Lys Leu Glu Ile
            100                 105                 110

Lys


<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Gly Leu His Trp Ile Arg Gln Pro Pro Gly Lys Gly Leu Glu Trp Ile
        35                  40                  45

Gly Val Ile Trp Arg Gly Gly Asn Thr Asp Tyr Asn Pro Ser Leu Lys
    50                  55                  60

Ser Arg Val Thr Ile Ser Lys Asp Thr Ser Lys Asn Gln Val Ser Leu
65                  70                  75                  80
```

```
Lys Leu Ser Ser Val Thr Ala Ala Asp Thr Ala Val Tyr Tyr Cys Ala
                85                  90                  95

Lys Asn Ser Tyr Tyr Gly Asn Gly Gly His Ala Met Asp Tyr Trp Gly
            100                 105                 110

Gln Gly Thr Leu Val Thr Val Ser Ser
        115                 120


<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu His Ser
            20                  25                  30

Phe Asn Gln Lys Asn Tyr Leu Ala Trp Tyr Gln Gln Lys Pro Gly Gln
        35                  40                  45

Pro Pro Lys Leu Leu Ile Tyr Phe Thr Ser Thr Arg Glu Ser Gly Val
    50                  55                  60

Pro Asp Arg Phe Leu Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Thr Thr Pro Phe Thr Phe Gly Gln Gly Thr Lys Leu Glu Ile
            100                 105                 110

Lys


<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Thr Tyr
            20                  25                  30

Gly Met His Trp Val Arg Gln Ala Pro Gly Lys Gly Leu Glu Trp Val
        35                  40                  45

Ala Val Ile Trp Arg Gly Gly Asn Thr Asp Tyr Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ser Tyr Tyr Gly Asn Gly Gly His Ala Met Asp Tyr Trp
            100                 105                 110

Gly Gln Gly Thr Leu Val Thr Val Ser Ser
        115                 120
```

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Asp Ile Val Met Thr Gln Val Pro Val Ser Leu Ala Val Ser Leu Gly
1 5 10 15

Glu Arg Ala Thr Ile Asn Cys Lys Ser Ser Gln Ser Leu Leu His Ser
20 25 30

Phe Asn Gln Lys Asn Tyr Leu Ala Trp Tyr Gln Gln Lys Pro Gly Gln
35 40 45

Ser Pro Lys Leu Leu Ile Tyr Phe Thr Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Phe Cys Gln Gln
85 90 95

His Tyr Thr Thr Pro Phe Thr Phe Gly Gln Gly Thr Lys Leu Glu Ile
100 105 110

Lys

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gly Phe Ser Leu Thr Thr Tyr Gly
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ile Trp Arg Gly Gly Asn Thr
1 5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ala Lys Asn Ser Tyr Tyr Gly Asn Gly Gly His Ala Met Asp Tyr
1 5 10 15

<210> SEQ ID NO 12
<211> LENGTH: 12

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gln Ser Leu Leu His Ser Phe Asn Gln Lys Asn Tyr
1 5 10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gln Gln His Tyr Thr Thr Pro Phe Thr
1 5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Ala Lys Asn Ser Tyr Tyr Gly Asp Gly Gly His Ala Met Asp Tyr
1 5 10 15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Ala Lys Asn Ser Tyr Tyr Gly Gln Gly Gly His Ala Met Asp Tyr
1 5 10 15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: A, R, N, D, E, Q, G, H, I, L, K, M, F, S, T, W,
Y or V

<400> SEQUENCE: 16

Ala Lys Asn Ser Tyr Tyr Gly Xaa Gly Gly His Ala Met Asp Tyr
1 5 10 15

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Thr Tyr
20 25 30

Gly Leu His Trp Val Arg Gln Ser Pro Gly Lys Gly Leu Glu Trp Leu
35 40 45

Gly Val Ile Trp Arg Gly Gly Asn Thr Asp Tyr Asn Ala Ala Phe Met
50 55 60

Ser Arg Leu Ser Ile Thr Lys Asp Asn Ser Lys Ser Gln Val Phe Phe
65 70 75 80

Lys Met Asn Ser Leu Gln Ala Asp Asp Thr Ala Ile Tyr Tyr Cys Ala
85 90 95

Lys Asn Ser Tyr Tyr Gly Asn Gly Gly His Ala Met Asp Tyr Trp Gly
100 105 110

Gln Gly Thr Ser Val Thr Val Ser Ser
115 120

<210> SEQ ID NO 18
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Asp Ile Val Met Thr Gln Ser Pro Ser Ser Leu Ala Met Ser Val Gly
1 5 10 15

Gln Lys Val Thr Met Ser Cys Lys Ser Ser Gln Ser Leu Leu His Ser
20 25 30

Phe Asn Gln Lys Asn Tyr Leu Ala Trp Tyr Gln Gln Arg Pro Gly Gln
35 40 45

Ser Pro Lys Leu Leu Ile Tyr Phe Thr Ser Thr Arg Glu Ser Gly Val
50 55 60

Pro Asp Arg Phe Leu Gly Ser Gly Ser Gly Thr Asp Phe Thr Leu Thr
65 70 75 80

Ile Ser Ser Val Gln Ala Glu Asp Leu Ala Asp Tyr Phe Cys Gln Gln
85 90 95

His Tyr Thr Thr Pro Phe Thr Phe Gly Ser Gly Thr Lys Leu Glu Ile
100 105 110

Lys

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 19

His His His His His His
1 5